(12) United States Patent
Mantell et al.

(10) Patent No.: US 6,753,322 B2
(45) Date of Patent: Jun. 22, 2004

(54) 2-AMINOCARBONYL-9H-PURINE DERIVATIVES

(75) Inventors: Simon John Mantell, Kent (GB); Peter Thomas Stephenson, Kent (GB)

(73) Assignee: Pfizer Inc, New York, NY (US)

( * ) Notice: Subject to any disclaimer, the term of this patent is extended or adjusted under 35 U.S.C. 154(b) by 145 days.

(21) Appl. No.: 09/874,007

(22) Filed: Jun. 5, 2001

(65) Prior Publication Data

US 2002/0058641 A1 May 16, 2002

Related U.S. Application Data

(60) Provisional application No. 60/214,307, filed on Jun. 27, 2000, provisional application No. 60/225,236, filed on Aug. 15, 2000, and provisional application No. 60/245,243, filed on Nov. 2, 2000.

(30) Foreign Application Priority Data

| Jun. 6, 2000 | (GB) | ............................................. 0014048 |
| Jul. 25, 2000 | (GB) | ............................................. 0018246 |
| Oct. 11, 2000 | (GB) | ............................................. 0024920 |

(51) Int. Cl.[7] .............................................. A61K 31/70
(52) U.S. Cl. .......................... 514/46; 514/45; 536/27.1; 536/27.3; 536/27.2; 536/27.21; 536/27.23
(58) Field of Search .............................. 536/27.1, 27.3, 536/27.2, 27.21, 27.23; 514/45, 46

(56) References Cited

FOREIGN PATENT DOCUMENTS

| WO | 9111172 | 8/1991 | ............ A61K/9/00 |
| WO | 9402518 | 2/1994 | ........... C08B/37/16 |
| WO | 9855148 | 12/1998 | ........... A61K/47/48 |
| WO | 9965895 | 12/1999 | ......... C07D/401/04 |

OTHER PUBLICATIONS

Jacobson, Kenneth A. et al., "Adenosine Receptors: Pharmacology, Structure–Activity Relationships, and Therapeutic Potential," Journal of Medicinal Chemistry, 1992, 35 (3), 407–422.*

Olsson, R. A. et al., "N6–Substituted N-Alkyladenosine-5'–uronamides: Bifunctional Ligands Having Recognition Groups for A1 and A2 Adenosine Receptors," Journal of Medicinal Chemistry, 1986, 29 (9), 1683–1689.*

Monatsh. Chem., 88, pp. 35– (1957).

J. Amer. Chem. Soc., 80, pp. 5168–5173 (1958).

Justus Liebigs Ann. Chem., 648, pp. 72–82 (1961).

J. Chem. Soc. Perkin Trans. 1, 11, pp. 1205–1211 (1996); and.

Berge, et al., J. Pharm. Sci., 66, pp. 1–19 (1977).

* cited by examiner

Primary Examiner—James O. Wilson
Assistant Examiner—Josephine Young
(74) Attorney, Agent, or Firm—Peter C. Richardson; Gregg C. Benson; Robert T. Ronau

(57) ABSTRACT

The present invention relates to compounds of the formula:

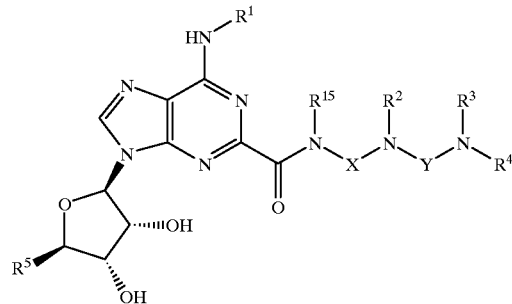

(I)

and pharmaceutically acceptable salts and solvates thereof, and to processes for the preparation of, intermediates used in the preparation of, compositions containing and the uses of, such compounds.

53 Claims, No Drawings

2-AMINOCARBONYL-9H-PURINE DERIVATIVES

This application claims the benefit under 37 C.F.R. §1.78(a)(3) and (4) of the following prior filed U.S. provisional applications: No. 60/214,307, filed Jun. 27, 2000; No. 60/225,236, filed Aug. 15, 2000; and No. 60/245,243, filed Nov. 2, 2000.

Priority is hereby claimed under 37 C.F.R. §1.55(a) of the following previously filed foreign applications: GB 0014048.3, filed Jun. 6, 2000; GB 0018246.9, filed Jul. 25, 2000; and GB 0024920.1, filed Oct. 11, 2000.

This invention relates to purine derivatives. More particularly, this invention relates to 2-aminocarbonyl-9H-purine derivatives and to processes for the preparation of, intermediates used in the preparation of, compositions containing and the uses of, such derivatives.

These derivatives are selective, functional agonists of the human adenosine A2a receptor and may be used as anti-inflammatory agents in the treatment of, inter alia, diseases of the respiratory tract.

Adenosine is a ubiquitous molecule having a central role in mammalian intermediary metabolism. Independently, adenosine acts on multiple surface receptors to produce a variety of responses. Adenosine receptor classification has revealed the presence of at least four subtypes: A1, A2a, A2b and A3. Stimulation of adenosine A2 receptors on the surface of human neutrophils has been reported to potently inhibit a range of neutrophil functions. Activated neutrophils can damage lung tissue by release of reactive oxygen species, for example, superoxide anion radicals ($O_2^-$), and granule products, for example, human neutrophil elastase (HNE), amongst other inflammatory mediators. In addition, activated neutrophils perform both de novo synthesis and release of arachidonate products such as leukotriene $B_4$ ($LTB_4$). $LTB_4$ is a potent chemo-attractant that recruits additional neutrophils to the inflammatory focus, whereas released $O_2^-$ and HNE adversely affect the pulmonary extracellular matrix. The A2 receptor subtype mediating many of these responses ($O_2^-$ and $LTB_4$/HNE release and cell adhesion) is established as A2a. The A2 subtype (A2a or A2b) mediating the other effects remains to be established.

Selective agonist activity at the A2a receptor is considered to offer greater therapeutic benefit than the use of non-selective adenosine receptor agonists because interaction with other subtypes is associated with detrimental effects in the lung in animal models and human tissue studies. For example, asthmatics, but not non-asthmatics, bronchoconstrict when challenged with inhaled adenosine. This response is at least in part due to the activation of the A1 receptor subtype. Activation of A1 receptors also promotes neutrophil chemotaxis and adherence to endothelial cells, thus promoting lung injury. Furthermore, many patients with respiratory disease will be co-prescribed $\beta_2$-agonists, and negative interaction has been shown in animal studies between isoprenaline and adenosine receptors negatively coupled to adenylate cyclase. Degranulation of human mast cells is promoted by activation of adenosine A2b receptors, thus selectivity over the A2b receptor is also advantageous.

We have now surprisingly found the present purine derivatives inhibit neutrophil function and are selective agonists of the adenosine A2a receptor. They may also have antagonist activity at the adenosine A3 receptor. The present compounds may be used to treat any disease for which an adenosine A2a receptor agonist is indicated. They can be used to treat a disease where leukocyte (e.g. neutrophil, eosinophil, basophil, lymphocyte, macrophage)-induced tissue damage is implicated. They are useful as anti-inflammatory agents in the treatment of diseases of the respiratory tract such as adult respiratory distress syndrome (ARDS), bronchitis, chronic bronchitis, chronic obstructive pulmonary disease, cystic fibrosis, asthma, emphysema, bronchiectasis, chronic sinusitis and rhinitis. The present compounds may also be used in the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing.

Accordingly, in a first embodiment, the present invention provides a compound of the formula:

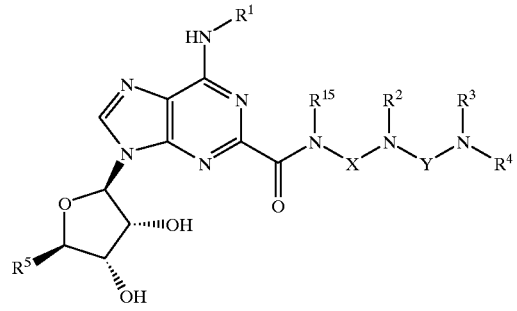

(I)

or a pharmaceutically acceptable salt or solvate thereof, wherein $R^1$ is H, $C_1$–$C_6$ alkyl or fluorenyl, said $C_1$–$C_6$ alkyl being optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

(A) $R^2$ is H or $C_1$–$C_6$ alkyl, $R^{15}$ is H or $C_1$–$C_6$ alkyl, and X is either (i) unbranched $C_2$–$C_3$ alkylene optionally substituted by $C_1$–$C_6$ alkyl or $C_3$–$C_8$ cycloalkyl, or (ii) a group of the formula:

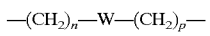

where W is $C_5$–$C_7$ cycloalkylene optionally substituted by $C_1$–$C_6$ alkyl, n is 0 or 1 and p is 0 or 1, or (B) $R^{15}$ is H or $C_1$–$C_6$ alkyl, and $R^2$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, or (C) $R^2$ is H or $C_1$–$C_6$ alkyl, and $R^{15}$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$, or, $R^3$ is H, $C_1$–$C_6$ alkyl, $C_3$–$C_5$ cycloalkyl or benzyl and $R^4$ is
- (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or
- (b) —($C_2$–$C_6$ alkylene)-$R^8$,
- (c) —($C_1$–$C_6$ alkylene)-$R^{13}$, or
- (d) $C_1$–$C_6$ alkyl or $C_3$–$C_8$ cycloalkyl;

$R^5$ is $CH_2OH$ or $CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, $COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or
(ii) $NR^{11}R^{12}$;

$R^9$ is H, $C_1$–$C_6$ alkyl $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, $C_2$–$C_5$ alkanoyl or —$SO_2NR^9R^9$;

$R^{13}$ is (a) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)—CN, —$CO_2H$, —($C_1$–$C_3$ alkylene)-$CO_2H$, —$CO_2$($C_1$–$C_6$ alkyl), —($C_1$–$C_3$ alkylene)-$CO_2$($C_1$–$C_6$ alkyl), —($C_1$–$C_3$ alkylene)-$NR^{14}R^{14}$, —$CONR^{14}R^{14}$ or —($C_1$–$C_3$ alkylene)-$CONR^{14}R^{14}$, or (b) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het;

$R^{14}$ is H or $C_1$–$C_6$ alkyl optionally substituted by cyclopropyl;

m is 0, 1 or 2;

Y is CO, CS, $SO_2$ or C=N(CN); and

"het", used in the definition of $R^4$ and $R^{13}$, is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo.

In a second embodiment, the present invention provides a compound of the formula:

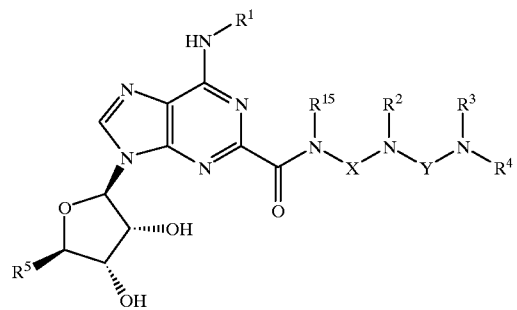

(I)

or a pharmaceutically acceptable salt or solvate thereof, wherein $R^1$ is H, $C_1$–$C_6$ alkyl or fluorenyl, said $C_1$–$C_6$ alkyl being optionally substituted by 1 or 2 substituents each independently selected from phenyl and naphthyl, said phenyl and naphthyl being optionally substituted by $C_1$–$C_6$ alkyl, $C_1$–$C_6$ alkoxy, halo or cyano;

$R^2$ is H or $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$, or, $R^3$ is H, $C_1$–$C_6$ alkyl, $C_3$–$C_8$ cycloalkyl or benzyl and $R^4$ is
- (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or
- (b) —($C_2$–$C_6$ alkylene)-$R^8$, or
- (c) —($C_1$–$C_6$ alkylene)-$R^{13}$;

$R^5$ is $CH_2OH$ or $CONR^{14}R^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-$(C_2$–$C_6)$-alkyl, $R^9R^9N$—$(C_2$–$C_6)$-alkyl, fluoro-$(C_1$–$C_6)$-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) $NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-$(C_1$–$C_6)$-alkyl, —$CONR^9R^9$, —$COOR^{10}$, $C_2$–$C_5$ alkanoyl or —$SO_2NR^9R^9$;

$R^{13}$ is phenyl, pyridin-2-yl, pyridin-3-yl or pyridin-4-yl, each being optionally substituted by $C_1$–$C_6$ alkyl, $C_1$–$C_6$ alkoxy, halo or cyano;

$R^{14}$ is H or $C_1$–$C_6$ alkyl optionally substituted by cyclopropyl;

$R^{15}$ is H or $C_1$–$C_6$ alkyl;

m is 0, 1 or 2;

X is unbranched $C_2$–$C_3$ alkylene optionally substituted by $C_1$–$C_6$ alkyl or $C_3$–$C_8$ cycloalkyl;

Y is CO, CS, $SO_2$ or C=N(CN), and

"het", used in the definition of $R^4$, is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo.

In the above definitions, halo means fluoro, chloro, bromo or iodo and alkyl, alkylene, alkanoyl and alkoxy groups containing the requisite number of carbon atoms, except where indicated, can be unbranched or branched chain. Examples of alkyl include methyl, ethyl, n-propyl, i-propyl, n-butyl, i-butyl, sec-butyl and t-butyl. Examples of alkoxy include methoxy, ethoxy, n-propoxy, i-propoxy, n-butoxy, i-butoxy, sec-butoxy and t-butoxy. Examples of alkanoyl include acetyl and propanoyl. Examples of alkylene include methylene, 1,1-ethylene, 1,2-ethylene, 1,3-propylene and 1,2-propylene. Examples of cycloalkyl include cyclopropyl, cyclobutyl, cyclopentyl, cyclohexyl and cycloheptyl (the corresponding examples for cycloalkoxy also apply). Examples of cycloalkylene include cyclopentylene, cyclohexylene and cycloheptylene. "Het" can be aromatic or partially or fully saturated and "C-linked" means that it is attached to the neighbouring group by a ring carbon atom. Examples of "het" include pyrrolyl, imidazolyl, triazolyl, thienyl, furyl, thiazolyl, oxazolyl, thiadiazolyl, oxadiazolyl, pyridinyl, pyrimidinyl, pyridazinyl and pyrazinyl.

The pharmaceutically acceptable salts of the compounds of the formula (I) include the acid addition and the base salts thereof.

Suitable acid addition salts are formed from acids which form non-toxic salts and examples are the hydrochloride, hydrobromide, hydroiodide, sulphate, bisulphate, nitrate, phosphate, hydrogen phosphate, acetate, maleate, malate, fumarate, lactate, tartrate, citrate, gluconate, succinate, saccharate, benzoate, methanesulphonate, ethanesulphonate, benzenesulphonate, p-toluenesulphonate, pamoate, adipate and xinafoate (1-hydroxy-2-naphthoate) salts.

Suitable base salts are formed from bases which form non-toxic salts and examples are the sodium, potassium, aluminium, calcium, magnesium, zinc and diethanolamine salts.

For a review on suitable salts see Berge et al, J. Pharm. Sci., 66, 1–19, 1977.

The pharmaceutically acceptable solvates of the compounds of the formula (I) and salts thereof include hydrates thereof.

Also included within the present scope of the compounds of the formula (I) and salts thereof are polymorphs and radiolabelled derivatives thereof.

A compound of the formula (I) may contain one or more additional asymmetric carbon atoms and therefore exist in two or more stereoisomeric forms. The present invention includes the individual stereoisomers of the compounds of the formula (I) and, where appropriate, the individual tautomeric forms thereof, together with mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

Preferably, $R^1$ is $C_1$–$C_6$ alkyl optionally substituted by 1 or 2 phenyl substituents, said phenyl being optionally substituted by $C_1$–$C_6$ alkyl or halo.

Preferably, $R^1$ is $C_1$–$C_6$ alkyl optionally substituted by 1 or 2 phenyl substituents, said phenyl being optionally substituted by methyl or chloro.

Preferably, $R^1$ is $C_1$–$C_6$ alkyl optionally substituted by 1 or 2 phenyl substituents.

Preferably, $R^1$ is $C_1$–$C_6$ alkyl substituted by 1 or 2 phenyl substituents, said phenyl being optionally substituted by methyl or chloro.

Preferably, $R^1$ is $C_1$–$C_6$ alkyl substituted by 1 or 2 phenyl substituents.

Preferably, $R^1$ is $C_1$–$C_6$ alkyl substituted by 2 phenyl substituents, said phenyl being optionally substituted by methyl or chloro.

Preferably, $R^1$ is $C_1$–$C_6$ alkyl substituted by 2 substituents each independently selected from phenyl, 3-methylphenyl and 3-chlorophenyl.

Preferably, $R^1$ is $C_1$–$C_6$ alkyl substituted by 2 phenyl substituents.

Preferably, $R^1$ is diphenylethyl, bis(3-methylphenyl)ethyl or bis(3-chlorophenyl)ethyl.

Preferably, $R^1$ is diphenylethyl.

Preferably, $R^1$ is 2,2-diphenylethyl, 2,2-bis(3-methylphenyl)ethyl or 2,2-bis(3-chlorophenyl)ethyl.

Preferably, $R^1$ is 2,2-diphenylethyl.

Preferably, $R^2$ is H.

Preferably, $R^{15}$ is H.

Preferably, X is 1,2-ethylene or 1,3-propylene.

Preferably, X is 1,2-ethylene.

Preferably, $R^2$ is H, $R^{15}$ is H and X is 1,2-ethylene, 1,3-propylene or a group of the formula:

where W is $C_5$–$C_7$ cycloalkylene, n is 0 or 1 and p is 0 or 1.

Preferably, $R^2$ is H, $R^{15}$ is H and X is 1,2-ethylene, 1,3-propylene or a group of the formula:

where W is $C_5$–$C_7$ cycloalkylene, n is 0 and p is 0.

Preferably, $R^2$ is H, $R^{15}$ is H and X is 1,2-ethylene, 1,3-propylene or cyclohexylene.

Preferably, $R^2$ is H, $R^{15}$ is H and X is 1,2-ethylene, 1,3-propylene or 1,4-cyclohexylene.

Preferably, $R^2$ is H, $R^{15}$ is H and X is 1,2-ethylene, 1,3-propylene or trans-1,4-cyclohexylene.

Preferably, $R^2$ is H, $R^{15}$ is H and X is 1,2-ethylene.

Preferably, $R^{15}$ is H and $R^2$ and X, taken together with the nitrogen atom to which they are attached, represent 3-pyrrolidinyl or 3- or 4-piperidinyl, each being optionally substituted by $C_1$–$C_6$ alkyl.

Preferably, $R^{15}$ is H and $R^2$ and X, taken together with the nitrogen atom to which they are attached, represent 3-pyrrolidinyl or 4-piperidinyl each being optionally substituted by $C_1$–$C_6$ alkyl.

Preferably, $R^{15}$ is H and $R^2$ and X, taken together with the nitrogen atom to which they are attached, represent 3-pyrrolidinyl or 3- or 4-piperidinyl.

Preferably, $R^{15}$ is H and $R^2$ and X, taken together with the nitrogen atom to which they are attached, represent 3-pyrrolidinyl or 4-piperidinyl.

Preferably, $R^{15}$ is H and $R^2$ and X, taken together with the nitrogen atom to which they are attached, represent (3R)-pyrrolidinyl or 4-piperidinyl.

Preferably, $R^2$ is H and $R^{15}$ and X, taken together with the nitrogen atom to which they are attached, represent 3-pyrrolidinyl or 3- or 4-piperidinyl, each being optionally substituted by $C_1$–$C_6$ alkyl.

Preferably, $R^2$ is H and $R^{15}$ and X, taken together with the nitrogen atom to which they are attached, represent 3-pyrrolidinyl or 4-piperidinyl each being optionally substituted by $C_1$–$C_6$ alkyl.

Preferably, $R^2$ is H and $R^{15}$ and X, taken together with the nitrogen atom to which they are attached, represent 3-pyrrolidinyl or 3- or 4-piperidinyl.

Preferably, $R^2$ is H and $R^{15}$ and X, taken together with the nitrogen atom to which they are attached, represent 3-pyrrolidinyl or 4-piperidinyl.

Preferably, $R^2$ is H and $R^{15}$ and X, taken together with the nitrogen atom to which they are attached, represent (3R)-pyrrolidinyl, (3S)-pyrrolidinyl or 4-piperidinyl.

Preferably, $R^3$ is H.

Preferably, $R^4$ is piperidin-3-yl or piperidin-4-yl, each optionally substituted by benzyl or het as previously defined.

Preferably, $R^4$ is piperidin-3-yl or piperidin-4-yl, each optionally substituted by benzyl, pyridin-2-yl, pyridin-3-yl or pyridin-4-yl, said pyridin-2-yl, pyridin-3-yl and pyridin-4-yl each optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo.

Preferably, $R^4$ is piperidin-3-yl or piperidin-4-yl, each substituted by benzyl, pyridin-2-yl, pyridin-3-yl or pyridin-4-yl.

Preferably, $R^4$ is piperidin-3-yl or piperidin-4-yl, each substituted by benzyl.

Preferably, $R^4$ is piperidin-3-yl or piperidin-4-yl, each substituted by pyridin-2-yl.

Preferably, $R^4$ is piperidin-4-yl substituted by pyridin-2-yl.

Preferably, $R^4$ is 1-benzylpiperidin-4-yl.
Preferably, $R^4$ is 1-(pyridin-2-yl)piperidin-4-yl.
Preferably, $R^4$ is —($C_2$–$C_6$ alkylene)-$R^8$.
Preferably, $R^4$ is —$CH_2CH_2R^8$.
Preferably, $R^4$ is —($C_1$–$C_6$ alkylene)-$R^{13}$.
Preferably, $R^4$ is —$CH_2R^{13}$ or —$CH_2CH_2R^{13}$.
Preferably, $R^4$ is $C_3$–$C_8$ cycloalkyl.
Preferably, $R^4$ is cyclohexyl.

Preferably, $R^5$ is —$CH_2OH$ or —$CONH(C_1$–$C_6$ alkyl).
Preferably, $R^5$ is —$CH_2OH$ or —$CONHCH_2CH_3$.
Preferably, $R^5$ is —$CONHCH_2CH_3$.

Preferably, $R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl and said piperazin-1-yl and homopiperazin-1-yl being optionally substituted on the ring nitrogen atom not attached to the $C_2$–$C_6$ alkylene group by $C_1$–$C_6$ alkyl, or (ii) is $NR^{11}R^{12}$.

Preferably, $R^8$ is piperidin-1-yl or tetrahydroisoquinolin-1-yl each optionally substituted on a ring carbon atom by $C_1$–$C_6$ alkyl.

Preferably, $R^8$ is piperidin-1-yl optionally substituted on a ring carbon atom by isopropyl.

Preferably, $R^8$ is piperidin-1-yl, 4-isopropylpiperidin-1-yl or tetrahydroisoquinolin-1-yl.

Preferably $R^8$ is $NR^{11}R^{12}$ where $NR^{11}R^{12}$ is $N(C_1$–$C_6$ alkyl$)_2$, $N(C_1$–$C_6$ alkyl$)(C_3$–$C_8$ cycloalkyl) or $N(C_1$–$C_6$ alkyl)(benzyl).

Preferably $R^8$ is $NR^{11}R^{12}$ where $NR^{11}R^{12}$ is N,N-diisopropylamino, N,N-di-n-butylamino, N-cyclopentyl-N-isopropylamino, N-cyclohexyl-N-isopropylamino or N-benzyl-N-isopropylamino.

Preferably, $R^{11}$ is H or $C_1$–$C_6$ alkyl.
Preferably, $R^{11}$ is $C_1$–$C_6$ alkyl.
Preferably, $R^{11}$ is isopropyl or n-butyl.
Preferably, $R^{12}$ is H, $C_1$–$C_6$ alkyl, $C_3$–$C_8$ cycloalkyl or benzyl.
Preferably, $R^{12}$ is $C_1$–$C_6$ alkyl, $C_3$–$C_8$ cycloalkyl or benzyl.
Preferably, $R^{12}$ is isopropyl, cyclopentyl, cyclohexyl or benzyl.

Preferably, $R^{13}$ is either phenyl optionally substituted by —($C_1$–$C_3$ alkylene)-$NR^{14}R^{14}$ or —$CO_2H$, or piperidin-2-yl, piperidin-3-yl or piperidin-4-yl each optionally substituted by benzyl.

Preferably, $R^{13}$ is phenyl optionally substituted by —$CH_2N(CH_2CH_3)_2$ or —$CO_2H$, or piperidin-4-yl substituted by benzyl.

Preferably, $R^{13}$ is phenyl, 4-(N,N-diethylamino)methylphenyl, 4-carboxyphenyl or 1-benzylpiperidin-4-yl.
Preferably, $R^{14}$ is H or $C_1$–$C_6$ alkyl.
Preferably, $R^{14}$ is H or ethyl.
Preferably, Y is CO.
Preferably,

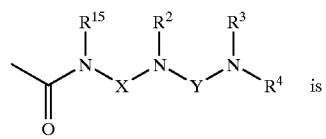 is

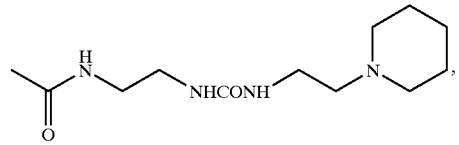,

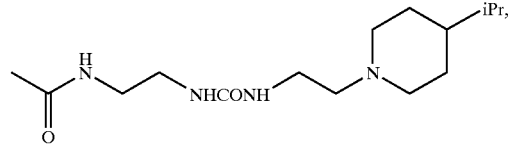

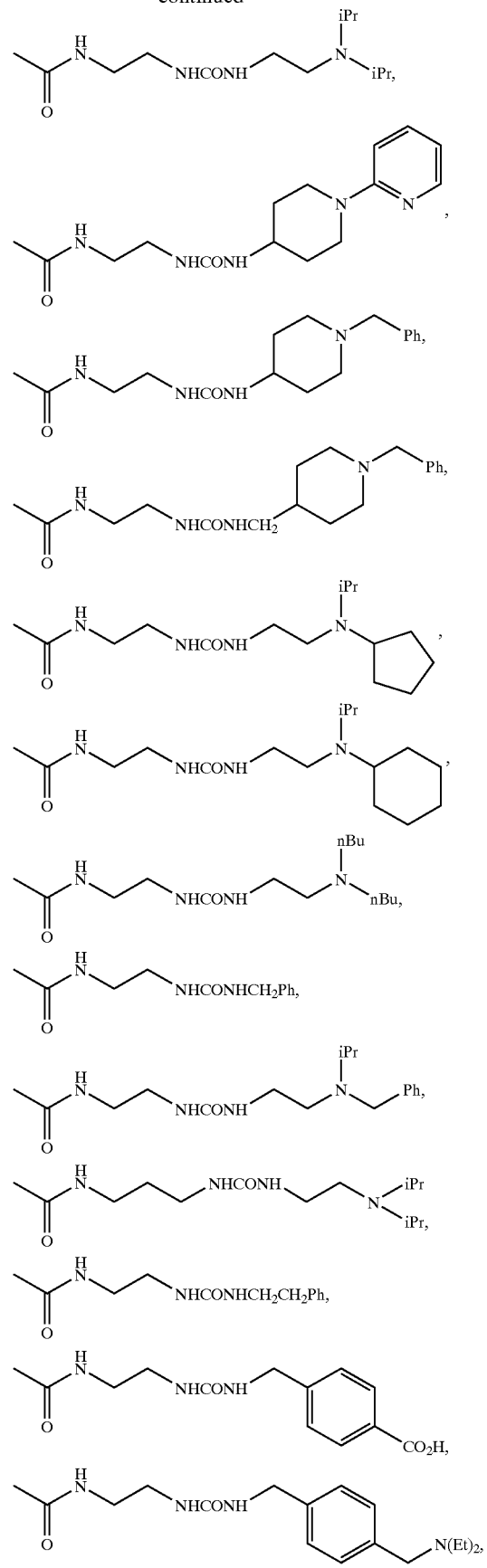

-continued

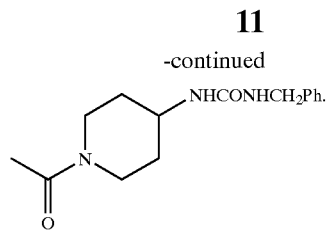

In the above preferred groups, "Et" means ethyl, "iPr" means isopropyl, "nBu" means n-butyl and "Ph" means phenyl.

Particularly preferred embodiments of a compound of the formula (I) are those of the Examples section hereafter, particularly those of Examples 8 and 34, together with pharmaceutically acceptable salts and solvates thereof.

The compounds of the formula (I) can be prepared using conventional procedures such as by the following illustrative methods in which $R^1$, $R^2$, $R^3$, $R^4$, $R^5$, $R^{15}$, X and Y are as previously defined for a compound of the formula (I) unless otherwise stated.

1. A compound of the formula (I) wherein Y is CO may be prepared by reaction of a compound of the formula:

(II)

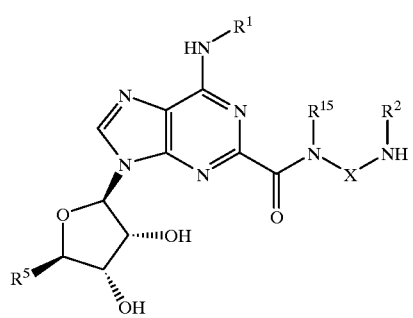

with a compound of the formula:

$R^3R^4NCOZ^1$ (III)

wherein $Z^1$ is a suitable leaving group such as chloro or 1H-imidazol-1-yl.

In a typical procedure the compounds are reacted together in a suitable solvent such as toluene, isopropanol or dichloromethane, or any combination thereof, optionally with heating such as at the reflux temperature of the solvent.

The compounds of the formula (III) may be prepared by conventional procedures.

A compound of the formula (II) may be prepared as shown in Scheme 1.

Scheme 1

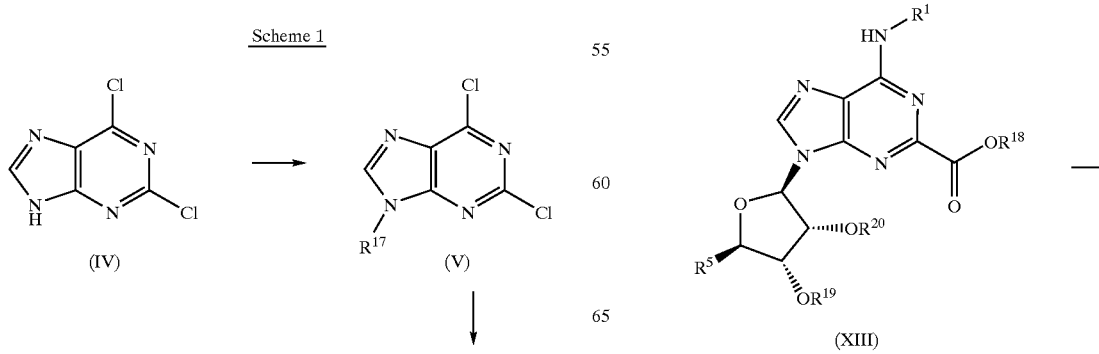

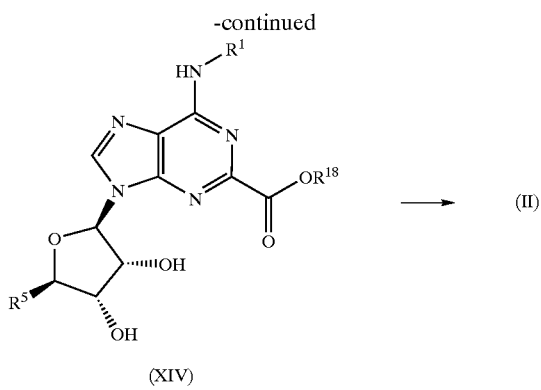

(XIV)

wherein $R^{16}$ is $C_1$–$C_4$ alkyl, $R^{17}$ is a suitable protecting group such as tetrahydro-2H-pyran-2-yl, $R^{18}$ is a suitable ester-forming group such as $C_1$–$C_6$ alkyl or benzyl, preferably $C_1$–$C_4$ alkyl, and $R^{19}$ and $R^{20}$ are either each a suitable protecting group such as acetyl or benzoyl, or, taken together, are a suitable protecting group such as $C_1$–$C_6$ alkylene optionally substituted by phenyl, e.g. 1,1-dimethylmethylene or phenylmethylene.

In a typical procedure, where $R^{17}$ is tetrahydro-2H-pyran-2-yl, a chloropurine of the formula (IV) is N-protected by reaction with 3,4-dihydro-2H-pyran in the presence of a suitable acid catalyst such as p-toluenesulphonic acid (PTSA), benzenesulphonic acid, camphorsulphonic acid, hydrochloric acid, sulphuric acid, methanesulphonic acid or pyridinium p-toluenesulphonate, and in a suitable solvent such as ethyl acetate, toluene, dichloromethane, dimethylformamide (DMF), tert-butyl methyl ether, diisopropyl ether, tetrahydrofuran (THF) or acetonitrile, at from 0° C. to the reflux temperature of the solvent Preferably the reaction is carried out in ethyl acetate in the presence of PTSA with heating Other suitable protecting groups $R^{17}$ are mentioned in the Greene et al reference mentioned herein.

A compound of the formula (V) prepared may be converted to an amine of the formula (VI) by reaction with a compound of the formula:

$R^1 N H_2$ (XVI).

The compounds are reacted in the presence of a suitable acid acceptor, e.g. triethylamine, 4-methylmorpholine or N-ethyldiisopropylamine, and in a suitable solvent such as methanol, ethanol or isopropanol at from room temperature to the reflux temperature of the solvent. Preferably, N-ethyldiisopropylamine and isopropanol are used under reflux conditions.

An amine of the formula (VI) is then reacted with a sodium or potassium thioalkoxide in a suitable solvent such as dimethylsulphoxide(DMSO), DMF or 1-methyl-2-pyrrolidinone, at from room temperature to the reflux temperature of the solvent. Preferably, sodium or potassium thiomethoxide in DMF at 100° C. are used as the reaction conditions.

A thioether of the formula (VII) prepared is then oxidised to a sulphone of the formula (VIII) using a suitable oxidant such as Oxone (trade mark) (potassium peroxymonosulphate), dimethyl dioxirane, m-chloroperbenzoic acid or peracetic acid, optionally in the presence of a suitable base, e.g. sodium bicarbonate, and in a suitable solvent such as aqueous acetone or dichloromethane, at a temperature of from room temperature to 50° C. Preferably, Oxone (trade mark) and sodium bicarbonate are used in a aqueous acetone at room temperature.

A sulphone of the formula (VIII) may be converted to a nitrile of the formula (IX) by reaction with a suitable cyanide source such as potassium cyanide, zinc cyanide, sodium cyanide or copper cyanide, and in a suitable solvent such as DMSO, DMF, 1-methyl-2-pyrrolidinone, THF or acetonitrile, at a temperature of from room temperature to the reflux temperature of the solvent. Preferred conditions are potassium cyanide in DMF at 120° C.

Alternatively, a chloropurine of the formula (VI) may be converted to a nitrile of the formula (IX) using a suitable cyanide source, e.g. potassium cyanide, zinc cyanide, sodium cyanide or copper cyanide, and in a suitable solvent, e.g. DMF, DMSO, 1-methyl-2-pyrrolidinone, THF or acetonitrile, optionally in the presence of a suitable palladium catalyst, e.g. tetrakis(triphenylphosphine)palladium (0), or palladium(II) acetate in combination with triphenylphosphine, tri-o-tolylphosphine, (R)- or (S)- or racemic-2,2'-bis(diphenylphosphino)-1,1'-binaphthyl or 1,1'-bis(diphenylphosphino)ferrocene, and optionally in the presence of a suitable base, e.g. triethylamine, 4-methylmorpholine or N-ethyldiisopropylamine, at temperature of from room temperature to the reflux temperature of the solvent (optionally under pressure). Alternatively the reaction may be carried out by reacting a chloropurine of the formula (VI) with sodium or potassium cyanide in a suitable solvent such as DMSO, 1-methyl-2-pyrrolidinone or DMF, at from room temperature to the reflux temperature of the solvent. Preferably the reaction is carried out using zinc cyanide, triethylamine and tetrakis(triphenylphosphine)palladium(0) in DMF at 80–85° C. under an elevated argon pressure.

A nitrile of the formula (IX) may be deprotected to provide a nitrile of the formula (X) under conventional conditions. For example, where $R^{17}$ is tetrahydro-2H-pyran-2-yl, the deprotection may be carried out in the presence of a suitable acid as hydrochloric acid, trifluoroacetic acid, sulphuric acid, trichloroacetic acid, phosphoric acid, p-toluenesulfonic acid, benzenesulphonic acid, methanesulphonic acid or camphorsulphonic acid, and in a suitable solvent such as a $C_1$–$C_4$ alkanol that may optionally contain water, preferably at an elevated temperature such as the reflux temperature of the solvent. The pH may be adjusted to between pH8 and pH11 in the work-up procedure with an aqueous base such as sodium hydroxide, potassium hydroxide, sodium carbonate or potassium carbonate to generate the free base of the compound of the formula (X). Preferred conditions are using 2M aqueous hydrochloric acid in ethanol at room temperature or using trifluoroacetic acid in aqueous isopropanol under reflux conditions, followed by adjustment of the pH in the work-up to from pH 9–10.5 with aqueous sodium hydroxide solution.

A nitrile of the formula (X) may be converted to an ester of the formula (XII) by reaction with a sodium or potassium $C_1$–$C_4$ alkoxide in a corresponding $C_1$–$C_4$ alkanol solvent, optionally at an elevated temperature, and including an acid treatment during the work-up. Preferably, the reaction is carried out using sodium methoxide in methanol at the reflux temperature, with treatment with aqueous hydrochloric acid during the work-up.

Alternatively, an ester of the formula (XII) may be prepared by carbonylation of a compound of the formula (VI) with a compound of the formula:

$R^{18}OH$ using carbon monoxide, optionally under pressure, together with a suitable palladium catalyst in the presence of a suitable base, e.g. a tertiary amine base, and optionally at an elevated temperature, to provide a compound of the formula:

(VIA)

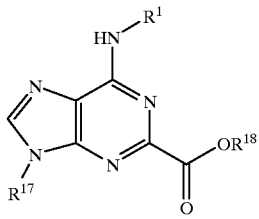

Typically, a catalytic quantity of palladium (II) acetate together with a suitable ligand such as 1,1'-bis(diphenylphosphino)ferrocene, triphenyl phosphine, tri-o-tolyl phosphine or BINAP ((R)- or (S)- or racemic-2,2'-bis(diphenylphosphino)-1,1'-binaphthyl), a suitable alcohol of the formula $R^{18}OH$, e.g. methanol, ethanol, 1-propanol, isopropanol, or 1-butanol (employed as the solvent also) and a base such as a triethylamine, Hunigs base (ethyldiisopropylamine), 4-methylmorpholine, sodium carbonate, sodium hydrogencarbonate, potassium carbonate or caesium carbonate, are used under carbon monoxide, optionally under 1–3000 kPa pressure in a sealed vessel at from 20 to 200° C. A compound of the formula (VIA) may be deprotected to provide a compound of the formula (XII) using suitable deprotection conditions such as those described for the conversion of a compound of the formula (IX) to a compound of the formula (X).

The ester of the formula (XII) may be coupled with a compound of the formula:

(XI)

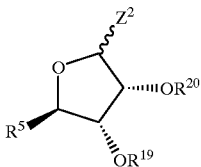

wherein $Z^2$ is a suitable leaving group such as acetoxy, benzoyloxy, methoxy or halo, e.g. chloro, and $R^{19}$ and $R^{20}$ are suitable protecting groups as previously defined, in the presence of a suitable acid or Lewis acid, e.g. trimethylsilyl trifluoromethanesulphonate, preferably using an excess thereof. The reaction can be performed using a compound of the formula (XI) in the form of a 2R- or 2S-diastereoisomer, or as an epimeric mixture thereof. The reaction is typically carried out in a suitable solvent, e.g. 1,2-dimethoxyethane, dichloromethane, acetonitrile, 1,1,1-trichloroethane or toluene, or a mixture thereof, preferably by pre-treating the compound of the formula (XII) in situ with a suitable silylating agent, e.g. trimethylsilyl trifluoromethanesulphonate, N,O-bis(trimethylsilyl)acetamide, trimethylsilyl chloride or hexamethyldisilazane, optionally in the presence of a tertiary amine base, e.g. N-methylmorpholine, before adding a compound of the formula (XI). Elevated temperatures may be used in the reaction. Preferred conditions involve treating a compound of the formula (XII) first with N,O-bis(trimethylsilyl)acetamide in 1,1,1-trichloroethane, heating the reaction under reflux, before treatment with a solution of a compound of the formula (XI) and trimethylsilyl trifluoromethanesulphonate in toluene and then heating at above 100° C. It will be appreciated that where a compound of the formula (XI) wherein $R^5$ is $CH_2OH$ is to be used, the hydroxyl group may be suitably protected for the purpose of this reaction (see later $R^{54}$ definition), which can then be deprotected in the subsequent transformation to provide a compound of the formula (XIV).

Deprotection of a compound of the formula (XIII) may be achieved using conventional conditions, e.g., where $R^{19}$ and $R^{20}$ are each acetyl or benzoyl, under basic conditions such as using sodium hydroxide, potassium hydroxide, lithium hydroxide, sodium carbonate, potassium carbonate or caesium carbonate in a solvent such as methanol, ethanol, isopropanol, 1,2-dimethoxyethane, THF, DMF, acetone, 2-butanone or 4-methyl-2-pentanone, optionally also in the presence of water, at a temperature of from 0 to 80° C. Alternatively either a tertiary amine base such as triethylamine, diisopropylethylamine or 4-methylmorpholine, in an alcohol solvent such as methanol, ethanol, isopropanol or 1-propanol may be used at a temperature of from 0 to 80° C., or a sodium or potassium $C_1$–$C_4$ alkoxide, e.g. sodium methoxide or ethoxide, in a corresponding $C_1$–$C_4$ alkanol, e.g. methanol or ethanol, may be used. Further, an amine such as ammonia, methylamine, ethylamine, dimethylamine and a suitable solvent such as methanol, ethanol, isopropanol, THF or dichloromethane can be used at a temperature of from 0 to 80° C. Preferably, sodium carbonate in methanol at room temperature is used.

An ester of the formula (XIV) may be converted to an amide of the formula (II) by reaction with a compound of the formula:

$$R^{15}NH-X-NHR^2, \qquad (XV)$$

optionally at an elevated temperature, optionally in an inert solvent such as 1,2-dimethoxyethane or 2-methoxyethyl ether and optionally under pressure.

Preferably, the reaction is carried out in the absence of solvent at a temperature of from 100–120° C. The skilled person will appreciate that to achieve the desired regioselectivity, a suitable protecting group (e.g. trifluoroacetyl) may optionally be used for this reaction located on a chosen N atom of a compound of the formula (XV), and the protected intermediate prepared subsequently deprotected.

A compound of the formula (II) may also be prepared by aminocarbonylation reaction of a compound of the formula (XVII) with a compound of the formula:

$$R^{15}NH-X-NHR \qquad (XV)$$

by a similar procedure to that described for the conversion of a compound of the formula (XVII) to a compound of the formula (I) below. The skilled person will appreciate that to achieve the desired regioselectivity, a suitable protecting group (e.g. trifluoroacetyl) may optionally be used for this reaction located on a chosen N atom of a compound of the formula (XV)), and the protected intermediate prepared subsequently deprotected.

A compound of the formula (XI) or (XV) may be prepared by conventional procedures.

2. The compounds of the formula (I) wherein Y is CO may be prepared by aminocarbonylation reaction of a compound of the formula:

(XVII)

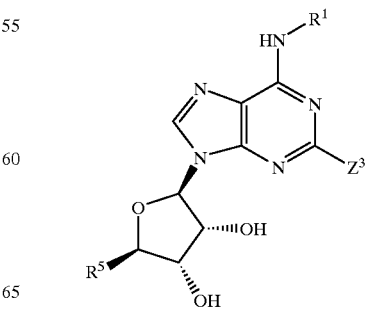

wherein $Z^3$ is a suitable leaving group such as bromo, iodo, —Sn($C_1$–$C_{12}$ alkyl)$_3$ or $CF_3SO_2O$—, preferably iodo, with a compound of the formula:

$$R^{15}NH—X—NR^2—Y—NR^3R^4 \qquad (XVIII)$$

in the presence of carbon monoxide and a suitable coupling catalyst (it will be appreciated that this route may also be used for compounds of the formula (I) where Y is other than CO). Preferably, the catalyst is a palladium (II) catalyst, more preferably 1,1'-bis(diphenylphosphino) ferrocenedichloropalladium (II) (optionally as a 1:1 complex with dichloromethane). Alternatively, palladium (II) acetate may be used in the presence of a suitable ligand such as 1,1'-bis(diphenylphosphino)ferrocene, triphenylphosphine, tri(o-tolyl)phosphine or (R)-, (S)- or racemic 2,2'-bis(diphenylphosphino)-1,1'-binaphthyl.

In a typical procedure the reaction is carried out in a sealed vessel in the presence of carbon monoxide at an elevated pressure, e.g. about 345 kPa (50 psi), at an elevated temperature, e.g. about 60° C., and in a suitable solvent, e.g. tetrahydrofuran, methanol or ethanol. Optionally, a suitable organic base may be present such as tertiary amine, e.g. triethylamine, N-ethyldiisopropylamine or 4-methylmorpholine.

The intermediates of the formula (XVII) can be prepared as shown in Scheme 2.

Scheme 2

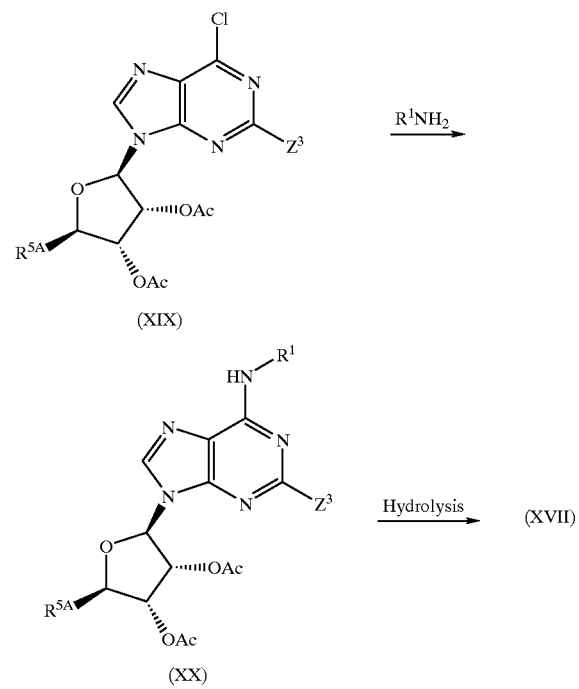

wherein, $R^{5A}$ is as defined hereafter, $Z^3$ is as previously defined for a compound of the formula (XVII) and "Ac" is acetyl (although it will be appreciated that alternative suitable protecting groups as exemplified herein may be used in this transformation).

In a typical procedure a compound of the formula (XIX) is reacted with an amine of the formula:

$$R^1NH_2 \qquad (XVI)$$

in the presence of a suitable acid acceptor, e.g. triethylamine, and in a suitable solvent, e.g. acetonitrile, at an elevated temperature, if necessary. The product of the formula (XX) obtained can be deprotected by hydrolysis to provide a compound of the formula (XVII) by a conventional procedure such as by using a suitable inorganic base, e.g. sodium carbonate, sodium hydroxide, potassium hydroxide, lithium hydroxide, sodium carbonate, potassium carbonate or caesium carbonate, and in a suitable solvent, e.g. methanol, ethanol, isopropanol, 1,2-dimethoxyethane, tetrahydrofuran, dimethylformamide, acetone, 2-butanone or 4-methyl-2-pentanone, optionally under aqueous conditions, at from 0° C. to the reflux temperature of the solvent, e.g. room temperature. Alternatively, the deprotection can be carried out using a suitable amine base such as triethylamine, diisopropylethylamine, 4-methylmorpholine, ammonia, methylamine, ethylamine or dimethylamine in a suitable solvent such as methanol, ethanol, n-propanol, isopropanol, tetrahydrofuran or dichloromethane at from 0° C. to the reflux temperature of the solvent.

An intermediate of the formula (XIX) can be prepared by a conventional procedure.

An intermediate of the formula (XVIII) may be prepared by reacting a compound of the formula:

$$R^{15}NH—X—NHR^2 \qquad (XV)$$

with a compound of the formula:

$$R^3R^4NCOZ^1 \qquad (III)$$

under similar conditions to those previously described for the conversion of compounds of the formulae (II) and (III) to a compound of the formula (I). The skilled person will appreciate that to achieve the desired regioselectivity, a suitable protecting group (e.g. trifluoroacetyl) may optionally be used for this reaction located on a chosen N atom of a compound of the formula (XV) and the protected intermediate prepared subsequently deprotected.

3. A compound of the formula (I) wherein Y is CO may be prepared by deprotection of a compound of the formula:

(XXI)

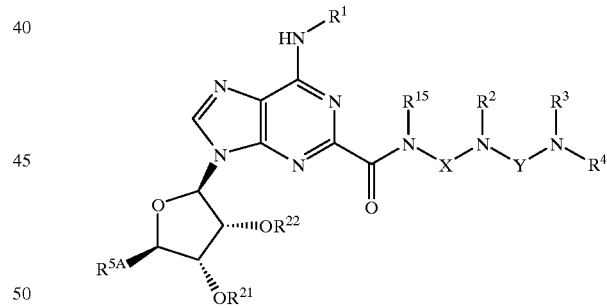

wherein $R^{21}$ and $R^{22}$ are either each a suitable protecting group such as acetyl or benzoyl, or, taken together, are a suitable protecting group such as $C_1$–$C_6$ alkylene optionally substituted by phenyl, e.g. 1,1-dimethylmethylene or phenylmethylene, $R^{5A}$ is $CH_2OH$, $CH_2OR^{23}$ or $CONR^{14}R^{14}$ and $R^{23}$ is a suitable protecting group such as acetyl or benzoyl (it will be appreciated that this route may also be used for compounds of the formula (I) where Y is other than CO).

Conventional deprotection conditions may be used and will depend on the nature of the protecting groups $R^{21}$, $R^{22}$ and $R^{23}$ to be removed. Further, the skilled person will realise that the protecting groups $R^{21}$, $R^{22}$ and $R^{23}$ may be removed all together, separately or in any combination to provide a compound of the formula (I). For example, where $R^{5A}$ is $CH_2OR^{23}$, either $R^{21}$ and $R^{22}$ may first be deprotected followed then by $R^{23}$, or vice-versa. In a typical procedure where $R^{21}$, $R^{22}$ and $R^{23}$ are each acetyl, the deprotection is achieved using a suitable inorganic base, e.g. sodium carbonate, sodium hydroxide, potassium hydroxide, lithium hydroxide, sodium carbonate, potassium carbonate or caesium carbonate, and in a suitable solvent, e.g. methanol, ethanol, isopropanol, 1,2-dimethoxyethane, tetrahydrofuran, dimethylformamide, acetone, 2-butanone or 4-methyl-2-pentanone, optionally under aqueous conditions, at from 0° C. to the reflux temperature of the solvent, e.g. room temperature. Alternatively, the deprotection can be carried out using a suitable amine base such as triethylamine, diisopropylethylamine, 4-methylmorpholine, ammonia, methylamine, ethylamine or dimethylamine in a suitable solvent such as methanol, ethanol, n-propanol, isopropanol, tetrahydrofuran or dichloromethane at from 0° C. to the reflux temperature of the solvent, or using a sodium or potassium $C_1$–$C_4$ alkoxide, e.g. sodium methoxide or ethoxide, in a corresponding $C_1$–$C_4$ alkanol, e.g. methanol or ethanol.

In a typical procedure, where $R^{21}$ and $R^{22}$ taken together are 1,1-dimethylmethylene, a compound of the formula (XXI) may be deprotected by treatment with a suitable acid such as hydrochloric acid, trifluoroacetic acid, sulphuric acid, phosphoric acid, pyridinium p-toluenesulphonate, p-toluenesulphonic acid, benzenesulphonic acid, methanesulphonic acid, acetic acid or formic acid, or a mixture thereof, or an acidic ion-exchange resin, optionally in the presence of a suitable solvent, e.g. ethanol, and optionally under aqueous conditions. The reaction may be carried out at an elevated temperature such as at the reflux temperature of the solvent.

Deprotection of a compound of the formula (XXI) to provide a compound of the formula (I) may also be accomplished in situ following the conversion of a compound of the formula (XXII) to a compound of the formula (XXI) as described below. Here, where $R^{21}$, $R^{22}$ and $R^{23}$ are each acetyl, the deprotection method using inorganic base is preferred, e.g. the reaction mixture containing a compound of the formula (XXI) is treated with aqueous sodium hydroxide solution in 1,2-dimethoxyethane at from 5–20° C.

A compound of the formula (XXI) may be prepared by coupling a compound of the formula:

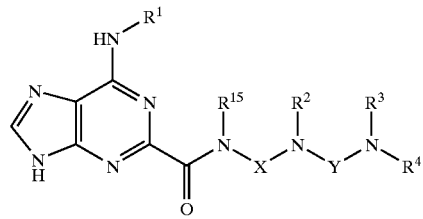

(XXII)

with a compound of the formula:

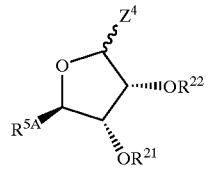

(XXIII)

wherein $Z^4$ is a suitable leaving group such as acetoxy, benzoyloxy, methoxy or halo, e.g. chloro, under similar conditions to those previously described for the conversion of a compound of the formula (XII) to (XIII).

A compound of the formula (XXII) may be prepared using conventional procedures as illustrated in Scheme 3. Such methods may be adapted from those previously described herein.

Scheme 3

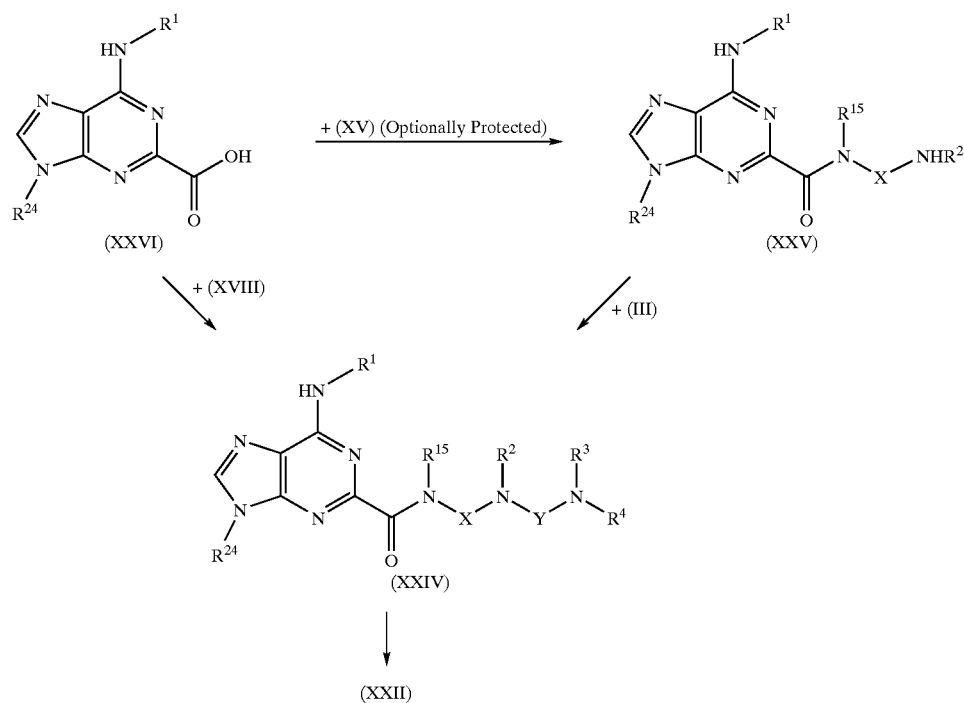

wherein $R^{24}$ is a suitable protecting group such as tetrahydro-2H-pyran-2-yl.

An acid of the formula (XXVI) may be prepared using conventional procedures, e.g. by basic hydrolysis of a compound of the formula (IX) such as by using aqueous sodium hydroxide solution followed by acidification in the work-up.

A compound of the formula (XXIII) may be prepared by conventional procedures.

A compound of the formula (XXI) where $R^{5A}$ is $CONR^{14}R^{14}$ may also be prepared as shown in Scheme 4.

Scheme 4

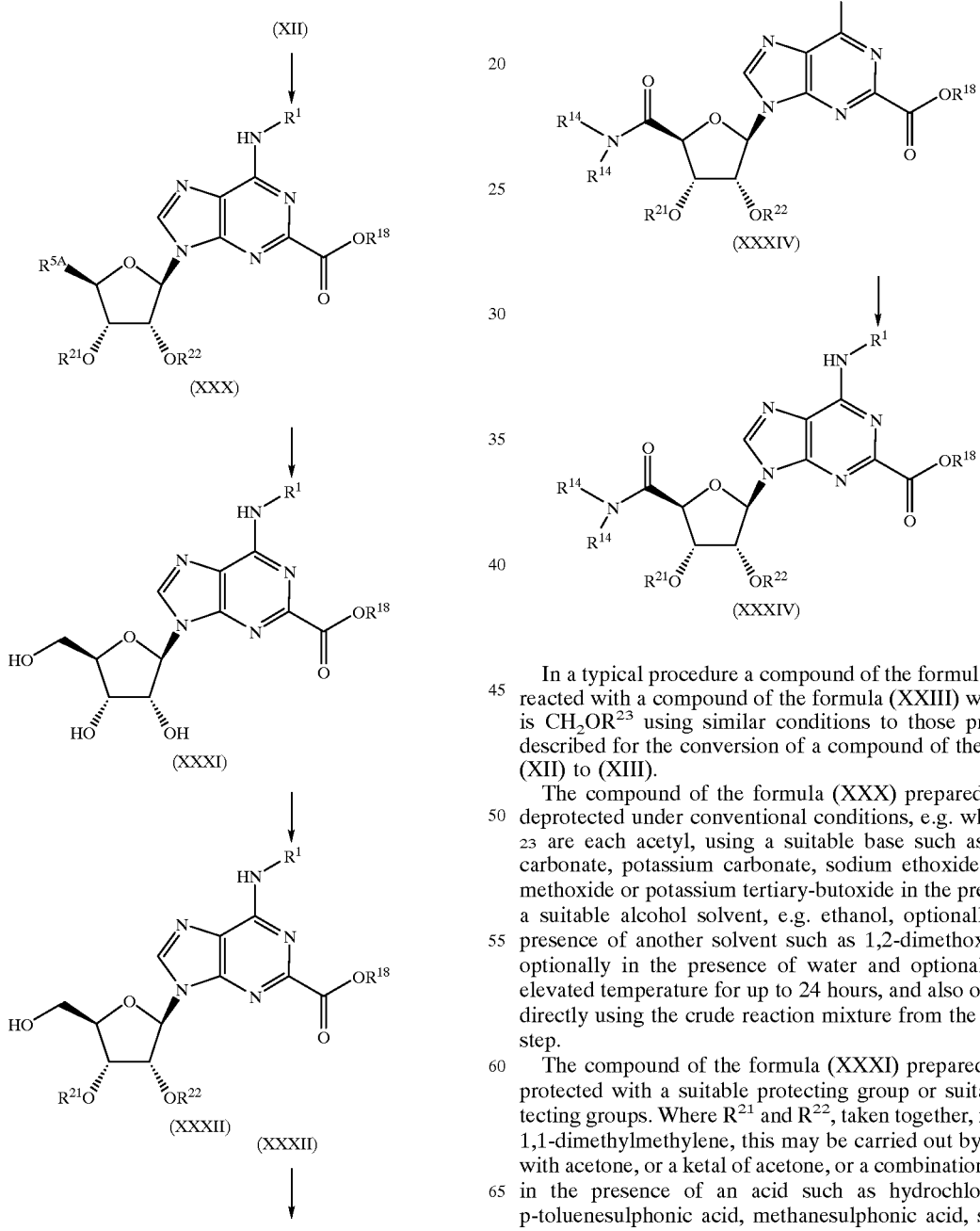

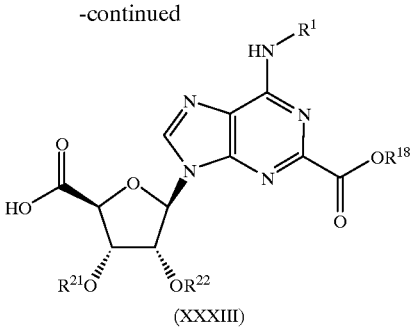

In a typical procedure a compound of the formula (XII) is reacted with a compound of the formula (XXIII) where $R^{5A}$ is $CH_2OR^{23}$ using similar conditions to those previously described for the conversion of a compound of the formula (XII) to (XIII).

The compound of the formula (XXX) prepared may be deprotected under conventional conditions, e.g. where $R^{21-23}$ are each acetyl, using a suitable base such as sodium carbonate, potassium carbonate, sodium ethoxide, sodium methoxide or potassium tertiary-butoxide in the presence of a suitable alcohol solvent, e.g. ethanol, optionally in the presence of another solvent such as 1,2-dimethoxyethane, optionally in the presence of water and optionally at an elevated temperature for up to 24 hours, and also optionally directly using the crude reaction mixture from the previous step.

The compound of the formula (XXXI) prepared may be protected with a suitable protecting group or suitable protecting groups. Where $R^{21}$ and $R^{22}$, taken together, represent 1,1-dimethylmethylene, this may be carried out by reaction with acetone, or a ketal of acetone, or a combination of both, in the presence of an acid such as hydrochloric acid, p-toluenesulphonic acid, methanesulphonic acid, sulphuric acid, phosphoric acid or trifluoroacetic acid, in a solvent such as acetone, toluene, dichoromethane or tetrahydrofuran, optionally at an elevated temperature. Preferably, the reaction is carried out using acetone and 2,2-dimethoxypropane in the presence of sulphuric acid.

Alternatively, a compound of the formula (XXX) may be converted directly to a compound of the formula (XXXII) by selective enzymatic hydrolysis, e.g. using a suitable lipase enzyme.

The compound of the formula (XXXII) prepared may be oxidised to a carboxylic acid of the formula (XXXIII) in either one step by treatment with a suitable oxidising agent in a suitable solvent or in two steps by treatment first with a suitable oxidising agent in a suitable solvent to generate the corresponding aldehyde and then subsequent treatment with a suitable oxidising agent in a suitable solvent. Typical single step conditions include treatment of the primary alcohol with an oxidising agent such as chromic acid, sodium periodate, chromium trioxide, potassium permanganate, sodium chlorite, sodium hypochlorite or oxygen, in a suitable solvent such as acetonitrile, dichloromethane, toluene or ethyl acetate, optionally in the presence of an appropriate catalyst such as ruthenium trioxide, ruthenium chloride, 2,2,6,6-tetramethylpiperidinyl-1-oxy free radical or platinum, optionally in the presence of a catalyst such as sodium hypochlorite, sodium bromide or potassium bromide, optionally in the presence of water, optionally in the presence of a phase transfer catalyst such as tetra-butylammonium bromide, benzyl triethylammonium chloride or tetra-butyl ammonium chloride, optionally in the presence of an inorganic base such as sodium carbonate, sodium hydrogen carbonate, potassium carbonate or sodium hydroxide, and optionally in the presence of additional additives such as sodium chloride. Suitable two step conditions include initial treatment with an oxidising agent such as the Swern reagent, tetrapropylammonium perruthenate, pyridinum dichromate, pyridinium chlorochromate, sulphur trioxide-pyridine complex or 1,1, 1-triacetoxy-1,1-dihydro-1,2-benziodoxol-3(1H)—one in a suitable solvent, and optionally in the presence of a an additional oxidant such as N-methylmorpholine-N-oxide, and then treatment of the intermediate aldehyde with another suitable oxidant such as such as chromic acid, sodium periodate, chromium trioxide, potassium permanganate, sodium chlorite, sodium hypochlorite or oxygen, in a suitable solvent such as acetonitrile, dichloromethane, toluene or ethyl acetate, optionally in the presence of an appropriate catalyst such as ruthenium trioxide, ruthenium chloride, 2,2,6,6-tetramethylpiperidinyl-1-oxy free radical or platinum, optionally in the presence of an additional catalyst such as sodium hypochlorite, sodium bromide or potassium bromide, optionally in the presence of water, optionally in the presence of a phase transfer catalyst such as tetra-butylammonium bromide, benzyl triethylammonium chloride or tetra-butyl ammonium chloride, optionally in the presence of an inorganic base such as sodium carbonate, sodium hydrogen carbonate, potassium carbonate or sodium hydroxide, and optionally in the presence of additional additives such as sodium chloride. Preferred conditions include treatment of the alcohol of the formula (XXXII) with a catalytic amount of 2,2,6,6-tetramethylpiperidinyl-1-oxy free radical in acetonitrile, in the presence of water and sodium dihydrogen phosphate, followed by addition of aqueous sodium hypochlorite (catalytic amount) and aqueous sodium chlorite at an elevated temperature. Alternatively, the alcohol of the formula (XXXII) is treated with 2,2,6,6-tetramethylpiperidinyl-1-oxy free radical (catalytic amount) and sodium hypochlorite in dichloromethane in the presence of water, sodium bicarbonate and a catalytic amount of tetrabutylammonium bromide.

The carboxylic acid of the formula (XXXIII) prepared may be converted to an amide of the formula (XXXIV) using conventional coupling conditions such as by activating the acid using a suitable activating agent, optionally in the presence of a catalyst, and then treating with an excess of the amine of the formula:

$HNR^{14}R^{14}$ in a suitable solvent. Typically, the reaction is carried out by treatment of the acid with an activating agent such as N'N'-carbonyldiimidazole, thionyl chloride, oxalyl chloride or phosphorus oxychloride in a solvent such as THF, DMF, ethyl acetate, acetonitrile, toluene, acetone or dichloromethane at a temperature of from 0 to 100° C. for 1–20 hours, followed by addition of the amine or an acid addition salt thereof, optionally in the presence of a tertiary amine acid acceptor such as triethylamine, ethyldiisopropylamine or N-methylmorpholine, at from 0 to 100° C. Alternatively, the acid is reacted with 1-(3-dimethylaminopropyl)-3-ethylcarbodiimide hydrochloride or N,N'-dicyclohexylcarbodiimide then 1-hydroxy-7-azabenzotriazole or 1-hydroxybenzotriazole hydrate, followed by the amine in the presence of an excess of 4-methylmorpholine, triethylamine or ethyldiisopropylamine in THF, DMF, ethyl acetate, acetonitrile, toluene, acetone or dichloromethane, at room temperature. The reaction can also be carried out by reacting the acid with benzotriazol-1-yloxytris(pyrrolidino)phosphonium hexafluorophosphate, bromo-tris-pyrrolidino-phosphonium hexafluorophosphate or Mukalyama's reagent (2-chloro-1-methylpyridinium iodide) and the amine in the presence of 4-methylmorpholine, triethylamine or ethyldiisopropylamine in THF, DMF, dichloromethane or ethyl acetate at room temperature. Preferably the reaction is carried out by initial treatment of the acid with N'N'-carbonyldiimidazole in ethyl acetate, followed by addition of the amine, in THF.

The compound of the formula (XXXIV) prepared may be hydrolysed to provide a carboxylic acid of the formula (XXXV) under conventional ester hydrolysis conditions such as by using an alkali metal base in a suitable solvent in the presence of water, optionally at an elevated temperature, followed by treatment with acid to generate the carboxylic acid. In a typical reaction, the reaction is carried out using lithium hydroxide, sodium hydroxide or potassium hydroxide in a solvent such as aqueous ethanol, methanol, isopropanol, butanol, industrial methylated spirits, tetrahydrofuran, DMF, 1,2-dimethoxyethane at from 0 to 100° C. Preferably, the reaction is carried out using sodium hydroxide in a mixture of methanol and water at 20–65° C.

The acid of the formula (XXXV) prepared may be converted to an amide of the formula (XXI) using conventional coupling conditions such as by activating the acid with a suitable activating agent, optionally in the presence of a catalyst, and then treating with an excess of the amine of the formula:

$R^{15}NH-X-NR^2-Y-NR^3R^4$ (XVIII)

in a suitable solvent. In a typical procedure the acid is treated with an activating agent such as N'N'-carbonyldiimidazole, thionyl chloride, oxalyl chloride or phosphorus oxychloride in a solvent such as THF, DMF, ethyl acetate, acetonitrile, toluene, acetone or dichloromethane at from 0 to 100° C., followed by addition of the amine or an acid addition salt thereof, optionally in the presence of a tertiary amine such as triethylamine, ethyldiisopropylamine or N-methylmorpholine, at from 0 to 100° C. Alternatively, the acid is reacted with 1-(3-dimethylaminopropyl)-3-ethylcarbodiimide hydrochloride or N,N'-dicyclohexylcarbodiimide then 1-hydroxy-7-azabenzotriazole or 1-hydroxybenzotriazole hydrate, followed by the amine in the presence of an excess of 4-methylmorpholine, triethylamine or ethyldiisopropylamine in THF, DMF, ethyl acetate, acetonitrile, toluene, acetone or dichloromethane, at room temperature. The reaction can also be carried out by reacting the acid with benzotriazol-1-yloxytris(pyrrolidino)phosphonium hexafluorophosphate, bromo-tris-pyrrolidino-phosphonium hexafluorophosphate or Mukaiyama's reagent (2-chloro-1-methylpyridinium iodide) and the amine in the presence of 4-methylmorpholine, triethylamine or ethyldiisopropylamine in THF, DMF, dichioromethane or ethyl acetate at room temperature. Preferably, the reaction is carried out by initial treatment of the acid with N'N'-carbonyldiimidazole in dichloromethane, followed by addition of the amine, optionally in the form of a suitable acid addition salt such as a hydrochloride salt, and in the presence of an acid acceptor such as triethylamine, at room temperature.

A compound of the formula (XXXIII) may also be prepared as shown in Scheme 5.

Scheme 5

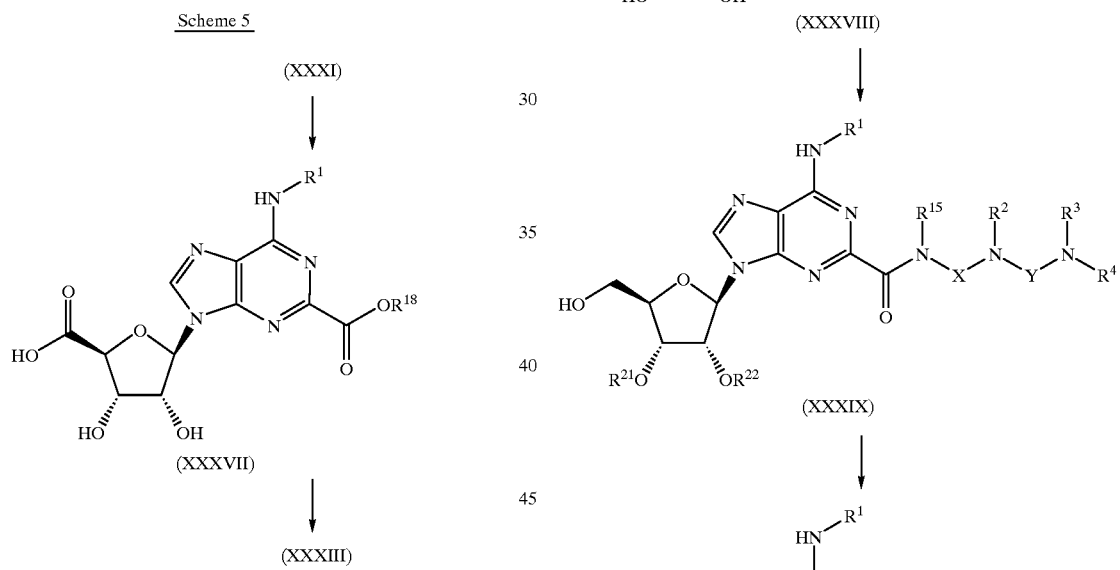

A triol of the formula (XXXI) may be selectively oxidised to provide a diol of the formula (XXXVII), typically using a selective oxidising agent such as sodium hypochlorite in the presence of a catalytic amount of 2,2,6,6-tetramethylpiperidinyl-1-oxy free radical and bromide ion (provided as sodium bromide, potassium bromide or tetraalkylammonium bromide), or using oxygen in the presence of a platinum catalyst, in a suitable solvent such as water, acetonitrile, dichloromethane, toluene or ethyl acetate or in a mixture of an organic solvent and water together with a phase transfer catalyst such as tetrabutylammonium bromide, tetrabutylammonium chloride or benzyltriethylammonium chloride The diol of the formula (XXXVII) may be protected using a suitable protecting group or suitable protecting groups. Where the protecting group is 1,1-dimethylmethylene this may be achieved by reaction with acetone, or a derivative of acetone, in the presence of a acidic reagent. In a typical reaction the diol is reacted with acetone, or a ketal of acetone such as 2,2-dimethoxypropane, or a combination of both, in the presence of an acid such as hydrochloric acid, p-toluenesulphonic acid, methanesulphonic acid, sulphuric acid, phosphoric acid or trifluoroacetic acid and in a solvent such as acetone, toluene, dichoromethane or tetrahydrofuran, optionally at an elevated temperature.

A compound of the formula (XXI) where $R^{5A}$ is $CONR^{14}R^{14}$ may also be prepared as shown in Scheme 6.

Scheme 6

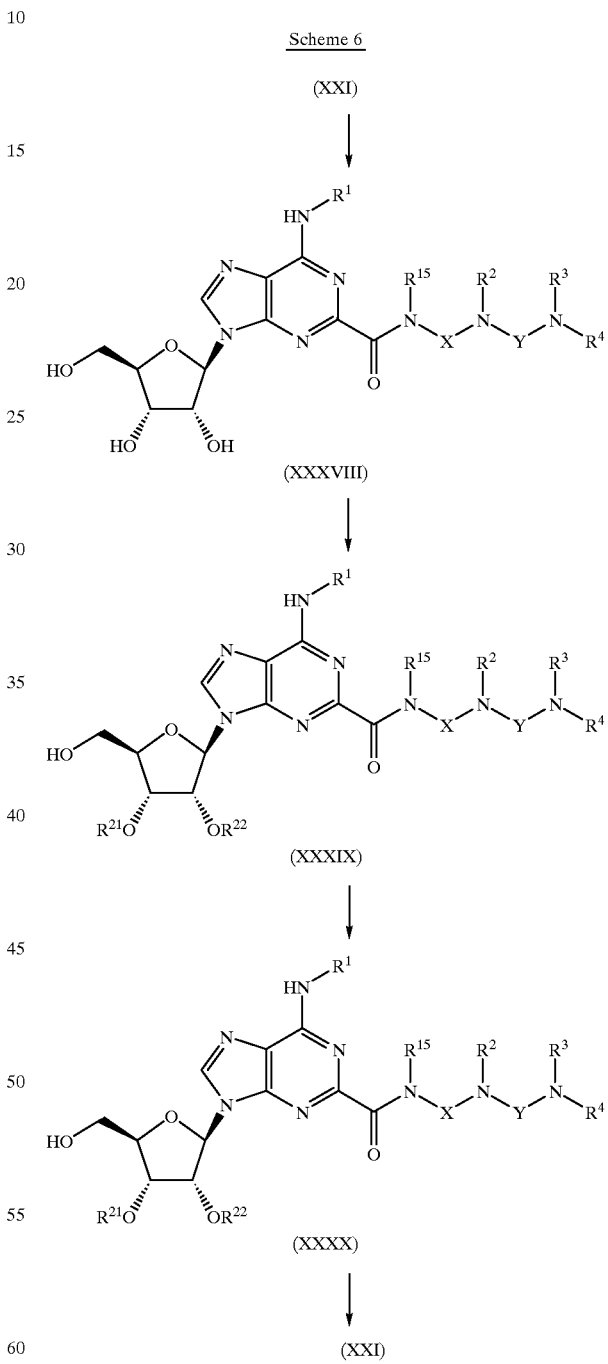

In a typical procedure, a compound of the formula (XXI) where $R^{5A}$ is $CH_2OR^{23}$ where $R^{21-23}$ are suitable protecting groups such as acetyl is deprotected under conventional conditions such as by treatment with a base such as sodium hydroxide, potassium hydroxide, sodium carbonate, potassium carbonate, sodium ethoxide, sodium methoxide or potassium tertiary-butoxide in a suitable alcohol solvent, optionally in the presence of another solvent such as 1,2-dimethoxyethane, optionally in the presence of water and optionally at an elevated temperature.

The compound of the formula (XXXVIII) prepared may be selectively protected under conventional conditions. Where $R^{21}$ and $R^{22}$, taken together, represent 1,1-dimethylmethylene, this may be achieved by reacting the triol with acetone, or a ketal of acetone such as 2,2-dimethoxyprop)ane, or a combination of both, in the presence of an acid such as hydrochloric acid, p-toluenesulphonic acid, methanesulphonic acid, sulphuric acid, phosphoric acid or trifluoroacetic:acid and in a solvent such as acetone, toluene, dichoromethane or tetrahydrofuran, optionally at elevated temperature Alternatively, a compound of the formula (XXI) may be converted directly to a compound of the formula (XXXIX) by selective enzymatic hydrolysis, e.g. using a suitable lipase enzyme.

The alcohol of the formula (XXXIX) may be oxidised to an acid of the formula (XXXX) using similar conditions to those previously described for the conversion of a compound of the formula (XXXII) to (XXXIII).

The acid of the Formula (XXXX) may be converted to an amide of the formula (XXI) using similar conditions to those previously described for the conversion of a compound of the formula (XXXIII) to (XXXIV).

4. A compound of the formula (I) wherein Y is CS may be prepared by the reaction of a compound of the formula:

$Z^5CS.Z^6$, wherein $Z^5$ and $Z^6$ are each a suitable leaving group, with a compound of the formula (II), followed by reaction of the intermediate of the formula:

(XXIVA)

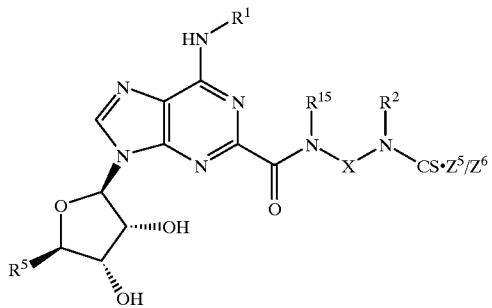

obtained with an amine of the formula:

$R^3R^4NH.$ $Z^5$ and $Z^6$ may be the same or different and are typically selected from —S(C$_1$–C$_6$ alkyl) or 1H-imidazol-1-yl.

5. A compound of the formula (I) wherein Y is SO$_2$ may be prepared by reaction of a compound of the formula:

$R^3R^4NSO_2Z^7$ (XXVII)

wherein $Z^7$ is a leaving group, with compound of formula (II), optionally in the presence of an acid acceptor. A compound of formula (XXVII) can be prepared by conventional activation procedures from a compound of the formula:

$R^3R^4NSO_3H$ (XXVIII), e.g. using PCl$_5$ where $Z^7$ is Cl. A compound of the formula (XXVIII) may be prepared by reacting chlorosulphonic acid with an amine of the formula:

$R^3R^4NH.$

6. A compound of the formula (I) wherein Y is C=N(CN) may be prepared by the reaction of a compound of the formula:

$Z^8C=N(CN).Z^9$ (XXIX)

wherein $Z^8$ and $Z^9$ are each a leaving group, with a compound of the formula (II), followed by reaction of the intermediate of the formula:

(XXIVB)

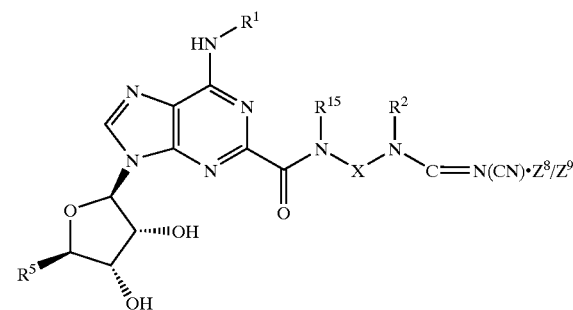

obtained with an amine of the formula:

$R^3R^4NH.$ $Z^8$ and $Z^9$ may be the same or different, e.g. —S(C$_1$–C$_6$ alkyl), preferably —SCH$_3$. In a typical procedure, a solution of a compound of the formula (II) in a suitable solvent, such as ethanol, is treated with dimethylcyanothioimidocarbamate, preferably at room temperature. When the reaction is substantially complete an amine of the formula $R^3R^4NH$ is added and the reaction mixture is heated, preferably at reflux, to provide the required product.

7. Any compound of the formula (I) may be prepared by reaction of an ester of the formula (XIV) with an amine of the formula:

$R^{15}NH—X—NR^2—Y—NR^3R^4,$ (XVIII)

optionally at an elevated temperature, optionally in an inert solvent such as 1,2-dimethoxyethane or 2-methoxyethyl ether and optionally under pressure.

Preferably, the reaction is carried out in the absence of solvent at a temperature of from 100–120° C.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the Examples and Preparations hereto. In particular, suitable protection and deprotection procedures are well-known in the art, e.g. as described in Greene et al, "Protective Groups in Organic Synthesis", Third Edition, John Wiley & Sons Ltd.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The anti-inflammatory properties of the compounds of the formula (I) are demonstrated by their ability to inhibit neutrophil function which indicates A2a receptor agonist activity. This is evaluated by determining the compound profile in an assay where superoxide production was measured from neutrophils activated by fMLP. Neutrophils were isolated from human peripheral blood using dextran sedimentation followed by centrifugation through Ficoll-Hypaque solution. Any contaminating erythrocytes in the granulocyte pellet were removed by lysis with ice-cold distilled water. Superoxide production from the neutrophils was induced by fMLP in the presence of a priming concentration of cytochalasin B. Adenosine deaminase was included in the assay to remove any endogenously produced adenosine that might suppress superoxide production. The effect of the compound on the fMLP-induced response was monitored colorometrically from the reduction of cytochrome C within the assay buffer. The potency of the compounds was assessed by the concentration giving 50% inhibition ($IC_{50}$) compared to the control response to fMLP.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the formula (I) may also be administered as fast-dispersing or fast-dissolving dosage forms or in the form of a high energy dispersion or as coated particles. Suitable formulations of the compounds of the formula (I) may be in coated or uncoated form, as desired.

Such solid pharmaceutical compositions, for example, tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, sodium stearyl fumarate, sodium lauryl sulphate, stearic acid, glyceryl behenate and talc may be included.

General Example

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
|---|---|
| Compound of the formula (I) or salt | 10.000* |
| Lactose | 64.125 |
| Starch | 21.375 |
| Croscarmellose Sodium | 3.000 |
| Magnesium Stearate | 1.500 |

*Quantity adjusted in accordance with drug activity.

The tablets can be manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or a high molecular weight polyethylene glycol. For aqueous suspensions and/or elixirs, the compounds of the formula (I) may be combined with various sweetening or flavouring agents, colouring matter or dyes, with emulsifying and/or suspending agents and with diluents such as water, ethanol, propylene glycol or glycerin, and combinations thereof.

The compounds of the formula (I) can also be administered parenterally, for example, intravenously, intraarterially, intraperitoneally, intrathecally, intraventricularly, intraurethrally, intrasternally, intracranially, intramuscularly or subcutaneously, or they may be administered by infusion or needleless injection techniques. For such parenteral administration, they are best used in the form of a sterile aqueous solution which may contain other substances, for example, a co-solvent and/or enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the formula (I) will usually be from 0.00001 to 100 mg/kg, preferably from 0.0001 to 100 mg/kg (in single or divided doses).

Thus tablets or capsules of the compound of the formula (I) may contain from 0 01 to 500 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The compounds of formula (I) can also be administered intranasally or by inhalation and are conveniently delivered in the form of a dry powder inhaler or an aerosol spray presentation from a pressurised container, pump, spray, atomiser (preferably an atomiser using electrohydrodynamics to produce a fine mist) or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide, a further perfluorinated hydrocarbon such as Perflubron (trade mark) or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol (optionally, aqueous ethanol) or a suitable agent for dispersing, solubilising or extending release and the propellant as the solvent, which may additionally contain a lubricant, e.g. sorbitan trioleate. Capsules, blisters and cartridges (made, for example, from gelatin or HPMC) for use in an inhaler or insufflator may be formulated to contain a powder mix of a compound of the formula (I), a suitable powder base such as lactose or starch and a performance modifier such as I-leucine, mannitol or magnesium stearate.

A suitable solution formulation for use in an atomiser using electrohydrodynamics to produce a fine mist may contain from 1 μg to 10 μmg of a compound of the formula (I) or a salt thereof and the actuation volume may vary from 1 to 100 μl. A typical formulation may comprise a compound of the formula (I) or salt thereof, propylene glycol, sterile water, ethanol and sodium chloride.

Aerosol or dry powder formulations are preferably arranged so that each metered dose or "puff" contains from 1 to 4000 µg of a compound of the formula (I) for delivery to the patient. The overall daily dose with an aerosol will be in the range of from 1 µg to 20 mg which may be administered in a single dose or, more usually, in divided doses throughout the day.

Alternatively, the compounds of the formula (I) can be administered in the form of a suppository or pessary, or they may be applied topically in the form of a lotion, solution, cream, ointment or dusting powder. The compounds of the formula (I) may also be dermally or transdermally administered, for example, by the use of a skin patch. They may also be administered by the pulmonary, vaginal or rectal routes.

For application topically to the skin, the compounds of the formula (I) can be formulated as a suitable ointment containing the active compound suspended or dissolved in, for example, a mixture with one or more of the following mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

It is to be appreciated that all references herein to treatment include curative, palliative and prophylactic treatment. Thus the invention provides:

(i) a compound of the formula (I) or a pharmaceutically acceptable salt or solvate thereof;

(ii) a process for the preparation of a compound of the formula (I) or a pharmaceutically acceptable salt or solvate thereof;

(iii) a pharmaceutical composition including a compound of the formula (I) or a pharmaceutically acceptable salt or solvate thereof, together with a pharmaceutically acceptable excipient, diluent or carrier;

(iv) a compound of the formula (I) or a pharmaceutically acceptable salt, solvate or composition thereof, for use as a medicament;

(v) the use of a compound of the formula (I) or of a pharmaceutically acceptable salt, solvate or composition thereof, for the manufacture of a medicament having A2a receptor agonist activity;

(vi) the use of a compound of the formula (I) or of a pharmaceutically acceptable salt, solvate or composition thereof, for the manufacture of an anti-inflammatory agent;

(vii) the use of a compound of the formula (I) or of a pharmaceutically acceptable salt, solvate or composition thereof, for the manufacture of a medicament for the treatment of a respiratory disease;

(viii) use as in (vii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(ix) the use of a compound of the formula (I) or of a pharmaceutically acceptable salt, solvate or composition thereof, for the manufacture of a medicament for the treatment of septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing;

(x) a method of treatment of a mammal, including a human being, with a A2a receptor agonist including treating said mammal with an effective amount of a compound of the formula (I) or with a pharmaceutically acceptable salt, solvate or composition thereof;

(xi) a method of treatment of a mammal, including a human being, to treat an inflammatory disease including treating said mammal with an effective amount of a compound of the formula (I) or with a pharmaceutically acceptable salt, solvate or composition thereof;

(xii) a method of treatment of a mammal, including a human being, to treat a respiratory disease including treating said mammal with an effective amount of a compound of the formula (I) or with a pharmaceutically acceptable salt, solvate or composition thereof;

(xiii) a method as in (xii) where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis;

(xiv) a method of treatment of a mammal, including a human being, to treat septic shock, male erectile dysfunction, male factor infertility, female factor infertility, hypertension, stroke, epilepsy, cerebral ischaemia, peripheral vascular disease, post-ischaemic reperfusion injury, diabetes, rheumatoid arthritis, multiple sclerosis, psoriasis, dermatitis, allergic dermatitis, eczema, ulcerative colitis, Crohns disease, inflammatory bowel disease, *Heliobacter pylori* gastritis, non-*Heliobacter pylori* gastritis, non-steroidal anti-inflammatory drug-induced damage to the gastrointestinal tract or a psychotic disorder, or for wound healing, including treating said mammal with an effective amount of a compound of the formula (I) or with a pharmaceutically acceptable salt, solvate or composition thereof; and (xv) certain novel intermediates disclosed herein.

In the Examples and Preparations that follow, "THF" means tetrahydrofuran, "DMSO" means dimethylsulphoxide and "TLC" means thin layer chromatography.

EXAMPLE 1

6-[(2,2-Diphenylethyl)amino]-9-{(2R,3R,4S,5S)-5-[(ethylamino)carbonyl]-3,4-dihydroxytetrahydro-2-furanyl}-N-{2-[({[2-(1-piperidinyl)ethyl]amino}carbonyl)amino]ethyl}-9H-purine-2-carboxamide

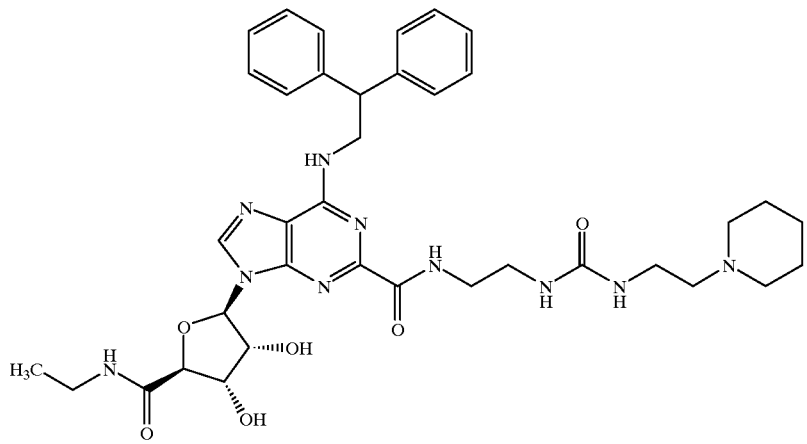

N-(2-Aminoethyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 10) (90 mg, 0.15 mmol) and N-[2-(1-piperidinyl)ethyl]-1H-imidazole-1-carboxamide (Preparation 18) (36 mg, 0.16 mmol) were dissolved in dichloromethane (3 ml). Toluene (4 ml) and isopropanol (1 ml) were added and the dichloromethane removed by evaporation at atmospheric pressure. The residual solution was heated under reflux for four hours. TLC analysis showed the reaction to be incomplete so further N-[2-(1-piperidinyl)ethyl]-1H-imidazole-1-carboxamide (25 mg, 0.11 mmol) was added and heating continued for four hours. The solvent was removed under reduced pressure and the residue purified by column chromatography on silica gel eluting with dichloromethane:methanol:concentrated aqueous ammonia (90:10:1, by volume). Product containing fractions were evaporated and the resulting solid triturated with diethyl ether, filtered and dried to afford the title compound as a white powder (60 mg)

$^1$H-NMR (400 MHz, CDCl$_3$) δ: 8.20 (1H, s), 7.35–7.20 (10H, m), 5.90 (1H, m), 4.90–460 (4H, m), 4.40 (2H, m), 3.60–3.00 (8H, m), 2.45–2.25 (6H, m), 1.60–1.40 (6H, m), 1.00 (3H, t).

LRMS (thermospray): m/z [MH$^+$] 729.

EXAMPLE 2

N-{2-[({[2-(Diisopropylamino)ethyl]amino]carbonyl)amino}ethyl-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

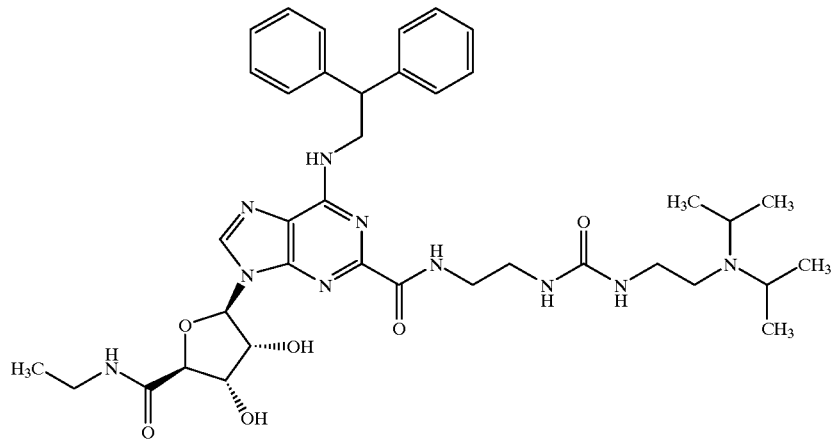

N-(2-Aminoethyl)-6-[(2,2-diphenylethyl)amino]-9-{(2R,3R,4S,5S)-5-[(ethylamino)carbonyl]-3,4-dihydroxytetrahydro-2-furanyl}-9H-imidazole-1-carboxamide (Preparation 10) (90 mg, 0.16 mmol) and N-[2-(diisopropylamino)ethyl]-1H-imidazole-1-carboxamide (Preparation 19) (40 mg, 0.17 mmol) were dissolved in dichloromethane (3 ml). Toluene (4 ml) and isopropanol (1 ml) were added and the dichloromethane removed by evaporation at atmospheric pressure. The residual solution was then heated under reflux for four hours. TLC analysis showed the reaction to be incomplete so further N-[2-(diisopropylamino)ethyl]-1H-imidazole-1-carboxamide (30 mg, 0.13 mmol) was added and heating continued for a further four hours. The solvent was removed under reduced pressure and the residue purified by column chromatography on silica gel eluting with dichloromethane:methanol:concentrated aqueous ammonia (90:10:1, by volume) to afford the title compound as a white solid (60 mg).

$^1$H-NMR (400 MHz, CDCl$_3$+CD$_3$OD) δ: 8.15 (1H, s), 7.30–7.10 (10H, m), 6.15 (1H, m), 4.70–4.50 (3H, m), 4.40–4.30 (3H, m), 3.60–3.10 (6H, m), 3.05–2.85 (4H, m), 2.45 (2H, m), 1.00–0.85 (15H, m).

LRMS (thermospray): m/z [MH$^+$] 745.

EXAMPLE 3

9-[(2R,3R,4S,5R)-3,4-Dihydroxy-5-(hydroxymethyl)tetrahydro-2-furanyl]-6-[(2,2-diphenylethyl)amino]-N-{2-[({[2-(1-piperidinyl)ethyl]amino}carbonyl)amino]ethyl}-9H-purine-2-carboxamide

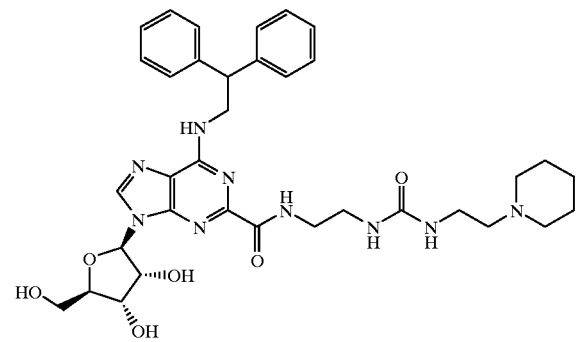

N-(2-Aminoethyl)-9-[(2R,3R,4S,5R)-3,4-dihydroxy-5-(hydroxymethyl)tetrahydro-2-furanyl]-6-[(2,2-diphenylethyl)amino]-9H-purine-2-carboxamide (Preparation 17) (90 mg, 0.17 mmol) and N-[2-1-piperidinyl)ethyl]-1H-imidazole-1-carboxamide (Preparation 18) (40 mg, 0.18 mmol) were dissolved in a mixture of toluene (4 ml) and isopropanol (1 ml) and the solution heated under reflux for four hours. The solvent was removed under reduced pressure and the residue purified by column chromatography on silica gel eluting with dichloromethane:methanol:concentrated aqueous ammonia (85:15:1.5, by volume). Product containing fractions were evaporated and the resulting solid triturated with diethyl ether, filtered and dried to afford the title compound as a white powder (85 mg).

$^1$H-NMR (400 MHz, CDCl$_3$+CD$_3$OD) δ: 7.95 (1H, s), 7.35–7.15 (10H, m), 5.85 (1H, m), 4.85 (1H, m), 4.40–4.20 (5H, m), 4.00 (1H, m), 3.80 (1H, m), 3.60 (1H, m), 3.50–3.30 (3H, m), 3.10 (2H, m), 2.35–2.15 (6H, m), 1.50–1.30 (6H, m).

LRMS (thermospray): m/z [MH$^+$] 688.

EXAMPLE 4

9-[(2R,3R,4S,5R)-3,4-Dihydroxy-5-hydroxymethyl)tetrahydro-2-furanyl]-N-{2-[({[2-(diisopropylamino)ethyl]amino}carbonyl)amino]ethyl}-6-[(2,2-diphenylethyl)amino]-9H-purine-2-carboxamide

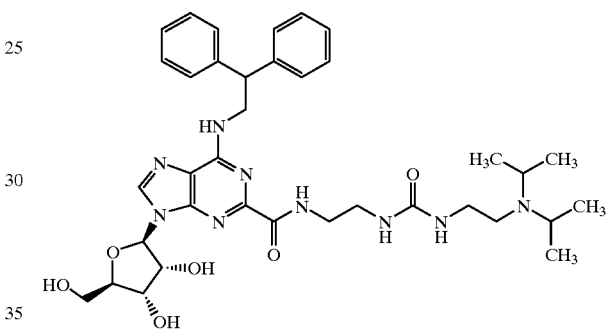

N-(2-Aminoethyl)-9-[(2R,3R,4S,5R)-3,4-dihydroxy-5-hydroxymethyl)tetrahydro-2-furanyl]-6-[(2,2-diphenylethyl)amino]-9H-purine-2-carboxamide (Preparation 17) (90 mg, 0.17 mmol) and N-[2-diisopropylamino)ethyl]-1H-imidazole-1-carboxamide (Preparation 19) (50 mg, 0 19 mmol) were dissolved in a mixture of toluene (4 ml) and isopropanol (1 ml) and the solution heated under reflux for four hours. The solvent was removed under reduced pressure and the residue purified by column chromatography on silica gel eluting with dichloromethane:methanol:concentrated aqueous ammonia (85:15:1.5, by volume). Product containing fractions were evaporated and the resulting solid triturated with diethyl ether, filtered and dried to afford the title compound as a white powder (85 mg).

$^1$H-NMR (400 MHz, CDCl$_3$+CD$_3$OD) δ: 8.00 (1H, s), 7.30–7.10 (10H, m), 5.85 (1H, m), 4.75 (1H, m), 4.40–4.20 (4H, m), 4.15 (1H, m), 3.95 (1H, m), 3.80 (1H, m), 3.60–3.30 (4H, m), 3.05–2 85 (4H, m), 2.45 (2H, m), 0.90 (12H, d).

LRMS (thermospray): m/z [MH$^+$] 704.

EXAMPLE 5
6-[(2,2-Diphenylethyl)amino]-9-{(2R,3R,4S,5S)-5-[(ethylamino)carbonyl]-3,4-dihydroxytetrahydro-2-furanyl}-N-{2-[({[2-(4-isopropyl-1-piperidinyl)ethyl]amino}carbonyl)amino]ethyl}-9H-purine-2-carboxamide

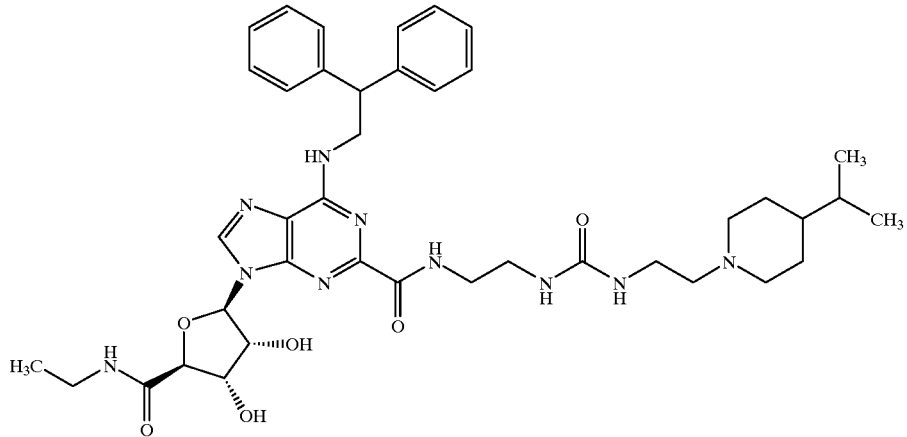

Prepared from N-(2-aminoethyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 10) and N-[2-4-isopropyl-1-piperidinyl)ethyl]-1H-imidazole-1-carboxamide (Preparation 22) by a similar method to Example 1.

$^1$H-NMR (400 MHz, CD$_3$OD/CDCl$_3$) δ: 8.10 (1H, s), 7.30–7.10 (10H, m), 5.95 (1H, d), 4.75 (1H, br s), 4.50–4.20 (5H, m), 3.50–3.40 (2H, m), 3.20 (1H, m), 3.10 (2H, m), 2.80 (2H, m), 2.25 (2H, m), 1.80 (2H, m), 1.55 (2H, m), 1.30 (1H, m), 1.10 (2H, m), 0.95 (3H, t), 0.90 (1H, m), 0.80 (6H, d).

LRMS (thermospray): m/z [MH$^+$] 772.

EXAMPLE 6
N-(2-{[({2-[Cycopentyl(isopropyl)amino]ethyl}amino)carbonyl]amino}ethyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide Prepared from N-(2-aminoethyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 10) and N-{2-[cyclopentyl(isopropyl)amino]ethyl}-1H-imidazole-1-carboxamide (Preparation 26) by a similar method to Example 1.

$^1$H-NMR (400 MHz, CD$_3$OD/CDCl$_3$) δ: 8.15 (1H, s), 7.35–7.15 (10H, m), 6.10 (1H, m), 4.70 (2H, m), 4.55 (1H, m), 4.40–4.30 (3H, m), 3.60–2.90 (10H, m), 2.60–2.40 (2H, m), 1.70–1.20 (8H, m), 1.00–0.90 (9H, m).

EXAMPLE 7
N-(2-{[({2-[Cyclohexyl(isopropyl)amino]ethyl}amino)carbonyl]amino}ethyl)-6-[(2,2-diphenylethyl)amino]-9-{(2R,3R,4S,5S)-5-[(ethylamino)carbonyl]-3,4-dihydroxytetrahydro-2-furanyl}-9H-purine-2carboxamide

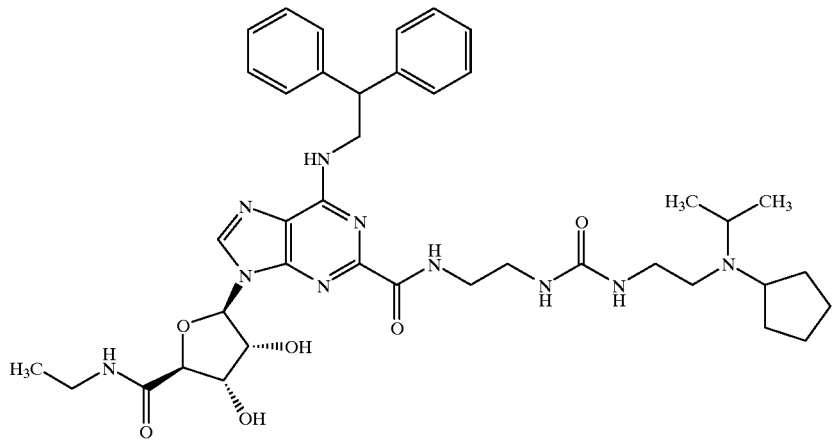

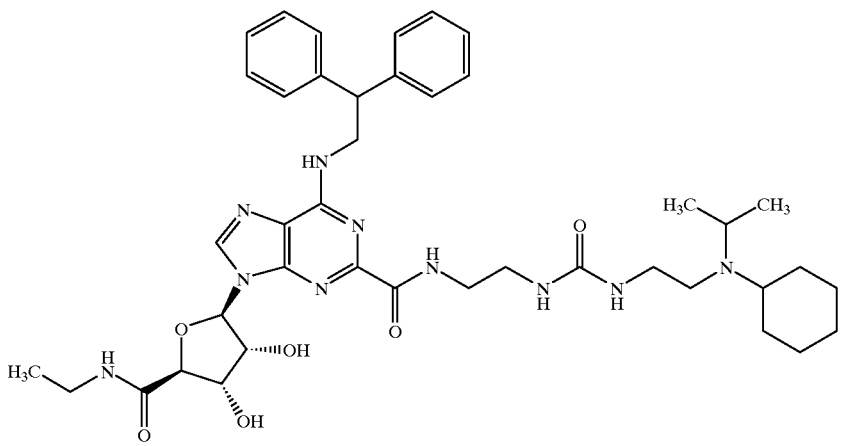

Prepared from N-(2-aminoethyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 10) and N-{2-[cyclohexyl(isopropyl)amino]ethyl}1H-imidazole-1-carboxamide (Preparation 29) by a similar method to Example 1.

$^1$H-NMR (400 MHz, CD$_3$OD/CDCl$_3$) δ: 8.10 (1H, s), 7.30–7.10 (10H, m), 6.05 (1H, m), 4.70–4.55 (2H, m), 4.45 (1H, m), 4.40–4.25 (3H, m), 3.60–2.90 (10H, m), 2.60–2.40 (3H, m), 1.75–1.60 (4H, m), 1.50 (1H, m), 1.20–1.05 (6H, m), 1.00–0.90 (9H, m).

LRMS (thermospray): m/z [MH$^+$] 786.

EXAMPLE 8

6-[(2,2-Diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide $^1$H-NMR (400 MHz, CD$_3$OD) δ: 8.40 (1H, m), 8.00 (1H, d), 8.05 (1H, d), 7.45 (1H, m), 7.40–7.30 (4H, m), 7.25–7.20 (4H, m), 7.10 (2H, m), 6.70 (1H, d), 6.55 (1H, m), 6.10 (1H, m), 4.50–4.35 (4H, m), 4.00 (2H, m), 3.65 (1H, m), 3.50 (2H, m), 3.4 (2H, m), 3.30 (1H, m), 3.25 (1H, m), 2.85 (2H, m), 1.80 (2H, m), 1.30 (2H, m), 1.00 (3H, m).

LRMS (thermospray): m/z [MH$^+$] 778.

EXAMPLES 9–27

The compounds of following tabulated Examples were prepared by a similar method to that of Example 1 using the appropriate amine and imidazolide starting materials.

Table 1 shows the compound structures and Table 2 the analytical data for each compound.

The term "n-Bu" in Table 1 means n-butyl.

The imidazolide starting material for Examples 13, 24 and 25 may be prepared as described in Monatsh. Chem., 88, 35 (1957).

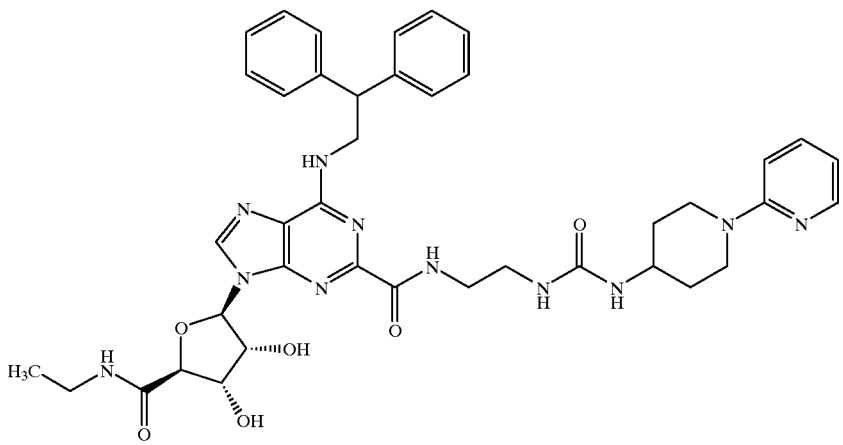

Prepared from N-(2-aminoethyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 10) and N-[1-(2-pyridinyl)-4-piperidinyl]-1H-imidazole-1-carboxamide (Preparation 30) by a similar method to Example 1.

The imidazolide starting material for Example 14 and 26 may be prepared as described in J. Chem. Soc. Perkin Trans. 1, 11, 1205 (1996)

The imidazolide starting material for Example 15 may be prepared as described in Justus Liebigs Ann. Chem. 648, 72 (1961).

TABLE 1

| Example No. | Compound |
|---|---|
| 9 | |
| 10 | |
| 11 | |

TABLE 1-continued

| Example No. | Compound |
|---|---|
| 12 | |
| 13 | |
| 14 | |

TABLE 1-continued
| Example No. | Compound |
|---|---|
| 15 | 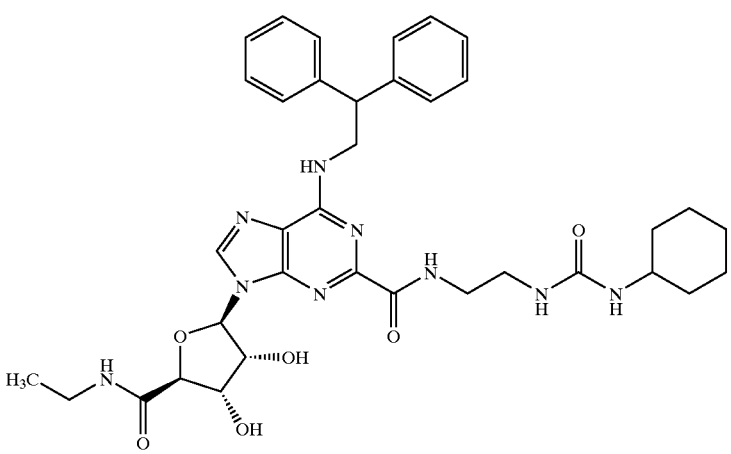 |
| 16 | 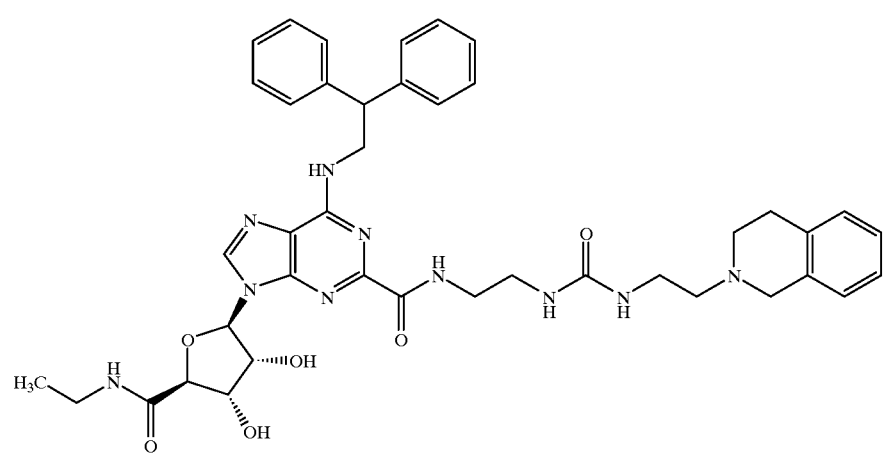 |
| 17 | 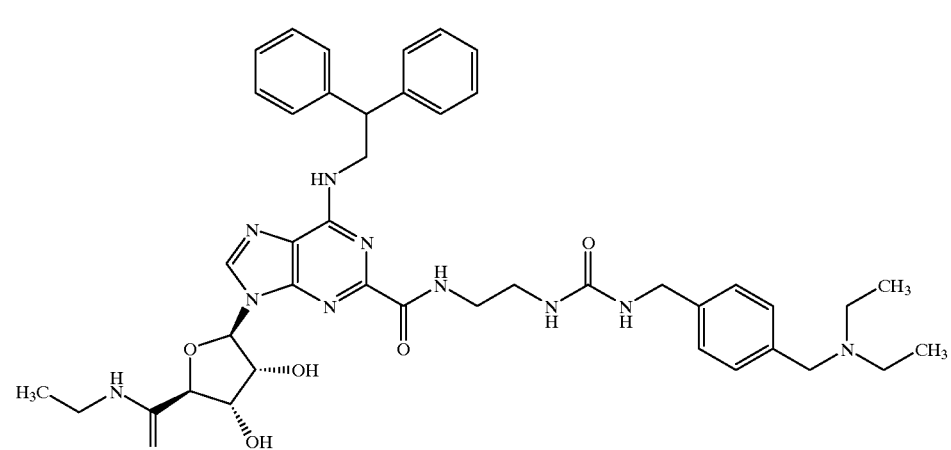 |

TABLE 1-continued
| Example No. | Compound |
|---|---|
| 18 | 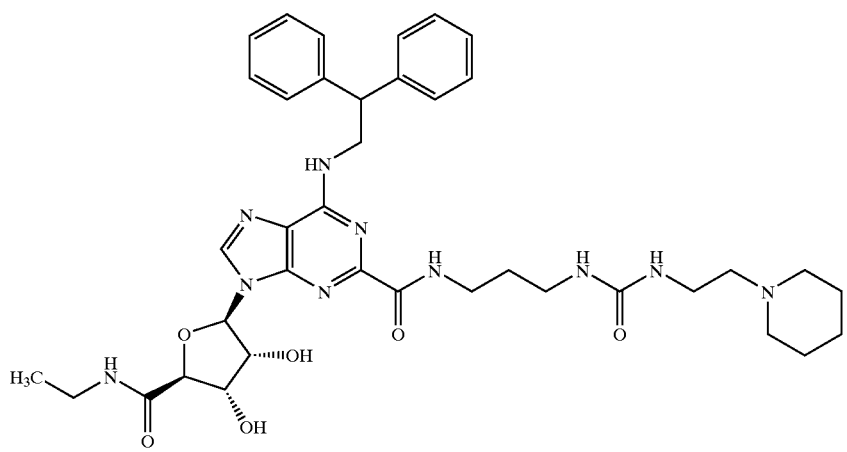 |
| 19 | 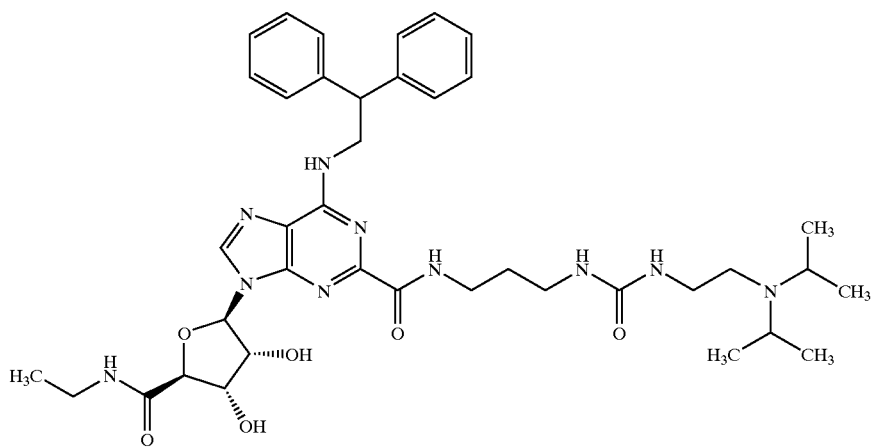 |
| 20 | 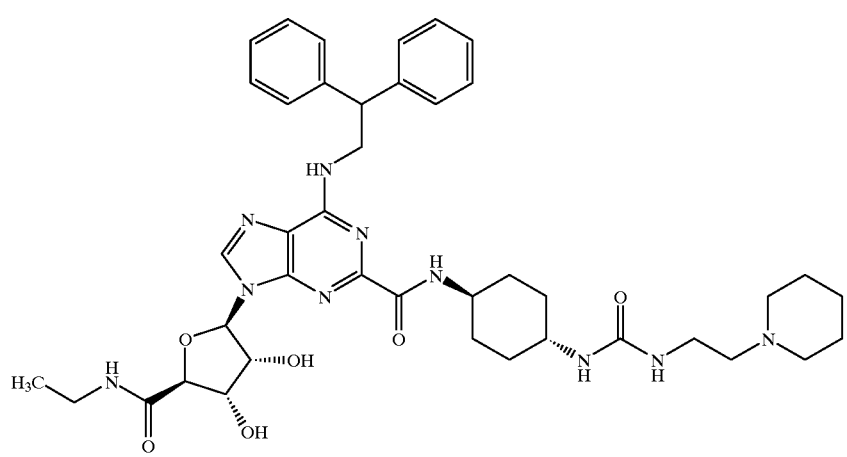 |

TABLE 1-continued
| Example No. | Compound |
|---|---|
| 21 | 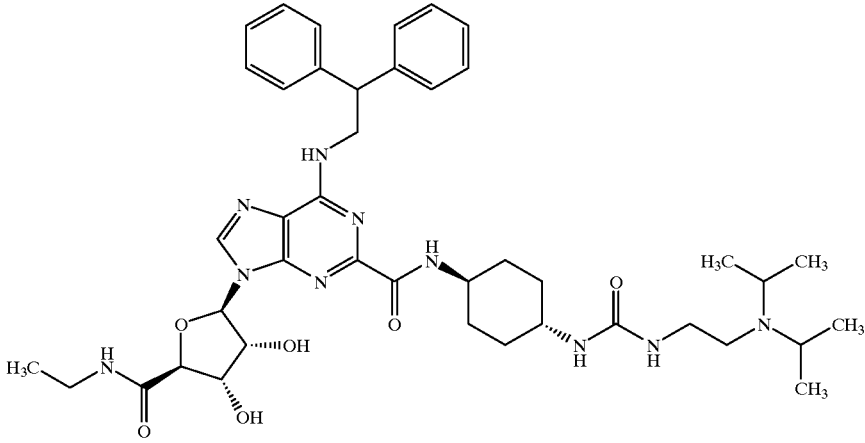 |
| 22 | 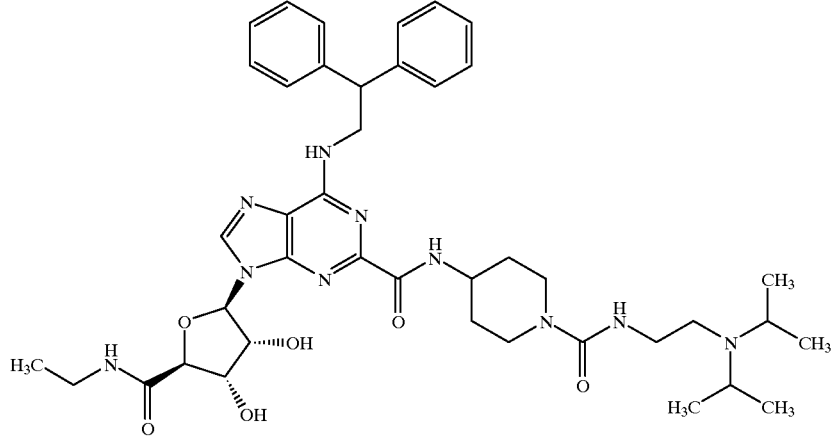 |
| 23 | 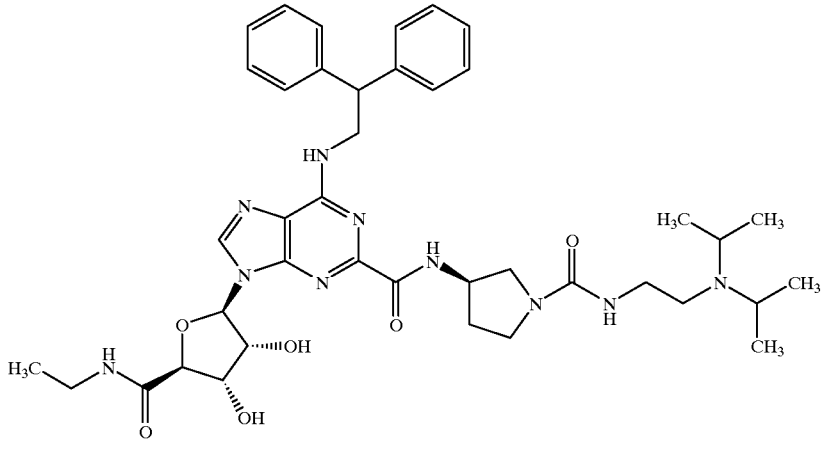 |

TABLE 1-continued

| Example No. | Compound |
|---|---|
| 24 | |
| 25 | |
| 26 | |

TABLE 1-continued

| Example No. | Compound |
|---|---|
| 27 | (structure shown) |

TABLE 2

| Example No. | ¹H-NMR (400 MHz) + solvent | LRMS (electrospray): m/z |
|---|---|---|
| 9 | (CDCl₃/CD₃OD) δ: 8.10 (1H, s), 7.30–7.10 (10H, m), 6.00 (1H, d), 4.80 (1H, br s), 4.60–4.25 (5H, m), 3.50–3.40 (2H, m), 3.20 (1H, m), 3.10 (2H, m), 2.45 (2H, m), 2.35 (2H, m), 1.40–1.35 (4H, m), 1.20 (4H, m), 1.00 (3H, t), 0.80 (6H, t). | [MH⁺] 773 |
| 10 | (CDCl₃/CD₃OD) δ: 8.35 (1H, m), 7.90 (1H, m), 7 30–7.10 (15H, m), 5.95 (1H, m), 5.20 (1H, m), 4.75 (1H, m), 4.55–4.45 (2H, m), 4.40–4.20 (3H, m), 3.60–3.20 (10H, m), 2.65 (1H, m), 2.50 (1H, m), 2.00–1.80 (2H, m), 1.70–1.55 (2H, m), 1.20 (1H, m), 1.05–0.90 (3H, m). | [MH⁺] 792 |
| 11 | (CDCl₃/CD₃OD) δ: 8.10 (1H, s), 7.30–7.10 (15H, m), 6.05 (1H, m), 4.70–4.55 (2H, m), 4.45 (1H, m), 4.40–4.25 (3H, m), 3.55–3.15 (8H, m), 3.00–2.80 (3H, m), 2.45 (1H, m), 1.00–0.90 (9H, m). | [MH⁺] 794 |
| 12 | (CDCl₃/CD₃OD) δ: 8.35 (1H, br s), 8.10 (1H, s), 7.30–7.10 (15H, m), 6.05 (1H, m), 4.75 (1H, br s), 4.65 (1H, br s), 4.50 (1H, m), 4.40–4.20 (3H, m), 3.60–3.10 (10H, m), 3.00–2.85 (2H, m), 2 75 (2H, m), 1.80 (2H, m), 1.50 (2H, m), 1 40–1 10 (3H), 0.90 (3H, m). | [MH⁺] 806 |
| 13 | (CDCl₃/CD₃OD) δ: 8.10 (1H, s), 7.30–7.05 (15H, m), 6.00 (1H, br s), 4.50 (2H, br s), 4.45 (1H, s), 4.35–4.20 (6H, m), 3.50–3.15 (6H, m), 0.95 (3H, t). | [MH⁺] 708, [MNa⁺] 730 |
| 14 | (CDCl₃/CD₃OD) δ: 8.40 (1H, br s), 8.15 (1H, s), 7.30–7.00 (15H, m), 6.10 (1H, br s), 4 65–4.50 (3H, m), 4.35–4.20 (3H, m), 3.60–3.15 (6H, m), 2.60 (2H, m), 0.95 (3H, t). | [MH⁺] 722, [MNa⁺] 744 |
| 15 | (CDCl₃/CD₃OD) δ: 8.15 (1H, s), 7.30–7.10 (10H, m), 6.05 (1H, m), 4.70–4.20 (6H, m), 3.60–3.20 (7H, m), 1.70 (2H, m), 1 60–1.40 (3H, m), 1.20 (2H, m), 1.00–0.90 (6H, m). | [MH⁺] 700, [MNa⁺] 722 |
| 16 | (CDCl₃/CD₃OD) δ: 8.05 (1H, s), 7.30–7.00 (13H, m), 6.90 (1H, m), 6.00 (1H, m), 4.70–4 60 (2H, m), 4.40–4.20 (4H, m), 3.70–3.60 (2H, m), 3.55–3.10 (8H, m), 2.90–2.60 (6H, m), 0.90 (3H, m). | [MH⁺] 778 |
| 17 | (CD₃OD) δ: 8.10 (1H, s), 7.30–7.05 (15H, m), 6.00 (1H, br s), 4.50 (2H, br s), 4.45 (1H, s), 4.35–4.20 (6H, m), 3.50–3.15 (6H, m), 0.95 (3H, t). | [MH⁺] 598, [MNa⁺] 620 |
| 18 | (CDCl₃/CD₃OD) δ 8.60 (1H, br s), 8.15 (1H, s), 7.30–7.15 (10H, m), 6.05 (1H, d), 4.80 (1H, br s), 4.50–4.30 (5H, m), 3.60–3.15 (8H, m), 2.45–2.35 (6H, m), 1.70 (2H, m), 1.55 (4H, m), 1.40 (2H, m), 1.05 (3H, t). | [MH⁺] 744 |
| 19 | (CDCl₃/CD₃OD) δ: 8.15 (1H, s), 7.30–7.10 (10H, m), 6.05 (1H, m), 4.70 (1H, m), 4.45 (2H, m), 4.40–4.20 (3H, m), 3.50–3.10 (6H, m), 3.05–2.90 (4H, m), 2.45 (2H, m), 1.70 (2H, m), 1.00–0.90 (15H, m). | [MH⁺] 760 |
| 20 | (CDCl₃/CD₃OD) δ: 8.50 (1H, s), 7.95 (1H, s), 7.40–7.20 (10H, m), 6.50 (1H, m), 4.80 (1H, m), 4.60–4.35 (3H, m), 4.30–4.20 (2H, m), 3.80 (1H, m), 3.60 (1H, m), 3 40–3.20 (3H, m), 2.60–2.40 (6H, m), 2.15–2.00 (4H, m), 1.65–1.20 (10H, m), 1.20 (3H, t). | [MH⁺] 784 |
| 21 | (CDCl₃/CD₃OD) δ: 8.30 (1H, s), 7.85 (1H, m), 7.30–7.10 (10H, m), 6.10 (1H, m), 4.60 (1H, m), 4.50 (1H, m), 4.35 (2H, m), 4.20 (2H, m), 3.80 (1H, m), 3.50–3.20 (3H, m), 3.10 (2H, m), 2.90 (2H, m), 2.50 (2H, m), 2.00 (4H, m), 1.40–1.20 (4H, m), 1.05 (3H, t), 1.00–0.90 (12H, m). | [MH⁺] 800 |

TABLE 2-continued

| Example No. | ¹H-NMR (400 MHz) + solvent | LRMS (electrospray): m/z |
|---|---|---|
| 22 | (CD₃OD) δ: 8.40 (1H, s), 7.30–7.10 (10H, m), 6.10 (1H, m), 4.80 (1H, m), 4.50–4.25 (5H, m), 4.05 (1H, m), 3.90 (2H, m), 3.40–2.90 (8H, m), 2.60 (2H, m), 1.90 (2H, m), 1.50 (2H, m), 1.10–1.00 (15H, m). | [MH⁺] 786 |
| 23 | (CD₃OD) δ: 8.40 (1H, s), 7.30–7.10 (10H, m), 6.10 (1H, m), 4.80 (1H, m), 4.50–4.25 (7H, m), 4.05 (1H, m), 3.70 (1H, m), 3.60–3.10 (8H, m), 2.60 (2H, m), 2.15 (1H, m), 2.10 (1H, m), 1.10–1.00 (15H, m). | [MH⁺] 771 |
| 24 | (CD₃OD) δ: 8.40 (1H, s), 7.40–7.10 (15H, m), 6.70 (1H, m), 6.10 (1H, m), 4.60 (1H, m), 4.45 (2H, m), 4.50–4.30 (4H, m), 3.80 (1H, m), 3.60–3.20 (7H, m), 2.30 (1H, m), 2.10 (1H, m), 1.05 (3H, t). | [MH⁺] 735 |
| 25 | (CD₃OD) δ: 8.20 (1H, s), 7.30–7.10 (15H, m), 5.95 (1H, m), 4.70–4.40 (4H, m), 4.30–4.20 (4H, m), 3.80 (1H, m), 3.55 (1H, m), 3.30–3.00 (4H, m), 2.00–1.80 (2H, m), 2.40 (2H, m), 1.10 (3H, t). | [M-H⁺] 746 |
| 26 | (CD₃OD) δ: 8.40 (1H, s), 7.40–7.10 (15H, m), 6.10 (1H, m), 4.60–4.20 (7H, m), 3.70 (1H, m), 3.50–3.20 (6H, m), 2.80 (2H, m), 2.25 (1H, m), 2.00 (1H, m), 1.00 (3H, t). | [M-H⁺] 746 |
| 27 | (CD₃OD) δ: 8.40 (1H, s), 8.00 (1H, m), 7.50 (1H, m), 7.35–7.20 (8H, m), 7.10 (2H, m), 6.80 (1H, m), 6.60 (1H, m), 6.05 (1H, m), 4.60–4.15 (8H, m), 3.80–3.65 (2H, m), 3.50–3.20 (4H, m), 2.85 (2H, m), 2.25 (1H, m), 2.00 (1H, m), 1.85 (2H, m), 1.45 (2H, m), 1.00 (3H, t). | [M-H⁺] 802 |

EXAMPLE 28
(2S,3S,4R,5R)-5-{2-({(3R)-3-[({[2-Diisopropylamino)ethyl]amino}carbonyl)amino]pyrrolidinyl}-carbonyl)-6-[(2,2-diphenylethyl)amino]-9H-purine-9-yl}-N-ethyl-3,4-dihydroxytetrahydro-2-furancarboxamide A solution of 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylic acid (Preparation 39) (200 mg, 0.37 mmol), N-[2-diisopropylamino)ethyl]-N'-[(3R)-pyrrolidinyl]urea (Preparation 44) (106 mg, 0.41 mmol), 1-(3-dimethylaminopropyl)-3-ethylcarbodiimide hydrochloride (79 mg, 0.41 mmol) and 1-hydroxybenzotriazole (5 mg, 0.037 mmol) in dichloromethane (5 ml) was stirred at room temperature for 14 hours. Water (1 ml) was added and the organic layer separated The aqueous phase was extracted with more dichloromethane (2×1 ml) and the combined extracts dried over anhydrous magnesium sulphate. Solvent was evaporated under reduced pressure and the residue purified by column chromatography on silica gel eluting with a gradient system of dichloromethane:methanol:concentrated aqueous ammonia (90:10:1, by volume) changing to dichloromethane:methanol:concentrated aqueous ammonia (80:20:1, by volume). After evaporation of appropriate fractions the residue was triturated with diethyl ether, filtered and dried to yield the target compound as a white solid, (0.1 g, 35%).

¹H-NMR (400 MHz, CD₃OD) δ: 8.25 (1H, s), 7.30–7.10 (10H, m), 5.95 (1H, m), 4.70 (1H, m), 4.45 (2H, m), 4.30–4.10 (4H, m), 3.70–3.40 (4H, m), 3.30–3.00 (7H, m), 2.50 (2H, m), 2.20 (2H, m), 1.80 (1H, m), 1.10–0.90 (15H, m).

LRMS: m/z [MH⁺] 771.

EXAMPLE 29
(2S,3S,4R,5R)-5-{2-({(3S)-3-[({[2-Diisopropylamino)ethyl]amino}carbonyl)amino]pyrrolidinyl}-carbonyl)-6-[(2,2-diphenylethyl)amino]-9H-purin-9-yl}-N-ethyl-3,4-dihydroxytetrahydro-2-furancarboxamide

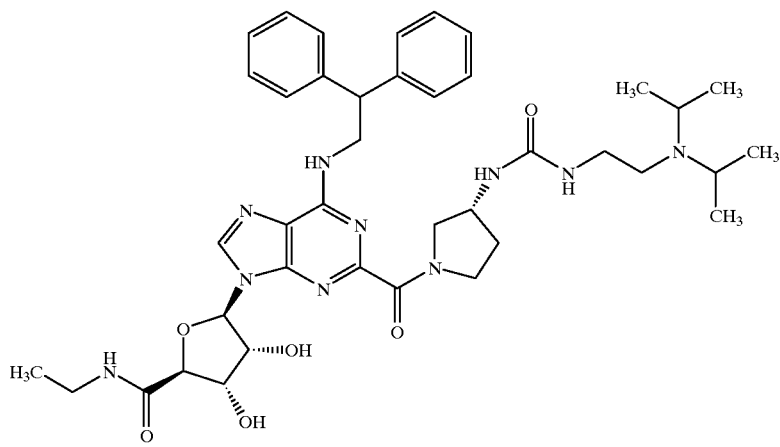

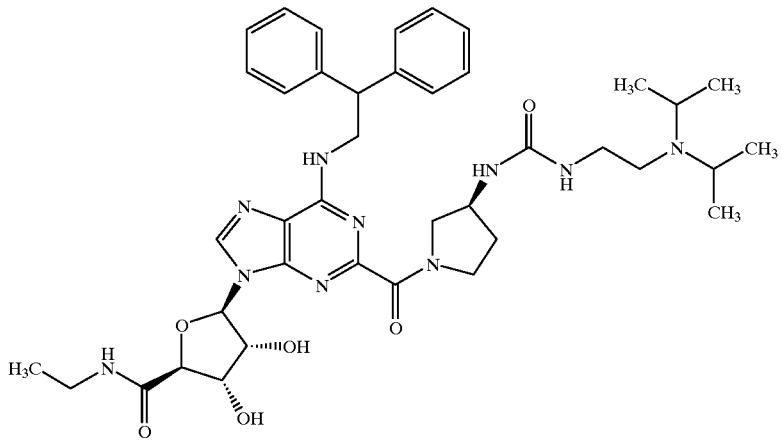

Prepared from 6-[(2,2-diphenylethyl)amino]-9-{(2R,3R,4S,5S)-5-[(ethylamino)carbonyl]-3,4-dihydroxytetrahydro-2furanyl}-9H-purine-2-carboxylic acid (Preparation 39) and N-[2-(diisopropylamino)ethyl]-N'-[(3S)-pyrrolidinyl]urea (Preparation 45) by the same method as Example 28. The title compound was obtained as a white powder.

$^1$H-NMR (400 MHz, CD$_3$OD) δ: 8.25 (1H, s), 7.30–7.10 (10H, m), 5.95 (1H, m), 4.70 (1H, m), 4.45 (2H, m), 4.30–4.10 (4H, m), 3.80–3.60 (4H, m), 3.10–2.90 (7H, m), 2.55 (1H, m), 2.40 (1H, m), 2.30 (2H, m), 1.85 (1H, m), 1.60 (2H, m), 1.10–0.90 (15H, m).

LRMS: m/z [M-H$^+$] 769.

EXAMPLE 30
6-{[2,2-Bis(3-methylphenyl)ethyl]amino}-N-{2-[({[2-(diisopropylamino)ethyl]amino}carbonyl)-amino]ethyl}-9-{(2R,3R,4S,5S)-5-[(ethylamino)carbonyl]-3,4-dihydroxytetrahydro-2-furanyl}-9H-purine-2-carboxamide A solution of (2R,3R,4S,5S)-4-(benzoyloxy)-2-(6-{[2,2-bis(3-methylphenyl)ethyl]amino}-2-iodo-9H-purin-9-yl)-5-[(ethylamino)carbonyl]tetrahydro-3-furanyl benzoate (Preparation 48) (200 mg, 0.24 mmol), N-(2-aminoethyl)-N'-[2-(diisopropylamino)ethyl]urea (Preparation 52) air (270 mg, 1.18 mmol) and tetrakis(triphenylphosphine)palladium(0) (27 mg, 0.024 mmol) In THF (5 ml) was carbonylated at 60° C. and 345 KPa under a carbon monoxide atmosphere for 14 hours. TLC analysis showed the desired product together with partially deprotected material. To achieve complete removal of the benzoate protecting groups, solvent was evaporated under reduced pressure, the residue dissolved in methanol (10 ml), sodium carbonate (10 mg) added and the mixture allowed to stir at room temperature for 24 hours Solvent was again evaporated under reduced pressure and the residue purified by column chromatography on silica gel eluting with a gradient system of dichloromethane:methanol (90:10, by volume) changing to dichloromethane:methanol:concentrated aqueous ammonia (90:10:1, by volume). After evaporation of appropriate fractions the residue was triturated with diethyl ether, filtered and dried to yield the target compound as a white solid, (0.11 g, 61%).

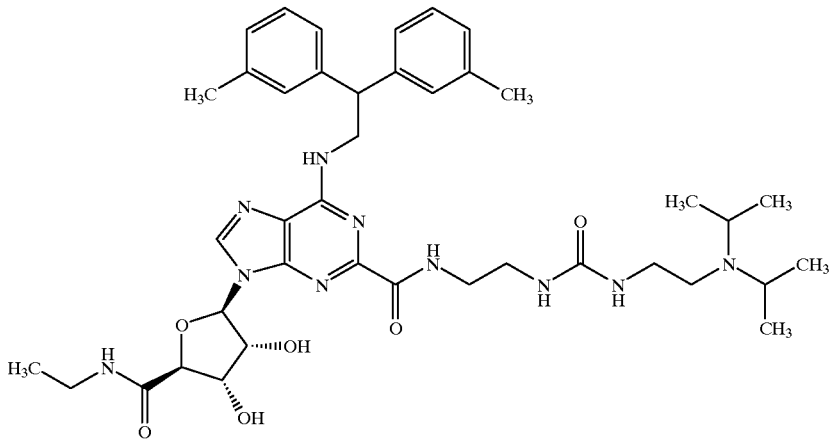

$^1$H-NMR (400 MHz, CD$_3$OD) δ: 8.40 (1H, s), 7.20–7.10 (6H, m), 6.95 (2H, m), 6.10 (1H, m), 4.45–4.35 (4H, m), 3.55–3.00 (10H, m), 2.55 (2H, m), 2.30 (6H, s), 1.10–0.90 (15H, m).

LRMS: m/z [MH$^+$] 773.

EXAMPLE 31

6-{[2,2-Bis(3-chlorophenyl)ethyl]amino}-N-{2-[({[2-diisopropylamino)ethyl]amino}carbonyl)-amino]ethyl}-9-{(2R,3R,4S,5S)-5-[(ethylamino)carbonyl]-3,4-dihydroxytetrahydro-2-furanyl}-9H-purine-2-carboxamide

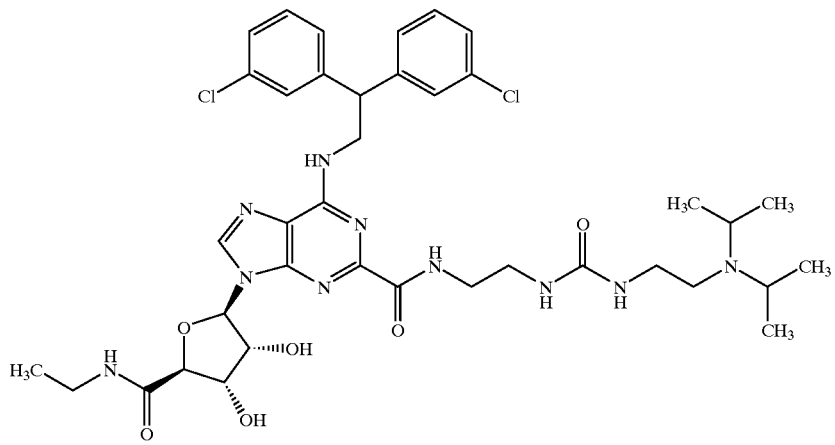

Prepared from (2R,3R,4S,5S)-4-(benzoyloxy)-2-(6-{[2,2-bis(3-chlorophenyl)ethyl]amino}-2-iodo-9H-purin-9-yl)-5-[(ethylamino)carbonyl]tetrahydro-3-furanyl benzoate (Preparation 49) and N-(2-aminoethyl)-N'-[2-(diisopropylamino)ethyl]urea (Preparation 52) by a similar method to Example 30. The target compound was obtained as a white solid.

$^1$H-NMR (400 MHz, CD$_3$OD) δ: 8.40 (1H, s), 7.45–7.15 (6H, m), 6.10 (1H, m), 4.50–4.40 (4H, m), 3.60–3.20 (6H, m), 3.05 (2H, m), 2.90 (2H, m), 2.45 (2H, m), 1.05 (3H, t), 0.90 (12H, d).

LRMS: m/z [M-H$^+$] 815.

EXAMPLE 32

6-{[2,2-Bis(3-chlorophenyl)ethyl]amino}-9-{(2R,3R,4S,5S)-5-[(ethylamino)carbonyl]-3,4-dihydroxytetrahydro-2-furanyl}-N-{2-[({[2-(1-piperidinyl)ethyl]amino}carbonyl)amino]ethyl}-9H-purine-2-carboxamide Prepared from (2R,3R,4S,5S)-4-(benzoyloxy)-2-6-{[2,2-bis(3-chlorophenyl)ethyl]amino}-2-iodo-9H-purin-9-yl)-5-[(ethylamino)carbonyl]tetrahydro-3furanyl benzoate (Preparation 49) and N-(2-aminoethyl)-N'-[2-(1-piperidinyl)ethyl]urea (Preparation 53) by a similar method to Example 30. The target compound was obtained as a white solid.

$^1$H-NMR (400 MHz, CD$_3$OD) δ: 8.40 (1H, br s), 7.45–7.10 (8H, m), 6.10 (1H, d), 4.50–4.35 (4H, m), 3.55–3.20 (8H, m), 2.80–2.60 (6H, m), 1.70–1.40 (6H, m), 1.00 (3H, t).

LRMS: m/z [M-H$^+$] 797.

EXAMPLE 33

6-{[2,2-Bis(3-methylphenyl)ethyl]amino}-9-(2R,3R,4S,5S)-5-[(ethylamino)carbonyl]-3,4-dihydroxytetrahydro-2-furanyl}-N-{2-[({[2-(1-piperidinyl)ethyl]amino}carbonyl)amino]ethyl}-9H-purine-2-carboxamide

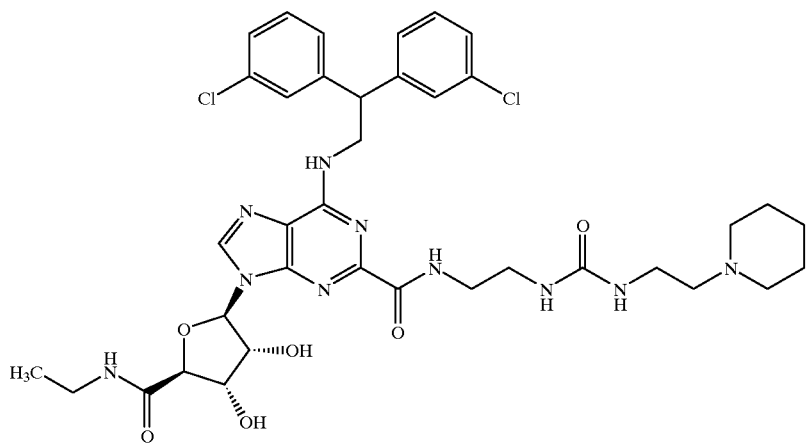

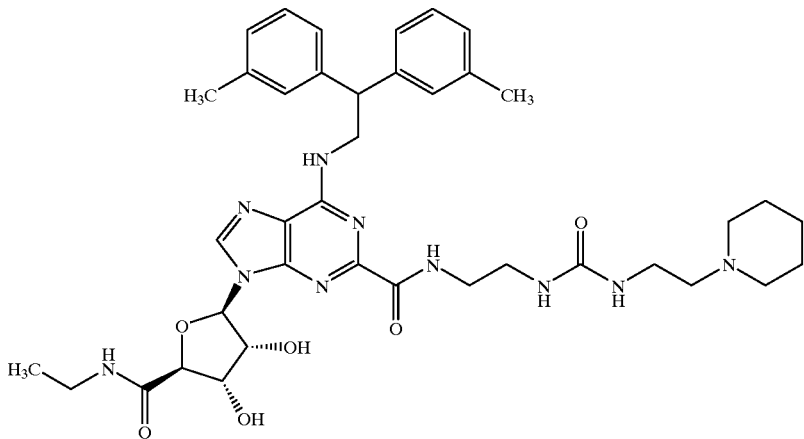

Prepared from (2R,3R,4S,5S)-4-(benzoyloxy)-2-(6-{[2,2-bis(3-methylphenyl)ethyl]amino}-2-iodo-9H-purin-9-yl)-5-[(ethylamino)carbonyl]tetrahydro-3furanyl benzoate (Preparation 48) and N-(2-aminoethyl)-N'-[2-1-piperidinyl)ethyl]urea (Preparation 53) by a similar method to Example 30. The target compound was obtained as a white solid.

¹H-NMR (400 MHz, CD$_3$OD) δ: 8.40 (1H, br s), 7.20–7.10 (6H, m), 6.95 (2H, m), 6.10 (1H, d), 4.45–4.30 (4H, m), 3.55–3.20 (8H, m), 2.80–2.60 (6H, m), 2.20 (6H, s), 1.70–1.40 (6H, m), 1.00 (3H, t).

LRMS: m/z [MH$^+$] 758.

EXAMPLE 34
4-[({[(2-{[(6-[(2,2-diphenylethyl)amino]-9-{(2R,3R,4S,5S)-5-[(ethylamino)carbonyl]-3,4-dihydroxytetrahydro-2-furanyl}-9H-purine-2-yl)carbonyl]amino}ethyl)amino]carbonyl}-amino)methyl]benzoic acid A solution of benzyl 4-[({[(2-{[(6-[(2,2-diphenylethyl)amino]-9-{(2R,3R,4S,5S)-5-[(ethylamino)carbonyl]-3,4-dihydroxytetrahydro-2-furanyl}-9H-purine-2-yl)carbonyl]amino}ethyl)amino]carbonyl}amino)methyl]benzoate (Preparation 55) (150 mg, 0.18 mmol) in ethanol (10 ml) was hydrogenated at room temperature over 10% w/w palladium-on-carbon (30 mg) for 28 hours at 414 KPa. The catalyst was removed by filtration through Arbocel (trade mark) and solvent evaporated under reduced pressure to afford the title compound as a white powder (26 mg).

¹H-NMR (400 MHz, CD$_3$OD) δ: 8.40 (1H, s), 7.80 (2H, d), 7.40 (4H, m), 7.25 (6H, m), 7.15 (2H, m), 6.10 (1H, m), 4.80 (1H, m), 4.50–4.30 (5H, m), 3.60–340 (4H, m), 3.40–3.20 (2H, m), 1.05 (3H, t).

LRMS: m/z [M-H$^+$] 750.

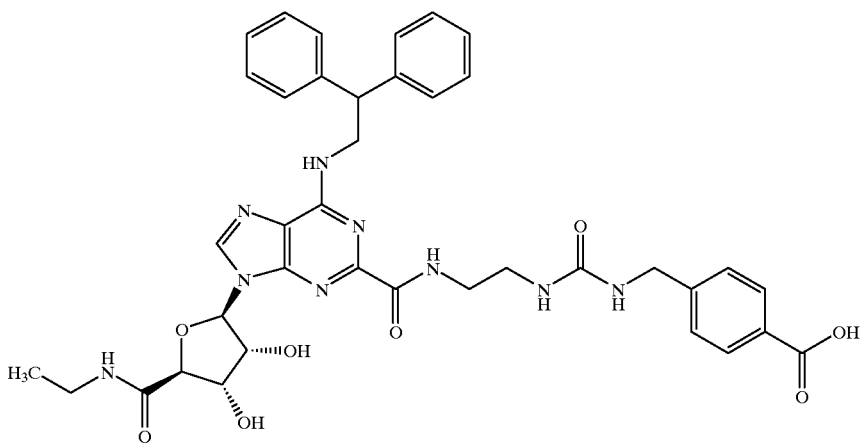

EXAMPLE 35
6-[(2,2-Diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide

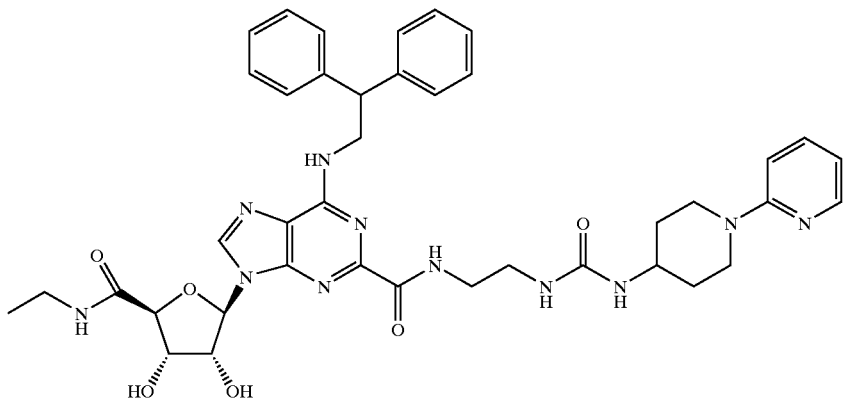

To a solution of 9-{(3aR,4R,6S,6aS)-6-[(ethylamino)carbonyl]-2,2-dimethyltetrahydrofuro[3,4-d][1,3]dioxol-4-yl}-6-[(2,2-diphenylethyl)amino]-N-{2-[({[1-(2-pyridinyl)-4-piperidinyl]amino}carbonyl)amino]ethyl}-9H-purine-2-carboxamide (Preparation 71) (20.9 g, 0.0255 moles) in absolute ethanol (200 ml) was added aqueous hydrochloric acid (76.5 ml of a 1M solution, 0.0765 moles) and the resultant solution was heated at 60–65° C. for 24 hours. The reaction mixture was allowed to cool to ambient temperature and saturated aqueous sodium bicarbonate solution (200 ml) was cautiously added. The resultant mixture was then concentrated in vacuo and the aqueous mixture was then extracted with ethyl acetate (200 ml) and then dichloromethane (200 ml). The extracts were dried over anhydrous magnesium sulphate which caused the deposition of a gum that was redissolved by the addition of dichloromethane (100 ml) and methanol (20 ml). The resultant violet solution was then concentrated in vacuo to give the crude product as a purple foam (20.86 g) that was purified by flash chromatography on silica gel (600 g) eluting with a gradient of 6% v/v methanol in dichloromethane changing to 8% v/v methanol in dichloromethane changing to 10% v/v methanol in dichloromethane changing to 15% v/v methanol in dichloromethane to give the title compound in several fractions of varying purity. The major fraction (11.4 g) was dissolved in dichloromethane (264 ml) and was filtered to remove insoluble matter To this solution was added diethyl ether (112 ml) and the resultant cloudy mixture was stirred at ambient temperature for 1 hour. The solids were then collected by filtration and were dried in vacuo. This material was then ground using a pestle and mortar and was dried further in vacuo at 50° to give the title compound (9.9 g) as a fine colourless powder.

LRMS (positive atmospheric pressure chemical ionisation): m/z [MH$^+$] 778.

$^1$H-NMR (600 MHz, d$_6$-DMSO, 30° C.) δ: 8.80 (0.8H, br t), 8.67 (0.2H, br s), 8.53 (0.2H, br s), 8.48 (0.8H, s), 8.28 (1H, t), 8.10–8.02 (1.8H, m), 7.84 (0.2H, br s), 7.50–7.30 (5H, m), 7.26 (4H, t), 7.14 (2H, t), 6.75 (1H, d), 6,56 (1H, dd), 6.11–5.82 (3H, m), 5.65 (1H, d), 5.57 (0.2H, br s), 5.53 (0.8H, d), 4.72 (0.2H, br s), 4.68–4.50 ((2.2H, m), 4.36–4.21 (2.8H, m), 4.17 (0.8H, br s), 4.04 (2H, br d), 3.67–3.55 (1H, m), 3.40–3.10 (6H, m (partly obscured by water peak)), 2.91 (0.4H, br s), 2.81 (1.6H, br t), 1.74 (2H, br d), 1.30–1.16 (2H, m), 0.98 (3H, t). Acquiring the $^1$H NMR spectrum at 70° C. results in the disappearance of signals attributable to the observation of more than one conformer at 30° C.

The following Preparations describe the preparation of certain intermediates used in the preceding Examples.

Preparation 1
2,6-Dichloro-9-(tetrahydro-2H-pyran-2-yl)-9H-purine

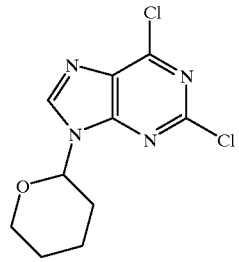

2,6-Dichloro-9H-purine (20 g, 0.11 mol) and 4-toluenesulphonic acid monohydrate (0.2 g) were dissolved in ethyl acetate (300 ml), the mixture heated to 50° C. and a solution of 3,4-dihydro-2H-pyran (12.6 ml, 0.14 mol) in ethyl acetate (50 ml) added slowly over 30 minutes The reaction mixture was cooled to room temperature, water (100 ml) added and the pH of the solution adjusted to 7 by addition of a saturated aqueous solution of sodium hydrogen carbonate. The organic layer was separated, washed sequentially with water and brine, dried over anhydrous magnesium sulphate, filtered and the solvent removed under reduced pressure. The residue was azeotroped with pentane (×2) to afford the title compound as a slightly impure white solid (30.9 g).

$^1$H-NMR (400 MHz, CDCl$_3$) δ: 8.30 (1H, s), 5.75 (1H, dd), 4.25–4.15 (1H, m), 3.85–3.70 (1H, m), 2.20–1.60 (6H, m).

Preparation 2

2-Chloro-N-(2,2-diphenylethyl)-9-(tetrahydro-2H-pyran-2-yl)-9H-purin-6-amine

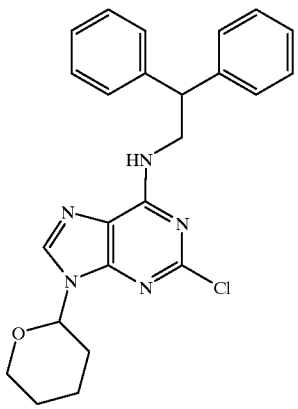

A solution of 2,6-dichloro-9-tetrahydro-2H-pyran-2-yl)-9H-purine (Preparation 1) (30.9 g, 0.11 mol) in isopropyl alcohol (600 ml) was treated with N-ethyl-N-isopropyl-2-propanamine (47.5 ml, 0.27 mol) and 2,2-diphenylethylamine (24.8 g, 0.13 mol) and the resulting mixture heated under reflux for 3 hours. The solvent was removed under reduced pressure and the residue azeotroped with ethyl acetate. The residue was purified by column chromatography on silica gel eluting with a gradient system of ethyl acetate:hexane (40:60, by volume) gradually changing to ethyl acetate hexane (60:40, by volume) to afford the title compound as a foam (49.7 g).

$^1$H-NMR (400 MHz, CDCl$_3$) δ: 7.95–7.75 (1H, br s), 7.35–7.15 (10H, m), 5.80–5.70 (1H, br s), 5.65 (1H, d), 4.35 (1H, m), 4.30–4.18 (1H, brs), 4.10 (1H, d), 3.70 (1H, t), 2.05–1.95 (2H, m), 1.95–1.80 (1H, m), 1.80–1.55 (3H, m).

Preparation 3

N-(2,2-Diphenylethyl)-2-(methylsulfanyl)-9-(tetrahydro-2H-pyran-2-yl)-9H-purin-6-amine

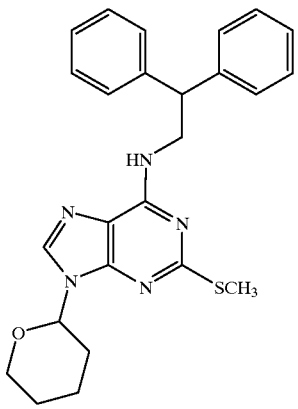

A solution of 2-chloro-N-(2,2-diphenylethyl)-9-(tetrahydro-2H-pyran-2-yl)-9H-purin-6-amine (Preparation 2) (49.7 g, 0.11 mol) in dry N,N-dimethylformamide (200 ml) was treated with sodium thiomethoxide (10 g, 0.14 mol) and the resulting mixture heated under an atmosphere of nitrogen at 100° C. for 90 minutes The mixture was stirred at room temperature for 72 hours and then reheated at 100° C. for a further 2 hours. The reaction mixture was cooled and diluted with water (1000 ml). A suspension was formed which was extracted with diethyl ether (×2). The combined organic layers were washed sequentially with water and brine, dried over anhydrous magnesium sulphate, filtered and the solvent removed under reduced pressure. The residue was azeotroped with diethyl ether followed by pentane to afford the title compound as a foam (48.9 g).

$^1$H-NMR (400 MHz, CDCl$_3$) δ: 7.80 (1H, s), 7.20–7.10 (10H, m), 5.70–5.55 (2H, d), 4.40–4.20 (3H, m), 4.20–4.05 (1H, m), 3.80–3.65 (1H, m), 2.60 (3H, s), 2.15–1.90 (3H, m), 1.90–1.60 (3H, m).

Preparation 4

N-(2,2-Diphenylethyl)-2-(methylsulfonyl)-9-(tetrahydro-2H-pyran-2-yl)-9H-purin-6-amine

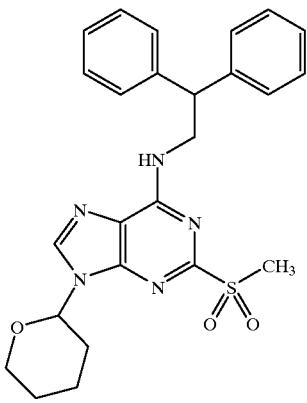

A solution of Oxone (trade mark)(potassium peroxymonosulphate) (44 g, 71.7 mmol) in water (200 ml) was added dropwise over 2 hours to a solution of N-(2,2-diphenylethyl)-2-(methylsulfanyl)-9-(tetrahydro-2H-pyran-2-yl)-9H-purin-6-amine (Preparation 3) (25 g, 56.2 mmol) and sodium hydrogencarbonate (20 g, 238 mmol) in acetone (1000 ml) and water (250 ml). The resultant mixture was stirred at room temperature for 24 hours, filtered and the residue washed with acetone. The acetone was removed from the filtrate under reduced pressure and the resulting aqueous residue extracted with ethyl acetate and then dichloromethane. The combined organic layers were washed with brine, dried with anhydrous magnesium sulphate, filtered and the solvent removed under reduced pressure. The residue was triturated with diethyl ether, filtered, washed with diethyl ether and pentane and then dried to afford the title compound as a white solid (20.32 g).

$^1$H-NMR (400 MHz, CDCl$_3$) δ: 8.00 (1H, s), 7.35–7.15 (10H, m), 6.05–5.95 (1H, br s), 5.75 (1H, d), 4.40–4.35 (1H, m), 4.35–4.20 (2H, br s), 4.15–4.05 (1H, m), 3.75 (1H, t), 3.30 (3H, s), 2.18–2.05 (1H, m), 2.05–1.98 (1H, m), 1.98–1.80 (1H, m), 1.80–1.60 (3H, m).

Preparation 5
6-[(2,2-Diphenylethyl)amino]-9-(tetrahydro-2H-pyran-2-yl)-9H-purine-2-carbonitrile

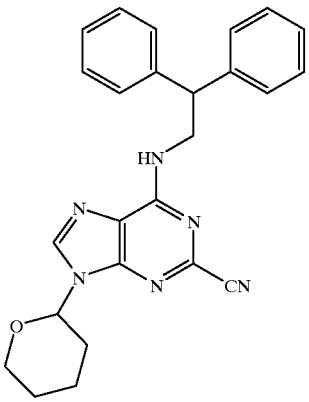

A solution of N-(2,2-diphenylethyl)-2-(methylsulfonyl)-9-tetrahydro-2H-pyran-2-yl)-9H-purin-6-amine (Preparation 4) (20.1 g, 42.1 mmol) in dry N,N-dimethylformamide (100 ml) was treated with potassium cyanide (5.5 g, 84.6 mmol) and the mixture heated at 120° C. for 24 hours under a nitrogen atmosphere. The mixture was cooled to room temperature, poured into water (1000 ml) and stirring continued for a further 1 hour. The resultant solid was filtered and washed several times with water. The solid was then dissolved in dichloromethane and the solution washed with water, dried with anhydrous magnesium sulphate, filtered and the solvent removed under reduced pressure. The residue was azeotroped with diethyl ether (twice) to afford the title compound as an oil (17 g).

$^1$H-NMR (400 MHz, CDCl$_3$) δ: 8.00 (1H, s), 7.40–7.20 (10H, m), 6.00–5.75 (1H, br s), 5.70 (1H, d), 4.40–4.20 (3H, m), 4.20–4.10 (1H, m), 380–3.70 (1H, m), 2.20–1.90 (3H, m), 1.90–1.60 (3H, m).

Preparation 6
6-[(2,2-Diphenylethyl)amino]-9H-purine-2-carbonitrile

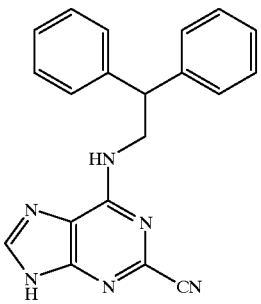

A solution of 6-[(2,2-diphenylethyl)amino]-9-tetrahydro-2H-pyran-2-yl)-9H-purine-2-carbonitrile (Preparation 5) (17 g, 40.1 mmol) in ethanol (850 ml) was treated with 2 N aqueous hydrochloric acid (50 ml) and the mixture stirred at room temperature for 24 hours. The solvent was removed under reduced pressure, the residue dissolved in ethanol and the solvent again removed under reduced pressure. The residue was triturated with diethyl ether, filtered, washed with diethyl ether and pentane, and dried to afford the title compound as a solid (13,6 g).

$^1$H-NMR (400 MHz, DMSO-d$_6$) δ: 8.30 (1H, s), 8.20–8.05 (1H, br s), 7.40–7.10 (10H, m), 4.60–4.40 (1.4H, m), 4.20–4.00 (1.6H, m).

LRMS (thermospray): m/z [MH$^+$] 341.

Preparation 7
Methyl 6-[(2,2-diphenylethyl)amino]-9H-purine-2-carboxylate

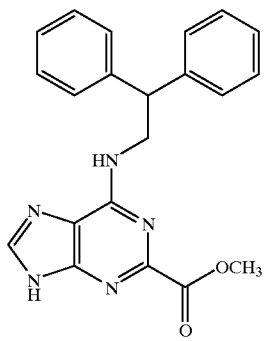

A solution of 6-[(2,2-diphenylethyl)amino]-9H-purine-2-carbonitrile (Preparation 6) (5.0 g, 14.7 mmol) and sodium methoxide (4.0 g, 74.1 mmol) in methanol (300 ml) was heated under reflux for 24 hours. Further sodium methoxide (2.0 g, 37 mmol) and methanol (100 ml) was added and heating continued for a further 24 hours. The reaction mixture was allowed to cool and the solvent removed under reduced pressure. The residue was dissolved in tetrahydrofuran (THF) (375 ml), 2N aqueous hydrochloric acid (125 ml) added and the mixture stirred at room temperature for 24 hours. The THF was removed under reduced pressure and the suspension basified to pH 7 with saturated aqueous sodium bicarbonate solution Ethyl acetate (100 ml) was added and the white solid consisting mainly of the desired product filtered, washed with a little water and ethyl acetate and dried. Purification by column chromatography on silica gel eluting with a gradient system of dichloromethane:methanol (90:10, by volume) gradually changing to dichloromethane:methanol (75:25, by volume) afforded the title compound as a white solid, 1.25 g (25%). Evaporation of the ethyl acetate filtrate provided 2.6 g of the starting material.

$^1$H-NMR (400 MHz, CDCl$_3$) δ: 12.40 (1H, br s), 8.05 (1H, s), 7.55 (1H, s), 7.55 (1H, s), 7.30–7.20 (10H, m), 4.80 (2H, m), 4.75 (1H, m), 3.80 (3H, s).

LRMS (thermospray): m/z [MH$^+$] 375.

Preparation 8

Methyl 9{-(2R,3R,4R,5S)-3,4-bis(benzoyloxy)-5-[(ethylamino)carbonyl]-tetrahydro-2-furanyl}-6-[(2,2-diphenylethyl)amino]-9H-purine-2-carboxylate

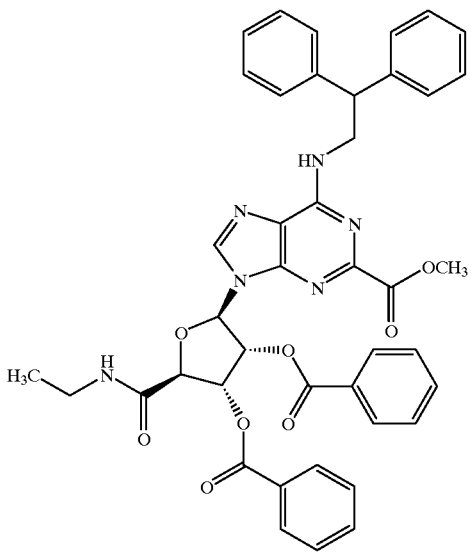

A suspension of methyl 6-[(2,2-diphenylethyl)amino]-9H-purine-2-carboxylate (Preparation 7) (440 mg, 1.18 mmol) in 1,1,1-trichloroethane (25 ml) was treated with N,O-bis(trimethylsilyl)acetamide (1.7 ml, 6.95 mmol). The mixture was heated under reflux for one hour. The solution was allowed to cool to room temperature and the solvent removed under reduced pressure. The residue was treated with a solution of (2S,3S,4R,5R)- and (2S,3S,4R,5S)-5-(acetyloxy)-4-(benzoyloxy)-2-[(ethylamino)carbonyl] tetrahydro-3-furanyl benzoate (Preparation 14) (620 mg, 1.4 mmol) in anhydrous toluene (25 ml) and then with trimethylsilyl trifluoromethanesulfonate (0.26 ml, 1.42 mmol). The resulting solution was then heated at 110° C. under a nitrogen atmosphere for 2.5 hours. The mixture was cooled to room temperature, diluted with ethyl acetate (200 ml) and washed with a saturated aqueous solution of sodium hydrogen carbonate. The organic layer was separated, dried over anhydrous magnesium sulphate, filtered and the solvent removed under reduced pressure. The residue was purified by column chromatography on silica gel eluting in a gradient manner with dichloromethane:ethyl acetate (5:1, by volume) then dichloromethane ethyl acetate (1:1, by volume) to afford the title compound as a foam (540 mg, 60%).

$^1$H-NMR (400 MHz, CDCl$_3$) δ: 8.10 (3H, m), 780 (2H, d), 7.60 (1H, m), 7.50–7.40 (4H, m), 7.35–7.20 (16H, m), 6.40 (1H, m), 6.20 (2H, m), 5.90 (1H m), 4.90 (1H, d), 4.40 (3H, m), 4.00 (3H, s), 3.55 (1H, m), 3.35 (1H, m), 1.15 (3H, t).

LRMS (thermospray): m/z [MNa$^+$] 777.

Preparation 9

Methyl 6-[(2,2-diphenylethyl)amino]-9{-(2R,3R,4R,5S)-5-[(ethylamino)carbonyl]-3,4-dihydroxytetrahydro-2-furanyl}-9H-purine-2-carboxylate

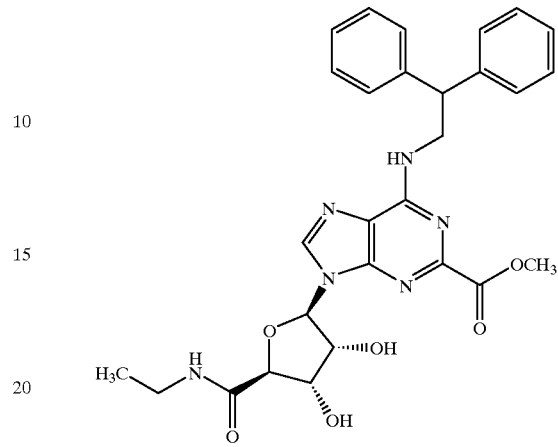

A solution of methyl 9-{(2R,3R,4R,5S)-3,4-bis(benzoyloxy)-5-[(ethylamino)carbonyl]-tetrahydro-2-furanyl}-6-[(2,2-diphenylethyl)amino]-9H-purine-2-carboxylate (Preparation 8) (3.4 g, 4.5 mmol) and sodium carbonate (50 mg) in dry methanol (60 ml) was stirred at room temperature for four hours Solvent was removed under reduced pressure and the residue taken up in a mixture of dichloromethane:methanol (95:5, by volume, 60 ml). Inorganic salts were filtered off and the filtrate evaporated under reduced pressure. The residue was triturated with diethyl ether, filtered off and dried to yield the title compound as a white solid, (2.4 g, 98%).

$^1$H-NMR (400 MHz, d$_6$-DMSO) δ: 8.60 (1H, m), 8.15 (2H, br s), 7.40–7.15 (10H, m), 6.00 (1H, br m), 5.60 (1H, br s), 5.50 (1H, br s), 4.60–4.40 (3H, m), 4.30 (1H, s), 4.10–4.05 (2H, m), 4.00–3.80 (3H, m), 3.20 (2H, m), 1.00 (3H, t).

LRMS (thermospray): m/z [MH$^+$] 547.

Preparation 10

N-(2-Aminoethyl)-6-[(2,2-diphenylethyl)amino]-9{(2R,3R,4R,5S)-5-[(ethylamino)carbonyl]-3,4-dihydroxytetrahydro-2-furanyl}-9H-purine-2-carboxamide

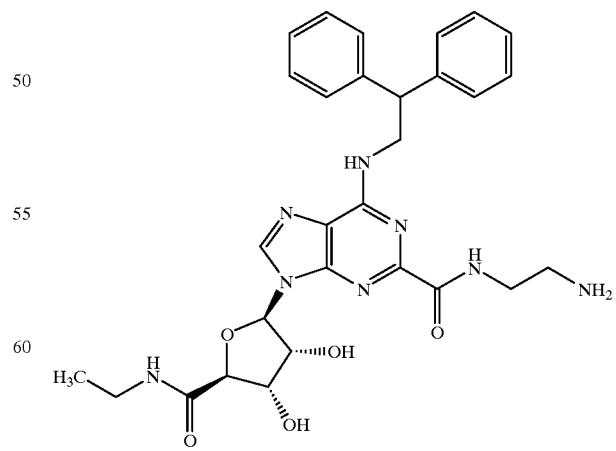

A mixture of methyl 6-[(2,2-diphenylethyl)amino]-9-{(2R,3R,4S,5S)-5-[(ethylamino)carbonyl]-3,4- dihydroxytetrahydro-2-furanyl}-9H-purine-2-carboxamide (Preparation 9) (1.1 g, 2 mmol) and 1,2-ethylenediamine (1.1 g, 18.3 mmol) was heated at 105° C. for 2.5 hours. The mixture was dissolved in a little dichloromethane and purified by column chromatography on silica gel eluting with dichloromethane:methanol:concentrated aqueous ammonia (85:15:1.5, by volume). After evaporation of appropriate fractions the residue was triturated with diethyl ether, filtered and dried to yield the target compound as a white solid, (0.99 g, 86%)

$^1$H-NMR (400 MHz, CDCl$_3$) δ: 8.75 (1H, br s), 8.60 (1H, br s), 7.50 (1H, br s), 7.50 (1H, br s), 7.40–7.20 (10H, m), 6.90 (1H, d), 6.10 (1H, br s), 5.05 (1H, s), 4.55 (1H, s), 4.45–4.20 (4H, m), 3.50–3.35 (4H, m), 2.95 (2H, t), 1.25 (3H, t).

LRMS (thermospray): m/z [MH$^+$] 575.

Preparation 11

(3aS,4S,6R,6aR)-N-Ethyl-6-methoxy-2,2-dimethyltetrahydrofuro[3,4-d][1,3]dioxide-4-carboxamide

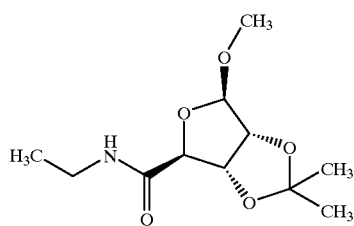

Oxalyl chloride (14.0 ml, 160 mmol) was added dropwise to a stirred solution of (3aR,4S,6R,6aR)-6-methoxy-2,2-dimethyltetrahydrofuro[3,4-d][1,3]dioxole-4-carboxylic acid (J. Amer. Chem. Soc., 80, 5168–5173 (1958)) (23.30 g, 107 mmol) in anhydrous dichloromethane (120 ml) and N,N-dimethylformamide (2 drops) and the mixture stirred at room temperature for 3 hours until gas evolution had ceased. TLC analysis showed that some starting material still remained and therefore further N,N-dimethylformamide (2 drops) was added and stirring continued for 1 hour. The solvent was removed under reduced pressure and the residue azeotroped with anhydrous dichloromethane (×2). The residue was dissolved in anhydrous dichloromethane (200 ml) and the solution treated dropwise with ethylamine (2 M solution in tetrahydrofuran, 140 ml, 280 mmol). This solution was allowed to stand at room temperature for 48 hours. Diethyl ether (250 ml) was added and the mixture stirred for 15 minutes. The mixture was filtered and the solvent removed from the filtrate under reduced pressure. The residue was purified by column chromatography on silica gel eluting with a gradient system of dichloromethane gradually changing to dichloromethane:ethyl acetate (44:66, by volume) to afford the title compound as a yellow solid (24.70 g).

$^1$H-NMR (400 MHz, CDCl$_3$) δ: 6.53 (1H, br m), 5.12 (1H, dd), 5.07 (1H, d), 4.60 (1H, d), 4.54 (1H, dd), 3.46 (3H, s), 3.32 (2H, m), 1.51 (3H, s), 1.34 (3H, s), 1.15 (3H, t),

LRMS (thermospray): m/z [MH$^+$] 246.

Preparation 12

(2S,3S,4R,5R)- and (2S,3S,4R,5S)-N-ethyl-3,4-dihydroxy-5-methoxytetrahydro-2-furancarboxamide

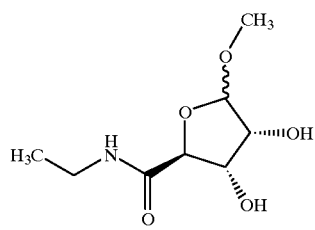

A solution of (3aS,4S,6R,6aR)-N-ethyl-6-methoxy-2,2-dimethyltetrahydrofuro[3,4-d][1,3]dioxole-4-carboxymide (Preparation 11) (24.60 g, 100 mmol) and pyridinium p-toluenesulphonate (2.50 g, 10 mmol) in methanol (500 ml) was heated under reflux for 18 hours. NMR analysis showed that some starting material still remained and therefore the solvent was removed under reduced pressure. The residue was dissolved in methanol (500 ml) and heated under reflux for 8 hours NMR analysis showed that some starting material still remained therefore the solvent was removed under reduced pressure, the residue dissolved in methanol (500 ml) and heating under reflux continued for 24 hours. The solvent was removed under reduced pressure and the residue azeotroped with dichloromethane (×3) to afford the title compound as an oil and as a mixture of α and β anomers (20.50 g).

$^1$H-NMR (400 MHz, CDCl$_3$) δ: 6.58 (1H, br m), 4.99 (0.25H, d), 4.94 (0.75H, d), 4.46 (0.25H, d), 4.37 (1.5H, m), 4.24 (0.25H, dd), 4.05 (1H, m), 3.52 (0.75H, s), 3.47 (2.25H, s), 3.30 (2H, m), 1.16 (3H, m).

Preparation 13

(2S,3S,4R,5R)- and (2S,3S,4R,5S)-4-(Benzoyloxy)-2-[(ethylamino)carbonyl]-5-methoxytetrahydro-3-furanyl benzoate

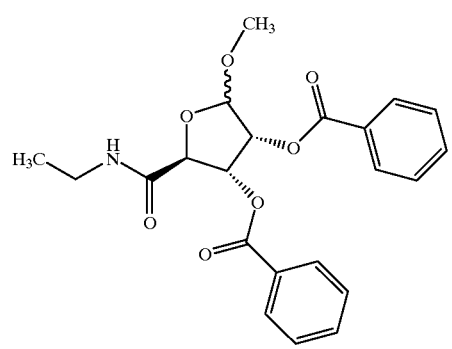

A solution of benzoyl chloride (30.0 ml, 259 mmol) in dichloromethane (100 ml) was added slowly to a solution of (2S,3S,4R,5R)- and (2S,3S,4R,5S)-N-ethyl-3,4-dihydroxy-5-methoxytetrahydro-2-furancarboxamide (Preparation 12) (20.50 g, 100 mmol) and pyridine (33.0 ml, 409 mmol) in dichloromethane (400 ml) and the resulting mixture was stirred at room temperature for 18 hours. The solvent was removed under reduced pressure and the residue partitioned between diethyl ether and aqueous hydrochloric acid (1 M, 300 ml). The layers were separated and the aqueous layer re-extracted with diethyl ether. The organic layers were combined, washed sequentially with water and brine, dried over anhydrous magnesium sulphate, filtered and the solvent removed under reduced pressure. The residue was purified by column chromatography on silica gel eluting with a gradient system of dichloromethane:diethyl ether (95:5, by volume) gradually changing to dichloromethane:diethyl ether (80:20, by volume) to afford the title compound as an oil and as a mixture of α and β anomers (37.0 g).

$^1$H-NMR (400 MHz, CDCl$_3$) δ: 8.16 (0.5H, d), 7.95 (1.5H, d), 7.88 (1.5H, d), 7.88 (1.5H, d), 7.81 (0.5H, d), 7.25–7.66 (6H, m), 6.65 (1H, br m), 5.88 (1H, m), 5.60 (0.75H, dd), 5.46 (0.25H, d), 5.23 (0.75H, d), 5.17 (0.25H, t), 4.80 (1H, m), 3.59 (2.25H, s), 3.49 (0.75H, s), 3.39 (2H, m), 1.23 (3H, t).

Preparation 14

(2S,3S,4R,5R)- and (2S,3S,4R,5S)-5-(Acetyloxy)-4-(benzoyloxy)-2-[(ethylamino)carbonyl]tetrahydro-3-furanyl benzoate

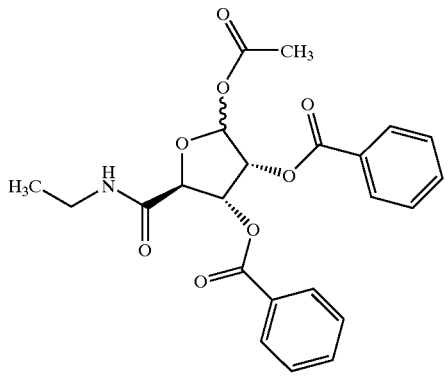

A solution of (2S,3S,4R,5R)- and (2S,3S,4R,5S)-4-benzoyloxy)-2-[(ethylamino)carbonyl]-5-methoxytetrahydro-3-furanyl benzoate (Preparation 13) (37.0 g, 89.6 mmol) in a mixture of acetic acid (330 ml, 5.77 mol) and acetic anhydride (67 ml, 709 mmol) was cooled to −10° C., then treated dropwise with aqueous hydrochloric acid (12 N, 7.0 ml, 132 mmol). The mixture was stirred for 18 hours during which time it was allowed to warm up to room temperature After cooling the mixture to 0° C., water (1000 ml) was added slowly to the mixture and then it was extracted with ethyl acetate (3×500 ml). The organic layers were combined, washed sequentially with water, a saturated aqueous solution of sodium hydrogen carbonate and brine, then dried over anhydrous magnesium sulphate, filtered and the solvent removed under reduced pressure. The residue was purified by column chromatography on silica gel eluting with a gradient system of diethyl ether:pentane (66:44, by volume) gradually changing to diethyl ether. The residue was further purified by column chromatography on silica gel eluting with a gradient system of dichloromethane:diethyl ether (95:5, by volume) gradually changing to dichloromethane:diethyl ether (90:10, by volume) to afford the title compound as a mixture of α and β anomers (15.40 g).

$^1$H-NMR (400 MHz, CDCl$_3$) δ: 8.12 (0.8H, d), 7.97 (1.2H, d), 7.92 (1.2H, d), 7.79 (0.8H, d), 7.24–7.65 (6H, m), 6.73 (0.4H, d), 6.62 (0.4H, br m), 6.46 (0.6H, br m), 6.42 (0.6H, d), 6.07 (0.4H, dd), 5.95 (0.6H, t), 5.72 (0.6H, d), 5.44 (0.4H, t), 4.94 (0.4H, d), 4.86 (0.6H, d), 3.36 (2H, m), 2.17 (1.8H, s), 2.10 (1.2H, s), 1.20 (3H, m).

Preparation 15

Methyl 9-{(2R,3R,4R,5R)-3,4-bis(acetyloxy)-5-[(acetyloxy)methyl]tetrahydro-2-furanyl}-6-[(2,2-diphenylethyl)amino]-9H-purine-2-carboxylate

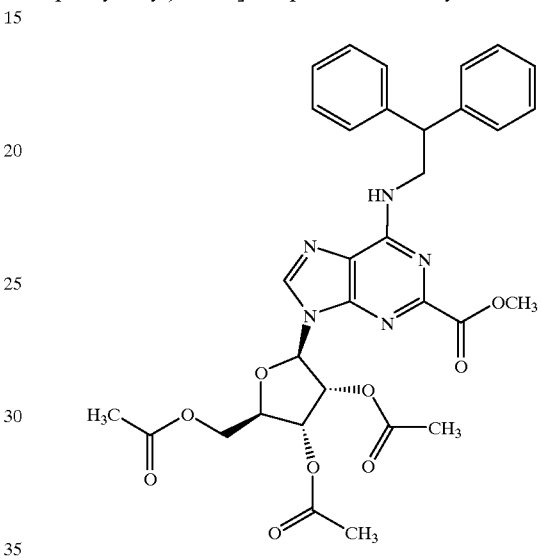

A suspension of methyl 6-[(2,2-diphenylethyl)amino]-9H-purine-2-carboxylate (Preparation 7) (1.5 g, 4.02 mmol) in 1,1,1-trichloroethane (40 ml) was treated with N,O-bis(trimethylsilyl)acetamide (4.8 ml, 19.6 mmol). The mixture was heated under reflux for two hours. The solution was allowed to cool to room temperature and the solvent removed under reduced pressure. The residue was taken up in anhydrous toluene (40 ml) and 1,2,3,5-tetra-O-acetyl-β-D-ribofuranose (1.65 g, 5.19 mmol) and trimethylsilyl trifluoromethanesulfonate (0.98 ml, 5.43 mmol) added. The resulting solution was heated under reflux under a nitrogen atmosphere for 3 hours. The mixture was cooled to room temperature, diluted with ethyl acetate (200 ml) and washed with a saturated aqueous solution of sodium hydrogen carbonate. The organic layer was separated, dried over anhydrous magnesium sulphate, filtered and the solvent removed under reduced pressure. The residue was purified by column chromatography on silica gel using gradient elution with ethyl acetate:pentane (70:30, by volume) then ethyl acetate:pentane (80:20, by volume) then ethyl acetate to afford the title compound as a foam (2.05 g).

$^1$H-NMR (400 MHz, CDCl$_3$) δ: 8.00 (1H, br s), 7.35–7.20 (11H, m), 6.25 (1H, m), 5.85–5.70 (3H, m), 4.50–4.30 (5H, m), 4.00 (3H, s), 2.15 (3H, s), 2.10 (3H, s), 2.05 (3H, s).

LRMS (thermospray): m/z [MNa$^+$] 655.

Preparation 16
Methyl 9-[(2R,3R,4S,5R)-3,4-dihydroxy-5-(hydroxymethyl)tetrahydro-2-furanyl]-6-[(2,2-diphenylethyl)amino]-9H-purine-2-carboxylate

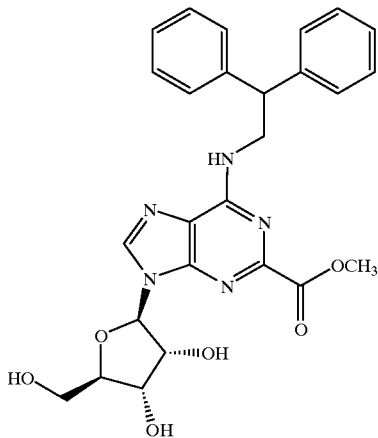

A solution of methyl 9-{(2R,3R,4R,5R)-3,4-bis(acetyloxy)-5-[(acetyloxy)methyl]-tetrahydro-2-furanyl}6-[(2,2-diphenylethyl)amino]-9H-purine-2-carboxylate (Preparation 15) (2.0 g, 3.17 mmol), sodium carbonate (35 mg) and dry methanol (40 ml) was stirred at room temperature for 3.5 hours. The solvent was removed under reduced pressure and the residue was purified by column chromatography on silica gel using a gradient elution with dichloromethane:methanol (94:6, by volume) then dichloromethane:methanol (92:8, by volume) to afford the title compound as a white powder (1.5 g).

$^1$H-NMR (400 MHz, CDCl$_3$) δ: 7.80 (1H, br s), 7.35–7.20 (10H, m), 5.95 (1H, br s), 5.75 (2H, m), 5.10 (1H, m), 4.90 (1H, br s), 4.40 (3H, m), 4.30 (1H, s), 4.15 (1H, m), 3.90 (1H, m), 3.80–3.70 (4H, m); 3.15 (1H, s).

LRMS (thermospray): m/z [MNa$^+$] 528.

Preparation 17
N-(2-Aminoethyl)-9-[(2R,3R,4S,5R)-3,4-dihydroxy-5-(hydroxymethyl)tetrahydro-2-furanyl]-6-[(2,2-diphenylethyl)amino]-9H-purine-2-carboxyamide

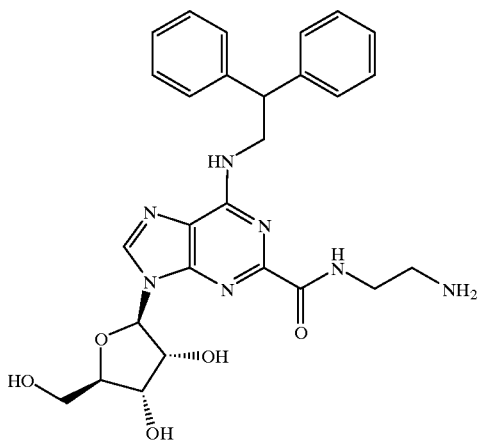

A mixture of methyl 9-[(2R,3R,4S,5R)-3,4-dihydroxy-5-(hydroxymethyl)tetrahydro-2-furanyl]-6-[(2,2-diphenylethyl)amino]-9H-purine-2-carboxyamide (Preparation 16) (0.52 g, 1.03 mmol) and 1,2-ethylenediamine (0.6 g, 10 mmol) was heated at 105° C. for 3 hours. The mixture was dissolved in a little dichloromethane and purified by column chromatography on silica gel eluting with dichloromethane:methanol:concentrated aqueous ammonia (85:15:1.5, by volume). After evaporation of appropriate fractions the residue was triturated with diethyl ether, filtered and dried to yield the target compound as a white solid, (0.43 g, 78%).

$^1$H-NMR (400 MHz, CDCl$_3$) δ: 8.00 (1H, s), 7.30–7.15 (12H, m), 5.85 (1H, d), 4.70 (1H, t), 4.40–4.30 (2H, m), 4.30–4.10 (3H, m), 3.95–3.85 (1H, m), 3.80–3.70 (1H, m), 3.50–3.40 (2H, m), 2.80 (2H, m).

LRMS (thermospray): m/z [MH$^+$] 534.

Preparation 18
N-[2-(1-Piperidinyl)ethyl]-1H-imidazole-1-carboxamide

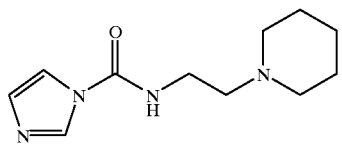

2-1-Piperidinyl)ethylamine (1.28 g, 10 mmol) was added to a stirred solution of N,N'-carbonyldimidazole (1.62 g, 10 mmol) in THF (25 ml) at room temperature. The reaction mixture was stirred overnight and the solvent removed by evaporation under reduced pressure. The residue was partitioned between ethyl acetate (100 ml) and water (50 ml), the ethyl acetate layer separated, washed with brine (30 ml) and dried (Na$_2$SO$_4$). Evaporation of solvent under reduced pressure yielded the title compound as a white solid (1.8 g).

$^1$H-NMR (400 MHz, CDCl$_3$) δ: 8.10 (1H, s), 7.35 (1H, s), 7.10 (1H, s), 6.80 (1H, br s), 3.45 (2H, m), 2.55 (2H, m), 2.50–2.30 (4H, m), 1.60–1.40 (6H, m).

Preparation 19
N-[2-(Diisopropylamino)ethyl]-1H-imidazole-1-carboxamide

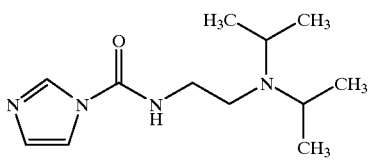

N$^1$,N$^1$-Diisopropyl-1,2-ethanediamine (1 g, 6.94 mmol) was added to a stirred solution of N,N'-carbonyldiimidazole (1.12 g, 6.94 mmol) in dichloromethane (50 ml) at room temperature. The reaction mixture was stirred for one hour and diluted with dichloromethane (50 ml), washed with water (60 ml), dried (anhydrous magnesium sulfate) and the solvent removed under reduced pressure. This gave the title compound as a white solid (600 mg)

$^1$H-NMR (400 MHz, CDCl$_3$) δ: 8.05 (1H, s), 7.25 (1H, s), 7.05 (1H, s), 6.65 (1H, br s), 3.40–3.35 (2H, m), 3.10–3.00 (2H, m), 2.75–2.70 (2H, m), 1.05–1.00 (6H, m).

Preparation 20

2-[2-(4-Isopropyl-1-piperidinyl)ethyl]-1H-isoindole-1,3(2H)-dione

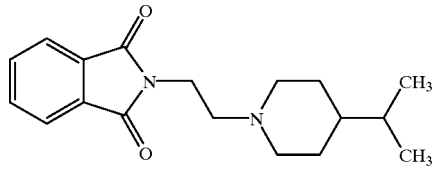

A solution of 4-isopropylpiperidine (3.3 g, 20.2 mmol), N-(2-bromoethyl)phthalimide (5.4 g, 21.3 mmol), potassium carbonate (5.9 g, 45.4 mmol) and acetonitrile (100 ml) and was heated under reflux for 2.5 hours then stirred at room temperature overnight. The solvent was removed under reduced pressure and the residue partitioned between ethyl acetate (100 ml) and water (100 ml). The organic layer was separated and the aqueous layer extracted with further ethyl acetate (100 ml). The combined organic extracts were dried ($Na_2SO_4$) and the solvent removed by evaporation under reduced pressure. The resulting oil was purified by column chromatography on silica gel eluting with a gradient system of dichloromethane changing to dichloromethane diethyl-:ether (50:50, by volume) changing to diethyl ether to afford the title compound (3.3 g).

$^1$H-NMR (400 MHz, $CDCl_3$) δ: 7.80 (2H, m), 7.70 (2H, m), 3.80 (2H, t), 3.00 (2H, m), 2.60 (2H, t), 1.95 (2H, m), 1.60 (2H, m), 1.40 (1H, m), 1.20 (2H, qd), 0.95 (1H, m), 0.80 (6H, d).

LRMS (thermospray): m/z [MH$^+$] 301.

Preparation 21

2-(4-Isopropyl-1-piperidinyl)ethylamine

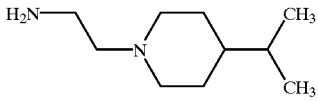

A solution of 2-[2-(4-isopropyl-1-piperidinyl)ethyl]-1H-isoindole-1,3(2H)-dione (Preparation 20) (3.2 g, 10.6 mmol) in a 33% w/w solution of methylamine in ethanol (60 ml) was heated under reflux for three hours. The solvent was removed under reduced pressure, further ethanol added (60 ml) and the solvent again removed under reduced pressure. The residue was suspended in dichloromethane (100 ml) and the solid filtered off. This was washed with dichloromethane (100 ml). The filtrate was evaporated under reduced pressure and the resulting oil purified by column chromatography on silica gel eluting with dichloromethane:methanol:0.88 aqueous $NH_3$ solution (90:10:1, by volume) to give a colourless oil. Bulb-to-bulb distillation (150–160° C., 4 kPa) yielded the title compound (1.0 g, 55%)

$^1$H-NMR (400 MHz, $CDCl_3$) δ: 2.90 (2H, m), 2.80 (2H, t), 2.40 (2H, t), 1.95 (2H, m), 1.65 (2H, m), 1.40 (1H, m), 1.30–1.20 (4H, m), 1.00 (1H, m), 0.85 (6H, d).

LRMS (thermospray): m/z [MH$^+$] 171.

Preparation 22

N-[2-(4-Isopropyl-1-piperidinyl)ethyl]-1H-imidazole-1-carboxamide

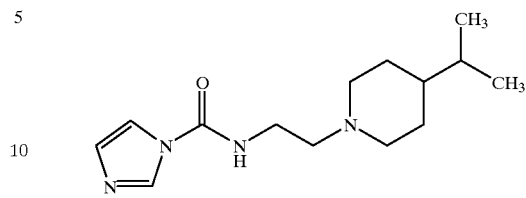

Prepared from 2-4-isopropyl-1-piperidinyl)ethylamine (Preparation 21) and N,N'-carbonyldiimidazole by a similar procedure to Preparation 19.

$^1$H-NMR (400 MHz, $CDCl_3$) δ: 8.10 (1H, s), 7.35 (1H, s), 7.10 (1H, s), 680 (1H, br s), 3.45 (2H, m), 2.55 (2H, m), 2.50–2.30 (4H, m), 1.60–1.40 (6H, m).

Preparation 23

N-Isopropylcyclopentanamine

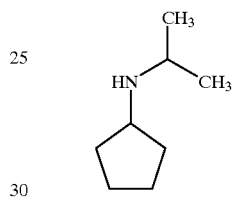

Pearlman's catalyst (20% w/w palladium hydroxide-on-carbon) (1.5 g) was added to a solution of cyclopentylamine (15 ml, 0.21 mol) in acetone (200 ml). The reaction mixture was stirred under an atmosphere of hydrogen gas at 414 kPa (60 psi). After stirring for 16 hours the reaction mixture was filtered through Arbocel (trade mark) and the solvent removed under reduced pressure to give the title compound (15 ml) as a thin oil.

$^1$H-NMR (400 MHz, $CDCl_3$) δ: 3.20–3.10 (1H, m), 2.90–2.80 (1H, m), 1.95–1.85 (2H, m), 1.75–1.45 (4H, m), 1.35–1.20 (2H, m), 1.10–1.00 (6H, m).

Preparation 24

[Cyclopentyl(isopropyl)amino]acetonitrile

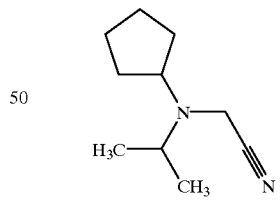

Hydroxyacetonitrile (82 ml of a 70% w/w solution in water, 0.1 mol) was added to a solution of N-isopropylcyclopentanamine (11.43 g, 0.09 mol) (Preparation 23) in ethanol (60 ml). The reaction mixture was heated under reflux for 3 hours, allowed to cool and the solvent removed under reduced pressure. The residue was purified by chromatography on silica gel eluting with dichloromethane:methanol (98:2, by volume) to give the title compound (14.1 g) as a clear oil.

$^1$H-NMR (400 MHz, $CDCl_3$) δ: 3.60–3.50 (2H, s), 3.30–3.20 (2H, m), 2.00–1.85 (2H, m), 1.80–1.55 (4H, m), 1.45–1.30 (2H, m), 1.15–1.05 (6H, m).

Preparation 25
N$^1$-Cyclopentyl-N$^1$-isopropyl-1,2-ethanediamine

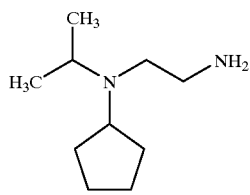

Lithium aluminium hydride (66 ml of a 1 molar solution in tetrahydrofuran, 0.066 mol) was added to a stirred solution of [cyclopentyl(isopropyl)amino]acetonitrile (10 g, 0.66 mol) (Preparation 24) in tetrahydrofuran (100 ml) at 0° C. The reaction mixture was stirred at 0° C. for 20 minutes and then heated under reflux for 2 hours. The reaction mixture was allowed to cool to room temperature and left to stand overnight. The reaction mixture was cooled in an icebath and treated dropwise with 4.8 ml of a 7.5% w/w aqueous sodium hydroxide solution followed by 7.4 ml of water. The solvent was removed under reduced pressure and the residue slurried with diethyl ether (200 ml) for 30 minutes and then filtered. The filtrate was evaporated under reduced pressure to give the title compound as a colourless oil (10.30 g).

$^1$H-NMR (400 MHz, CDCl$_3$) δ: 3.10–2.95 (2H, m), 2.70–2.60 (2H, m), 2.50–2.40 (2H, m), 1.80–1.45 (10H, m), 1.05–0.95 (6H, m).

LRMS (thermospray): m/z [MH$^+$] 171.

Preparation 26
N-{2-[Cyclopentyl(isopropyl)amino]ethyl}-1H-imidazole-1-carboxamide

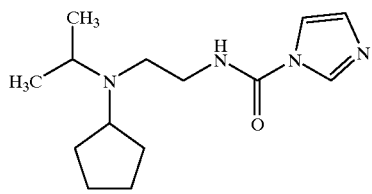

Prepared from N$^1$-Cyclopentyl-N$^1$-isopropyl-1,2-ethanediamine (Preparation 25) and N,N'-carbonyldiimidazole a similar method to Preparation 19.

$^1$H-NMR (400 MHz, CDCl$_3$) δ: 8.10 (1H, s), 7.35 (1H, s), 7.10 (1H, s), 6.80 (1H, br s), 3.45 (2H, m), 2.55 (2H, m), 2.50–2.30 (4H, m), 1.60–1.40 (6H, m).

Preparation 27
[Cyclohexyl(isopropyl)amino]acetonitrile

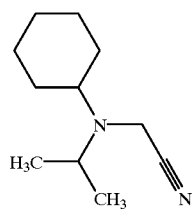

Prepared from N-isopropylcyclohexylamine and hydroxyacetonitrile by a similar method to Preparation 24.

$^1$H-NMR (400 MHz, CDCl$_3$) δ: 3.55 (2H, s), 3.20 (1H, m), 2.65 (1H, m), 1.85–1.70 (4H, m), 1.30–1.20 (4H, m), 1.10 (8H, m).

Preparation 28
N$^1$-Cyclohexyl-N$^1$-isopropyl-1,2-ethanediamine

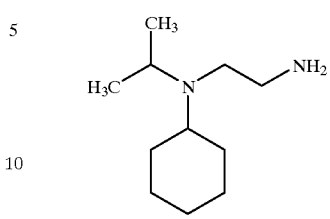

Prepared from [cyclohexyl(isopropyl)amino]acetonitrile (Preparation 27) by a similar method to Preparation 25.

$^1$H-NMR (400 MHz, CDCl$_3$) δ: 3.00 (1H, m), 2.60 (2H, m), 2.50 (2H, m), 2.40 (1H, br s), 1.75–1.65 (4H, m), 1.25–1.10 (4H, m), 1.05–0.90 (8H, m).

Preparation 29
N-{2-[Cyclohexyl(isopropyl)amino]ethyl}-1H-imidazole-1-carboxamide

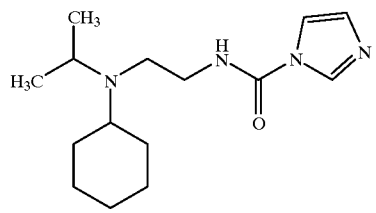

Prepared from N$^1$-cyclohexyl-N$^1$-isopropyl-1,2-ethanediamine (Preparation 28) and N,N'-carbonyldiimidazole by a similar method to Preparation 19.

$^1$H-NMR (400 MHz, CDCl$_3$) δ: 8.05 (1H, s), 7.30 (1H, s), 7.10 (1H, s), 6.65 (1H, br s), 3.40 (2H, m), 3.10 (2H, m), 2.75 (2H, m), 2.45 (1H, m), 1.80–1.60 (4H, m), 1.30–1.20 (4H, m), 1.10–1.00 (8H, m).

Preparation 30
N-[1-(2-Pyridinyl)-4-piperidinyl]-1H-imidazole-1-carboxamide

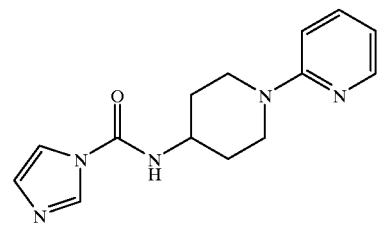

Prepared from 1-(2-pyridinyl)-4-aminopiperidine (WO 99/65895) and N,N'-carbonyldiimidazole by a similar method to Preparation 19.

$^1$H-NMR (400 MHz, CDCl$_3$) δ: 8.15 (1H, m), 8.05 (1H, s), 7.45 (1H, m), 7.20 (1H, s), 7.00 (1H, s), 6.65 (1H, m), 6.55 (1H, m), 5.90 (1H, d), 4.25 (2H, d), 4.05 (1H, m), 2.95 (2H, t), 2.10 (2H, d), 1.55 (2H, t).

Preparation 31
N-(3-Aminopropyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

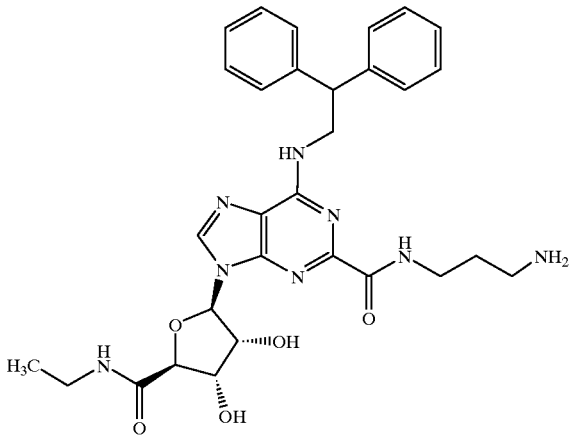

A mixture of methyl 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylate (Preparation 9) (0.35 g, 0.64 mmol) and 1,3-diaminopropane (0.45 g, 6.1 mmol) was heated at 100° C. for 3 hours. The mixture was dissolved in a little dichloromethane and purified by column chromatography on silica gel eluting with a gradient system of dichloromethane:methanol:concentrated aqueous ammonia (80:20:1.2, by volume) changing to dichloromethane:methanol:concentrated aqueous ammonia (88:12:2, by volume). After evaporation of appropriate fractions the residue was triturated with diethyl ether, filtered and dried to yield the target compound as a white solid, (0.22 g, 58%).

$^1$H-NMR (400 MHz, CDCl$_3$) δ: 8.40 (1H, br s), 7.35–7.15 (10H, m), 6.30 (1H, m), 4.70–4.50 (3H, m), 4.40–4.20 (3H, m), 3.50 (2H, m), 3.30 (2H, m), 2.85 (2H, m), 1.80 (2H, m), 1.10 (3H, t).

LRMS: m/z [MH$^+$] 590.

Preparation 32
Trans-N-(4-Aminocyclohexyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

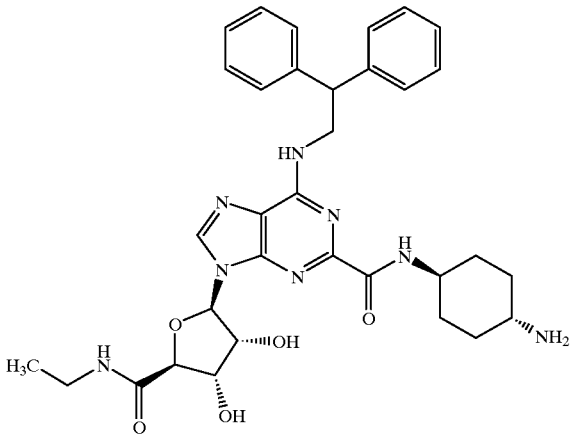

A mixture of methyl 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylate (Preparation 9) (0.35 g, 0.64 mmol) and trans-1,4-diaminocyclohexane (0.6 g, 6.14 mmol) was heated at 105° C. for 3 hours. The mixture was dissolved in a little dichloromethane and purified by column chromatography on silica gel eluting with a gradient system of dichloromethane:methanol:concentrated aqueous ammonia (80:20:1.2, by volume) changing to dichloromethane:methanol:concentrated aqueous ammonia (88:12:2, by volume). After evaporation of appropriate fractions the residue was triturated with diethyl ether, filtered and dried to yield the target compound as a white solid, (0.32 g, 79%).

$^1$H-NMR (400 MHz, CDCl$_3$) δ: 8.80 (1H, br s), 8.10 (1H, m), 7.60 (1H, m), 7.40–7.20 (10H, m), 7.00 (1H, m), 6.15 (1H, m), 5.15 (1H, m), 4.50 (1H, m), 4.40–4.20 (3H, m), 3.80 (1H, m), 3.40 (2H, m), 2.75 (1H, m), 2.10 (2H, m), 1.95 (2H, m), 1.40–1.20 (7H, m).

LRMS: m/z [MH$^+$] 630.

Preparation 33
N-(1-Benzyl-4-piperidinyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

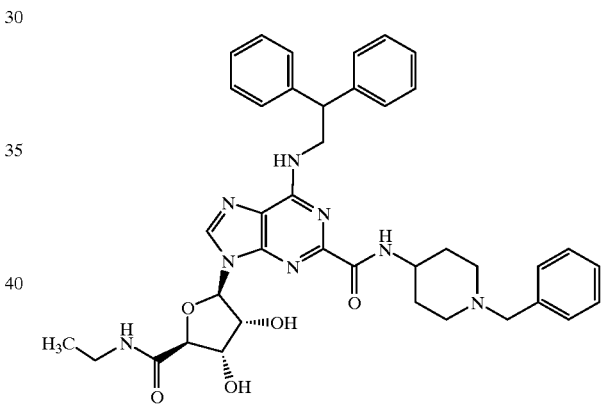

A mixture of methyl 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylate (Preparation 9) (1.0 g, 1.83 mmol) and 1-benzyl-4-piperidinylamine (2.4 ml, 11 mmol) was heated at 105 ° C. for 4 hours. The mixture was dissolved in a little dichloromethane and purified by column chromatography on silica gel eluting with a gradient system of dichloromethane:methanol (98:2, by volume) changing to dichloromethane:methanol (95:5, by volume). After evaporation of appropriate fractions the residue was triturated with diethyl ether, filtered and dried to yield the target compound as a white solid, (1.0 g, 80%).

$^1$H-NMR (400 MHz, d$_6$-DMSO) δ: 8.45 (1H, br s), 8.30 (2H, m), 8.20 (1H, m), 7.40–7.10 (15H, m), 5.95 (1H, m), 5.60 (1H, m), 5.50 (1H, m), 4.60–4.50 (2H, m), 4.25 (1H, s), 4.20–4.10 (3H, m), 3.80 (1H, m), 3.40 (2H, m), 3.20 (2H,

Preparation 34
N-[(3R)-1-Benzylpyrrolidinyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

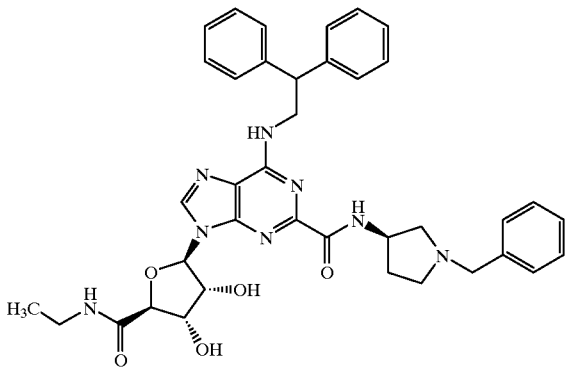

Prepared from methyl 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylate (Preparation 9) and (3R)-1-benzylpyrrolidinylamine by a similar procedure to Preparation 33. The target compound was obtained as a white solid.

$^1$H-NMR (400 MHz, CD$_3$OD) δ: 8.40 (1H, br s), 7.40–7.10 (15H, m), 6.10 (1H, m), 4.60–4.30 (7H, m), 3.60 (2H, m), 3.30 (2H, m), 2.90–2.60 (3H, m), 2.50–2.30 (2H, m), 1.80 (1H, m), 1.05 (3H, t).

LRMS: m/z [M-H$^+$] 689.

Preparation 35
N-[(3S)-1-Benzylpyrrolidinyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide

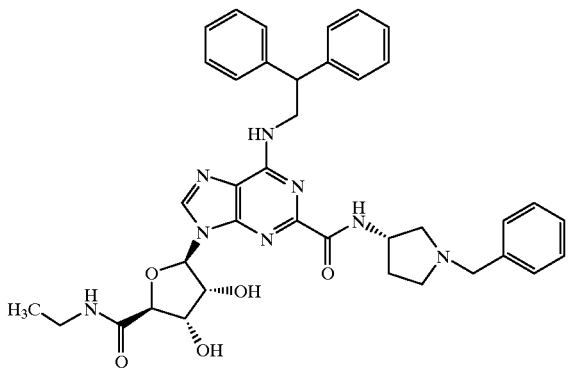

Prepared from methyl 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylate (Preparation 9) and (3S)-1-benzylpyrrolidinylamine by a similar procedure to Preparation 33. The target compound was obtained as a white solid.

$^1$H-NMR (400 MHz, CD$_3$OD) δ: 8.35 (1H, br s), 7.40–7.10 (15H, m), 6.05 (1H, m), 4.80 (1H, m), 4.60–4.30 (6H, m), 3.60 (2H, m), 3.30–3.20 (2H, m), 2.85 (1H, m), 2.75 (1H, m), 2.65 (1H, m), 2.50–2.30 (2H, m), 1.80 (1H, m), 0.95 (3H, t).

LRMS: m/z [M-H$^+$] 689.

Preparation 36
6-[(2,2-diphenylethyl)amino]-9-{(2R,3R,4S,5S)-5-[(ethylamino)carbonyl]-3,4-dihydroxytetrahydro-2-furanyl}-N-(4-piperidinyl)-9H-purine-2-carboxamide

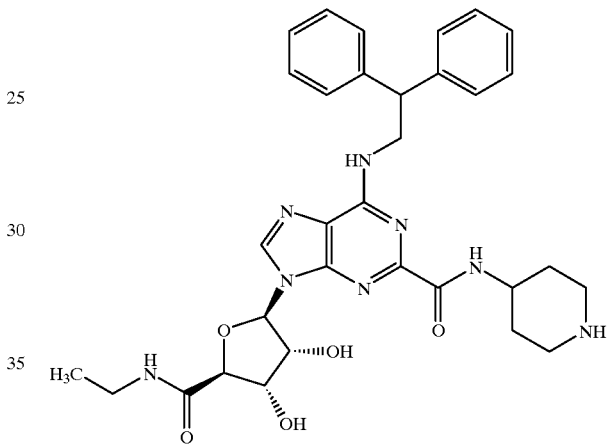

A solution of N-(1-benzyl-4-piperidinyl)-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 33) (1.03 g, 1.47 mmol), palladium (II) hydroxide (0.9 g) and ammonium formate (0.46 g, 7.3 mmol) in ethanol (10 ml) was heated under reflux for 3 hours. The catalyst was removed by filtration through Arbocel (trade mark), solvent removed by evaporation under reduced pressure and the residue purified by column chromatography on silica gel eluting with a gradient system of dichloromethane:methanol:concentrated aqueous ammonia (90:10:1, by volume) changing to dichloromethane:methanol:concentrated aqueous ammonia (80:20:2, by volume). After evaporation of appropriate fractions the target compound was obtained as a white solid, (0.6 g, 67%).

$^1$H-NMR (400 MHz, d$_6$-DMSO) δ: 8.45 (1H, br s), 8.30 (2H, m), 8.20 (1H, m), 7.40–7.10 (15H, m), 5.95 (1H, m), 5.70–5.50 (2H, m), 4.70–4.50 (2H, m), 4.25 (1H, s), 4.20–4.10 (3H, m), 3.80 (1H, m), 3.20 (2H, m), 2.95 (2H, m), 2.55 (2H, m), 1.80 (2H, m), 1.40 (2H, m), 0.90 (3H, m).

LRMS: m/z [MH$^+$] 615.

Preparation 37
6-[(2,2-Diphenylethyl)amino]-9-{(2R,3R,4S,5S)-5-[(ethylamino)carbonyl]-3,4-dihydroxytetrahydro-2-furanyl}-N-[(3R)-pyrrolidinyl]-9H-purine-2-carboxamide

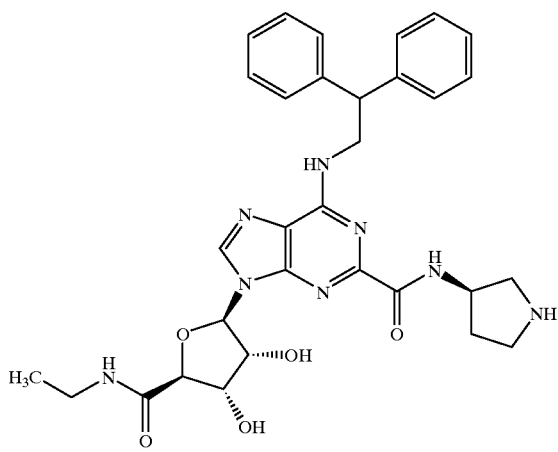

Prepared from N-[(3R)-1-benzylpyrrolidinyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 34) by a similar procedure to Preparation 36. The target compound was obtained as a white solid.

$^1$H-NMR (400 MHz, CD$_3$OD) δ: 8.40 (1H, br s), 7.35–7.10 (10H, m), 6.10 (1H, m), 4.60–4.30 (6H, m), 3.40 (2H, m), 3.30–3.20 (2H, m), 2.35 (1H, m), 2.10 (1H, m), 1.25 (2H, m), 1.00 (3H, t).
LRMS: m/z [M-H$^+$] 599.

Preparation 38
6-[(2,2-Diphenylethyl)amino]-9-{(2R,3R,4S,5S)-5-[(ethylamino)carbonyl]-3,4-dihydroxytetrahydro-2-furanyl}-N-[(3S)-pyrrolidinyl]-9H-purine-2-carboxamide

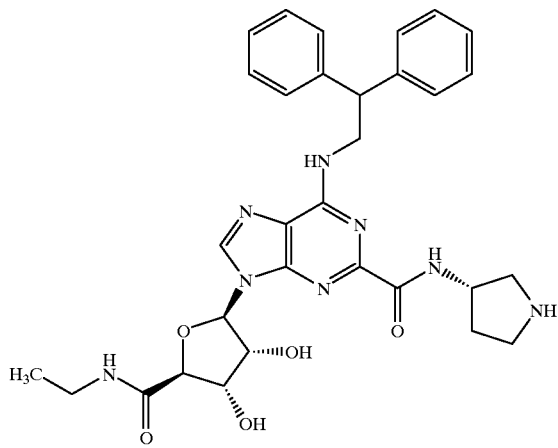

Prepared from N-[(3S)-1-benzylpyrrolidinyl]-6-[(2,2-diphenylethyl)amino]-9-{(2R,3R,4S,5S)-5-[(ethylamino)carbonyl]-3,4-dihydroxytetrahydro-2-furanyl}-9H-purine-2-carboxamide (Preparation 35) by a similar procedure to Preparation 36. The target compound was obtained as a white solid.

$^1$H-NMR (400 MHz, CD$_3$OD) δ: 8.40 (1H, br s), 7.35–7.10 (10H, m), 6.10 (1H, m), 4.55–4.25 (6H, m), 3.30–3.20 (2H, m), 3.00 (2H, m), 2.30 (1H, m), 1.90 (1H, m), 1.25 (2H, m), 1.00 (3H, t).
LRMS: m/z [MH$^+$] 601.

Preparation 39
6-[(2,2-Diphenylethyl)amino]-9-{(2R,3R,4S,5S)-5-[(ethylamino)carbonyl]-3,4-dihydroxytetrahydro-2-furanyl}-9H-purine-2-carboxylic acid

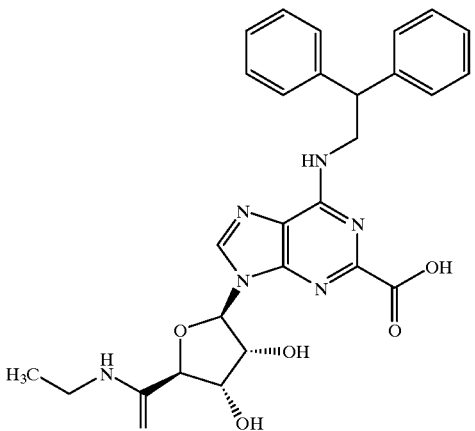

A solution of methyl 6-[(2,2-diphenylethyl)amino]-9-{(2R,3R,4S,5S)-5-[(ethylamino)carbonyl]-3,4-dihydroxytetrahydro-2-furanyl}-9H-purine-2-carboxylate (Preparation 9) (0.7 g, 1.28 mmol) and 10% w/w aqueous sodium hydroxide solution (1.3 ml, 3.2 mmol) in methanol (2.3 ml) was stirred at room temperature for 14 hours. The solution was adjusted to pH 4 by the addition of 2N aqueous hydrochloric acid and the precipitated white solid collected by filtration. The solid was washed with water and dried under reduced pressure to give the target compound as a white powder, (0.21 g, 30%).

$^1$H-NMR (400 MHz, d$_6$-DMSO) δ: 8.65–8.45 (1H, m), 8.35 (1H, br s), 8.05 (1H, br s), 7.40–7.10 (10H, m), 6.05–5.95 (1H, m), 5.70 (1H, br s), 4.60–4.40 (2H, m), 4.30–4.10 (3H, m), 3.20 (2H, m), 0.90 (3H, t).
LRMS: m/z [MH$^+$] 615.

Preparation 40
(2S,3S,4R,5R)-5-[6-[(2,2-Diphenylethyl)amino]-2-{4-[(trifluoroacetyl)amino]-1-piperidinyl}carbonyl)-9H-purin-9-yl]-N-ethyl-3,4-dihydroxytetrahydro-2-furancarboxamide

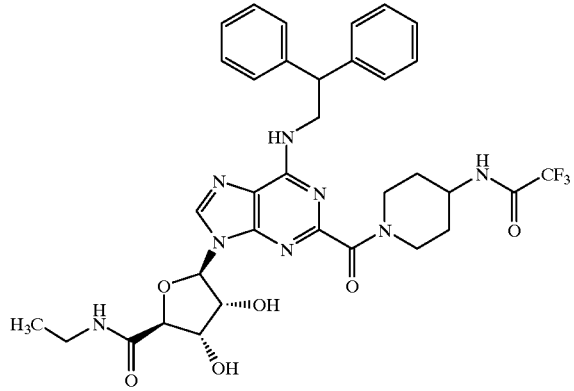

A solution of 6-[(2,2-diphenylethyl)amino]-9-{(2R,3R,4S,5S)-5-[(ethylamino)carbonyl]-3,4-dihydroxytetrahydro-2- furanyl}-9H-purine-2-carboxylic acid (Preparation 39) (0.2 g, 0.38 mmol), 2,2,2-trifluoro-N-(4-piperidinyl)acetamide (83 mg, 0.42 mmol) and 1-(3-dimethylaminopropyl)-3-ethylcarbodiimide hydrochloride (81 mg, 0.42 mmol) in dichloromethane (5 ml) was stirred at room temperature for 48 hours and then heated under reflux for a further 96 hours. The solution was allowed to cool to room temperature and then solvent removed by evaporation under reduced pressure. The residue was purified by column chromatography on silica gel eluting with a gradient system of dichloromethane:methanol:concentrated aqueous ammonia (95:5:1, by volume) changing to dichloromethane:methanol:concentrated aqueous ammonia (80:20:1, by volume). After evaporation of appropriate fractions the target compound was obtained as a white solid, (43 mg, 18%).

$^1$H-NMR (400 MHz, CD$_3$OD) δ: 8.20 (1H, s), 7.30–7.10 (10H, m), 5.95 (1H, m), 4.60 (2H, m), 4.50–4.40 (2H, m), 4.30–4.20 (3H, m), 4.00 (1H, m), 3.65 (1H, m), 3.20 (2H, m), 2.95 (1H, m), 2.00 (1H, m), 1.90 (1H, m), 1.60 (2H, m), 1.05 (3H, t).

LRMS: m/z [M-H$^+$] 709.

Preparation 41

(2S,3S,4R,5R)-5-{2-[(4-amino-1-piperidinyl)carbonyl]6-[(2,2-diphenylethyl)amino]-9H-purin-9-yl}-N-ethyl-3,4-dihydroxytetrahydro-2-furancarboxamide

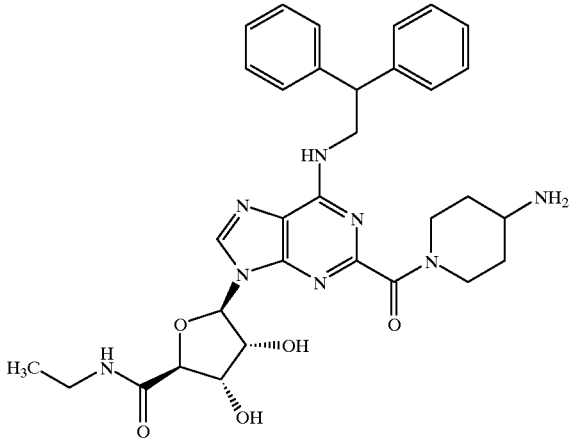

A solution of (2S,3S,4R,5R)-5-[6-[(2,2-diphenylethyl)amino]-2-{4-[(trifluoroacetyl)amino]-1-piperidinyl}carbonyl)-9H-purin-9-yl]-N-ethyl-3,4-dihydroxytetrahydro-2-furancarboxamide (Preparation 40) (40 mg, 0.056 mmol) in methanol (1 ml) and concentrated aqueous ammonia solution (0.5 ml) was stirred at room temperature for 48 hours. Solvent was removed by evaporation under reduced pressure to give the target compound as a white solid, (35 mg).

$^1$H-NMR (400 MHz, CD$_3$OD) δ: 8.25 (1H, s), 7.30–7.10 (10H, m), 6.00 (1H, m), 4.70–4.60 (2H, m), 4.50–4.40 (2H, m), 4.30–4.10 (3H, m), 3.70 (1H, m), 3.40 (1H, m), 3.20 (2H, m), 2.95 (1H, m), 2.10 (1H, m), 1.95 (1H, m), 1.60 (2H, m), 1.05 (3H, t).

LRMS: m/z [MH$^+$] 615.

Preparation 42

N-[(3R)-1-Benzylpyrrolidinyl]-N'-[2-(diisopropylamino)ethyl]urea

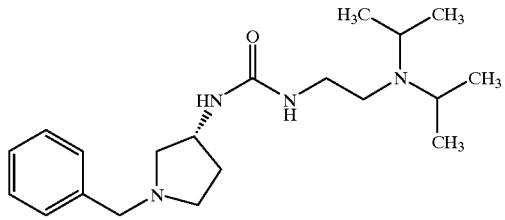

(3R)-1-Benzylpyrrolidinylamine (0.5 g, 2.84 mmol) was added to a stirred solution of N-[2-(diisopropylamino)amino)ethyl]-1H-imidazole-1carboxamide (Preparation 19) (0.68 g, 2.84 mmol) in 1,1,1-trichloroethane (2.5 ml) and isopropanol (2.5 ml)and the reaction mixture heated under reflux for four hours. The solution was allowed to cool to room temperature and solvent removed by evaporation under reduced pressure. The residue was purified by column chromatography on silica gel eluting with a gradient system of dichloromethane:methanol:concentrated aqueous ammonia (95:5:0.5, by volume) changing to dichloromethane:methanol:concentrated aqueous ammonia (90:10:2, by volume). After evaporation of appropriate fractions the target compound was obtained as a white solid, (0.98 g).

$^1$H-NMR (400 MHz, CD$_3$OD) δ: 7.30–7.20 (5H, m), 4.15 (1H, m), 3.60–3.50 (2H, m), 3.30–3.20 (2H, m), 3.10–3.00 (4H, m), 2.80–2.65 (2H, m), 2.55–2.30 (4H, m), 2.20 (1H, m), 1.55 (1H, m), 1.00 (12H, d).

LRMS: m/z [MH$^+$] 348.

Preparation 43

N-[(3S)-1-Benzylpyrrolidinyl]-N'-[2-(diisopropylamino)ethyl]urea

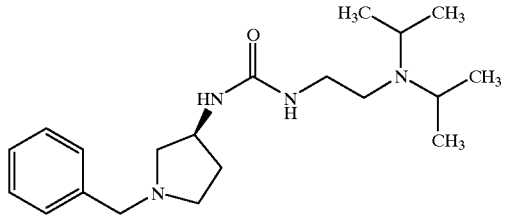

Prepared from (3S)-1-Benzylpyrrolidinylamine and N-[2-diisopropylamino)ethyl]-1H-imidazole-1-carboxamide (Preparation 19) by the same method as Preparation 42. The target compound was obtained as a white solid.

$^1$H-NMR (400 MHz, CD$_3$OD) δ: 7.30–7.20 (5H, m), 4.15 (1H, m), 3.60–3.50 (2H, m), 3.30–3.20 (2H, m), 3.10–3.00 (4H, m), 2.80–2.65 (2H, m), 2.55–2.30 (4H, m), 2.20 (1H, m), 1.55 (1H, m), 1.00 (12H, d).

LRMS: m/z [MH$^+$] 348.

Preparation 44
N-[2-(Diisopropylamino)ethyl]-N'-[(3R)-pyrrolidinyl]urea

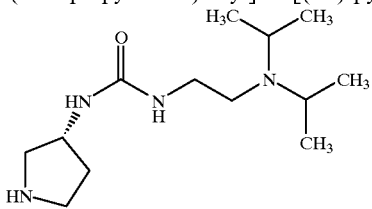

A solution of N-[(3R)-1-benzylpyrrolidinyl]-N'-[2-diisopropylamino)ethyl]urea (Preparation 42) (1.10 g, 3.16 mmol), palladium (II) hydroxide (1.0 g) and ammonium formate (1.0 g, 16 mmol) in ethanol (10 ml) was heated under reflux for 2 hours. The catalyst was removed by filtration through Arbocel (trade mark) and solvent removed by evaporation under reduced pressure to give the target compound as a white solid, (0.6 g, 67%).
$^1$H-NMR (400 MHz, CD$_3$OD) δ: 4.15 (1H, m), 3.20–2.90 (7H, m), 2.70–2.55 (3H, m), 2.10 (1H, m), 1.65 (1H, m), 1.10 (12H, d).
LRMS: m/z [MH$^+$] 258.

Preparation 45
N-[2-(Diisopropylamino)ethyl]-N'-[(3S)-pyrrolidinyl]urea

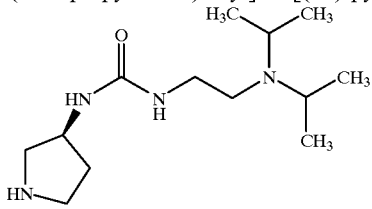

Prepared from N-[(3S)-1-Benzylpyrrolidinyl]-N'-[2-diisopropylamino)ethyl]urea (Preparation 43) by the same method as Preparation 44. The target compound was obtained as a white solid.
$^1$H-NMR (400 MHz, CD$_3$OD) δ: 4.15 (1H, m), 3.20–2.90 (7H, m), 2.70–2.55 (3H, m), 2.10 (1H, m), 1.65 (1H, m), 1.10 (12H, d).
LRMS: m/z [MH$^+$] 258.

Preparation 46
(2R,3R,4S,5S)-2-(2-amino-6-chloro-9H-purin-9-yl)-4-(benzoyloxy)-5-[(ethylamino)carbonyl]-tetrahydro-3-furanyl benzoate

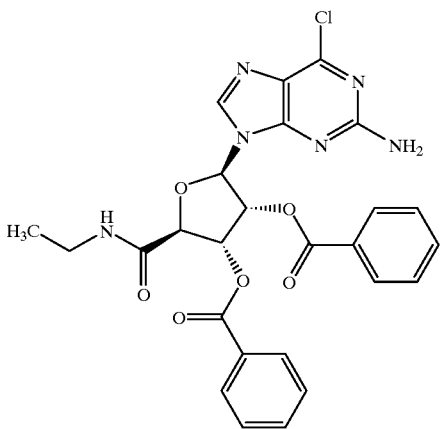

A suspension of 2-amino-6-chloropurine (4.60 g, 27.13 mmol) in 1,1,1-trichloroethane (230 ml) was treated with N,O-bis(trimethylsilyl)acetamide (20 ml, 81.4 mmol). The mixture was heated under reflux for 6 hours. The solution was allowed to cool to room temperature and the solvent was removed under reduced pressure. The residue was treated with a solution of (2S,3S,4R,5R)- and (2S,3S,4R,5S)-5-acetyloxy)-4-benzoyloxy)-2-[(ethylamino)carbonyl] tetrahydro-3-furanyl benzoate (Preparation 14) (14.39 g, 32.6 mmol) in anhydrous toluene (230 ml) and trimethylsilyl trifluoromethanesulfonate (20 ml, 108.5 mmol). The resulting solution was then heated at 90° C. under a nitrogen atmosphere for 90 minutes. The mixture was cooled to room temperature, diluted with ethyl acetate (250 ml) and washed with a saturated aqueous solution of sodium hydrogen carbonate (350 ml) then brine (350 ml). The organic layer was separated, dried over anhydrous magnesium sulfate, filtered and evaporated under reduced pressure. The residue was purified by column chromatography on silica gel eluting with dichloromethane:methanol (98:2 by volume) to afford the title compound as a foam (8.1 g).
$^1$H-NMR (400 MHz, CDCl$_3$) δ: 8.10–7.95 (3H, m), 7.80 (2H, m), 7.50–7.30 (6H, m), 6.90 (1H, m), 6.40–6.20 (3H, m), 5.20 (2H, br s), 4.90 (1H, m), 3.45 (1H, m), 3.30 (1H, m), 1.15 (3H, t).
LRMS: m/z [MH$^+$] 552.

Preparation 47
(2R,3R,4S,5S)-4-(Benzoyloxy)-2-(6-chloro-2-iodo-9H-purin-9-yl)-5-[(ethylamino)carbonyl]-tetrahydro-3-furanyl benzoate

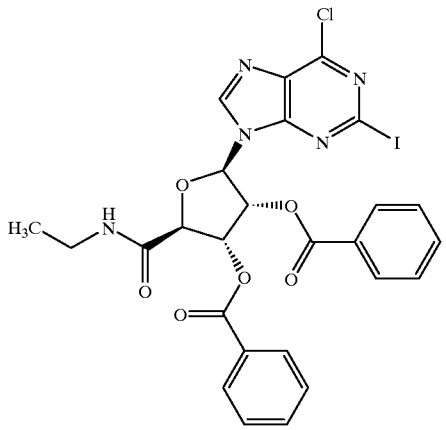

n-Butyl nitrite (4.65 ml, 39.7 mmol) was added to a suspension of (2R,3R,4S,5S)-2-2-amino-6-chloro-9H-purin-9-yl)-4-(benzoyloxy)-5-[(ethylamino)carbonyl]-tetrahydro-3-furanyl benzoate (Preparation 46) (8.10 g, 14.7 mmol), iodine (3.73 g, 14.7 mmol), copper(I) iodide (6.16 g, 32.3 mmol) and diiodomethane (12.55 ml, 155.8 mmol) in THF (100 ml) and the mixture was heated under reflux for 2.5 hours. The solution was allowed to cool to room temperature and the solvent was removed under reduced pressure. The residue was partitioned between aqueous sodium metabisulfite solution (5% w/v, 1 00 ml) and dichloromethane (100 ml). The organic layer was separated, filtered through Arbocel (trade mark), dried over anhydrous magnesium sulfate and solvent evaporated under reduced pressure. The residue was purified by column chromatography on silica gel eluting with dichloromethane:methanol (99:1, by volume) to afford the title compound as a yellow foam (7.55 g, 78%)
$^1$H-NMR (400 MHz, CDCl$_3$) δ: 8.55 (1H, s), 8.05 (2H, m), 7.80 (2H, m), 7.65–7.30 (6H, m), 6.75 (1H, m), 6.50 (1H, m), 6.10–6.00 (2H, m), 4.90 (1H, m), 3.60–3.40 (2H, m), 1.25 (3H, t).
LRMS:m/z [MNa$^+$] 684.

Preparation 48
(2R,3R,4S,5S)-4-(Benzoyloxy)-2-(6-{[2,2-bis(3-methylphenyl)ethyl]amino}-2-iodo-9H-purin-9-yl)-5-[(ethylamino)carbonyl]-tetrahydro-3-furanyl benzoate

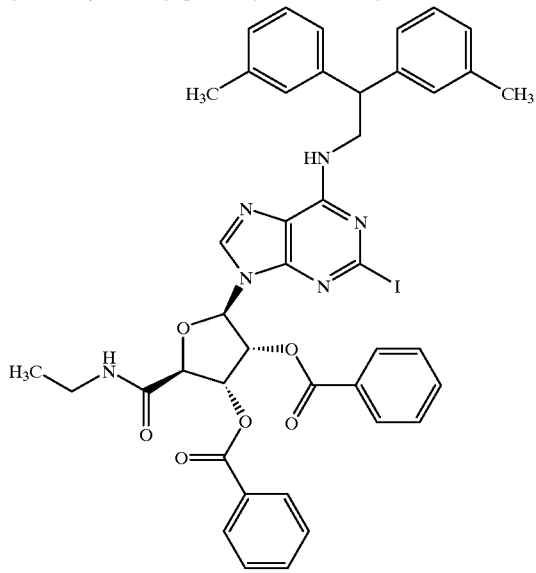

A solution of ((2R,3R,4S,5S)-4-benzoyloxy)-2-6-chloro-2-iodo-9H-purin-9-yl )-5-[(ethylamino)carbonyl]-tetrahydro-3-furanyl benzoate (Preparation 47) (0.6 g, 0.91 mmol) and 2,2-bis(3-methylphenyl)ethylamine (0.3 g, 1.36 mmol) in isopropanol (20 ml) was stirred at room temperature for 48 hours. Solvent was removed under reduced pressure and the residue purified by column chromatography on silica gel eluting with dichloromethane:methanol (99:1, by volume) to afford the title compound as a beige foam (0.67 g, 87%).
$^1$H-NMR (400 MHz, CDCl$_3$) δ: 8.00 (2H, m), 7.75 (3H, m), 7.60–7.40 (5H, m), 7.25 (1H, m), 7.15 (1H, m), 7.10–7.00 (7H, m), 6.20–6.00 (3H, m), 4.85 (1H, m), 4.25–4.10 (3H, m), 3.65 (1H, m), 3.50 (1H, m), 2.30 (6H, s), 1.20 (3H, t).
LRMS: m/z [MH$^+$] 852.

Preparation 49
(2R,3R,4S,5S)-4-(Benzoyloxy)-2-(6-{[2,2-bis(3-chlorophenyl)ethyl]amino}-2-iodo-9H-purin-9-yl)-5-[(ethylamino)carbonyl]-tetrahydro-3-furanyl benzoate

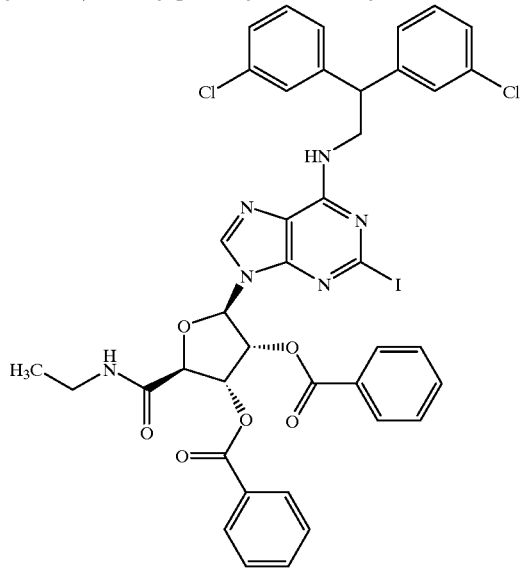

Prepared from ((2R,3R,4S,5S)-4-benzoyloxy)-2-6-chloro-2-iodo-9H-purin-9-yl)-5-[(ethylamino)carbonyl]-tetrahydro-3-furanyl benzoate (Preparation 47) and 2,2-bis(3-chlorophenyl)ethylamine by the same method as Preparation 48. The title compound was obtained as a yellow foam.
$^1$H-NMR (400 MHz, CDCl$_3$) δ: 8.00 (2H, m), 7.80 (3H, m), 7.60 (1H, m), 7.55–7.40 (4H, m), 7.30–7.10 (9H, m), 6.25 (1H, m), 6.15–6.05 (2H, m), 5.90 (1H, m), 4.90 (1H, m), 4.35 (1H, m), 4.25–4.15 (2H, m), 3.65 (1H, m), 3.50 (1H, m), 1.25 (3H, t).

Preparation 50
Benzyl 2-[({[2-(diisopropylamino)ethyl]amino}carbonyl)amino]-ethylcarbamate

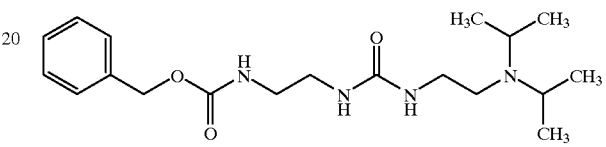

A solution of benzyl 2-aminoethylcarbamate hydrochloride (4.33 g, 18.8 mmol), N-[2-(diisopropylamino)ethyl]-1H-imidazole-1-carboxamide (Preparation 19) (3.73 g, 15.64 mmol) and triethylamine (2.62 ml, 18.8 mmol) in dichloromethane (100 ml) was heated under reflux for 14 hours. The solution was allowed to cool to room temperature and then washed with water (20 ml). The aqueous layer was separated and extracted with more dichloromethane (20 ml). The combined organic layers were dried over anhydrous magnesium sulfate and solvent evaporated under reduced pressure to give the title compound as a yellow oil (6.25 g).
$^1$H-NMR (400 MHz, CDCl$_3$) δ: 7.40–7.30 (5H, m), 5.50 (1H, br s), 5.10 (1H, s), 4.90 (1H, br s), 3.30 (4H, m), 3.10 (2H, m), 3.00 (2H, m), 2.55 (2H, m), 1.00 (12H, d).
LRMS: m/z [MH$^+$] 365.

Preparation 51
Benzyl 2-[({[2-(piperidinyl)ethyl]amino}carbonyl)amino]-ethylcarbamate

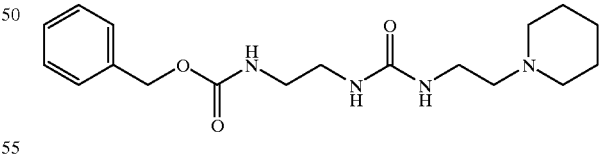

Prepared from benzyl 2-aminoethylcarbamate hydrochloride and N-[2-1-piperidinyl)ethyl]-1H-imidazole-1-carboxamide (Preparation 18) by a similar procedure to Preparation 50. The title compound was obtained as a yellow oil.
$^1$H-NMR (400 MHz, CDCl$_3$) δ: 7.30–7.20 (5H, m), 6.00 (1H, br s), 5.50 (1H, m), 5.10–5.00 (3H, br s), 3.30–3.10 (6H, m), 2.40 (6H, m), 1.55 (4H, m), 1.40 (2H, m).
LRMS: m/z [MH$^+$] 349.

Preparation 52
N-(2-Aminoethyl)-N'-[2-diisopropylamino)ethyl]urea

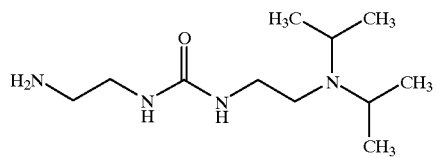

A solution of benzyl 2-[({[2-diisopropylamino)ethyl]amino}carbonyl)amino]ethylcarbamate (Preparation 50) (6.25 g, 14.45 mmol) in ethanol (100 ml) was hydrogenated at room temperature over palladium (II) hydroxide (250 mg) for 4 hours at 414. KPa The catalyst was removed by filtration through Arbocel (trade mark) and solvent evaporated under reduced pressure. The residue was purified by column chromatography on silica gel eluting with a gradient system of dichloromethane:methanol:concentrated aqueous ammonia (90:10:1, by volume) changing to dichloromethane:methanol:concentrated aqueous ammonia (90:10:2, by volume) to afford the title compound as a yellow oil (3.6 g).

$^1$H-NMR (400 MHz, CDCl$_3$) δ: 5.30 (1H, br s), 5.15 (1H, m), 3.20 (4H, m), 3.05 (2H, m), 2.80 (2H, m), 2.60 (2H, m), 1.05 (12H, d).

LRMS: m/z [MH$^+$] 231.

Preparation 53
N-(2-Aminoethyl)-N'-[2-(1-piperidinyl)ethyl]urea

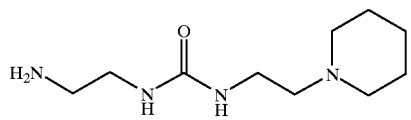

Prepared from benzyl 2-[({[2-1-piperidinyl)ethyl]amino}carbonyl)amino]ethylcarbamate (Preparation 51) by a similar method to Preparation 52. The title compound was obtained as a yellow oil.

$^1$H-NMR (400 MHz, CDCl$_3$) δ: 5.65 (1H, br s), 5.15 (1H, m), 3.20 (4H, m), 2.80 (2H, m), 2.40 (6H, m), 1.55 (4H, m), 1.40 (2H, m).

LRMS: m/z [MH$^+$] 215.

Preparation 54
Benzyl 4-{[(1H-imidazol-1-ylcarbonyl)amino]methyl}benzoate

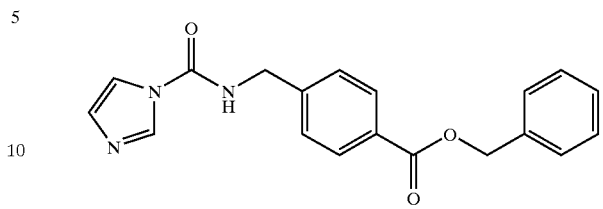

Benzyl 4-aminomethyl)benzoate hydrochloride (1.0 g, 36 mmol) was dissolved in 10% w/w aqueous sodium hydroxide solution (20 ml) and the solution extracted with dichloromethane (30 ml). The organic phase was separated, dried over anhydrous magnesium sulfate and solvent evaporated under reduced pressure to give the free base of the amine as a thick oil. This was dissolved in dichloromethane (20 ml) and the solution added dropwise to a solution of N,N'-carbonyldiimidazole (1.62 g, 10 mmol) in dichloromethane (20 ml). After stirring for one hour at room temperature the reaction mixture was diluted with diethyl ether (100 ml) and washed with water (3×40 ml) and brine (40 ml). The solution was dried over anhydrous magnesium sulfate and solvent evaporated under reduced pressure to give the target compound as a white solid (0.97 g, 81%).

$^1$H-NMR (400 MHz, CDCl$_3$) δ: 8.20 (1H, s), 8.00 (2H, d), 7.50–7.30 (9H, m), 6.95 (1H, s), 5.40 (2H, s), 4.60 (2H, m).

LRMS: m/z [MH$^+$] 336.

Preparation 55
Benzyl 4-[({[(2-{[(6-[(2,2-diphenylethyl)amino]-9-{(2R,3R,4S,5S)-5-[(ethylamino)carbonyl]-3,4-dihydroxytetrahydro-2-furanyl}-9H-purin-2-yl)carbonyl]amino}ethyl)amino]carbonyl}-amino)-methyl]benzoate

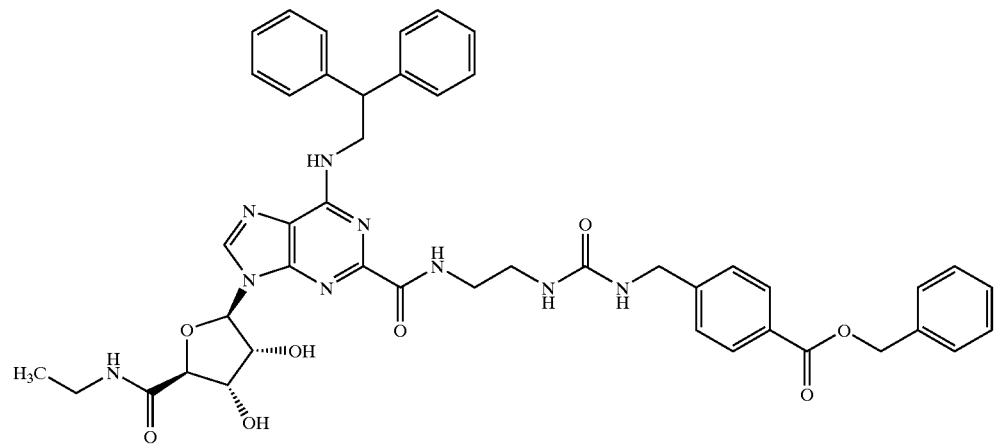

Prepared from N-(2-aminoethyl)-6-[(2,2-diphenylethyl)amino]-9-{(2R,3R,4S,5S)-5-[(ethylamino)carbonyl]-3,4-dihydroxytetrahydro-2-furanyl}-9H-purin-2-carboxamide (Preparation 10) and benzyl 4-{[(1H-imidazol-1 ylcarbonyl)amino]methyl}benzoate (Preparation 54) by a similar method to Example 1. The target compound was obtained as a white solid.

¹H-NMR (400 MHz, CD₃OD) δ: 8.35 (1H, s), 7.70 (2H, d), 7.40–7.10 (17H, m), 6.05 (1H, m), 5.20 (2H, m), 4.70 (1H, m), 4.45–4.20 (6H, m), 3.55–3.40 (4H, m), 3.20–3.30 (2H, m), 1.00 (3H, t).

LRMS: m/z [M-H⁺] 841.

Preparation 56

N-[2-(Dibutylamino)ethyl]-1H-imidazole-1-carboxamide

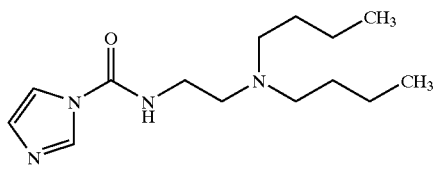

Prepared from N¹,N¹-dibutyl-1,2-ethanediamine and N,N'-carbonyldiimidazole by a similar method to Preparation 19. The target compound was obtained as a white solid.

¹H-NMR (400 MHz, CDCl₃) δ: 8.05 (1H, s), 7.25 (1H, s), 7.40 (1H, s), 6.75 (1H, br s), 3.40 (2H, m), 2.60 (2H, m), 2.50–2.30 (4H m), 1.40–1.20 (8H, m), 0.85 (6H, t),

LRMS: m/z [M-H⁺] 267.

Preparation 57

N-{2-[Benzyl-(isopropyl)amino]ethyl}-1H-imidazole-1-carboxamide

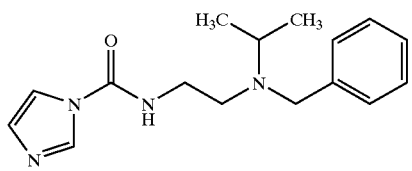

Prepared from N¹-benzyl-N¹-isopropyl-1,2-ethanediamine and N,N'-carbonyldiimidazole by a similar method to Preparation 19. The target compound was obtained as a white solid.

¹H-NMR (400 MHz, CDCl₃) δ: 7.85 (1H, s), 7.30–7.15 (5H, m), 7.10 (1H, s), 7.05 (1H, s), 6.00 (1H, brs), 3.50 (2H, s), 3.25 (2H, m), 3 00 (1H, m), 2.65 (2H, m), 1.10 (6H, d), Preparation 58

N-(1-Benzyl-4-piperidinyl)-1H-imidazole-1-carboxamide

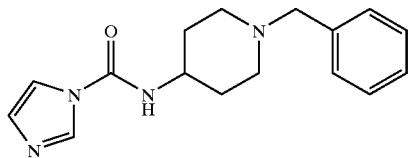

Prepared from 1-benzyl-4-piperidinylamine and N,N'-carbonyldiimidazole by a similar method to Preparation 19. The target compound was obtained as a white solid.

¹H-NMR (400 MHz, CDCl₃) δ: 8.10 (1H, s), 7.40–7.20 (6H, m), 7.10 (1H, s), 5.85 (1H, m), 3.85 (1H, m), 3.50 (2H, m), 2.90–2.80 (2H, m), 2.25–2.00 (4H, m), 1.60 (2H, m).

Preparation 59

N-[(1-Benzyl-4-piperidinyl)methyl]-1H-imidazole-1-carboxamide

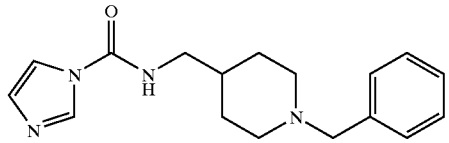

Prepared from (1-benzyl-4-piperidinyl)methylamine and N,N'-carbonyldiimidazole by a similar method to Preparation 19. The target compound was obtained as a white solid.

¹H-NMR (400 MHz, CDCl₃) δ: 8.10 (1H, s), 7.30–7.20 (6H, m) 7.10 (1H, s), 5.90 (1H, m), 3.50 (2H, s), 3.35 (2H, m), 2.90 (2H, m), 2.00 (2H, m), 1.75–1.60 (3H, m), 1.40–1.30 (2H, m).

Preparation 60

N-{4-[(Diethylamino)methyl]benzyl}-1H-imidazole-1-carboxamide

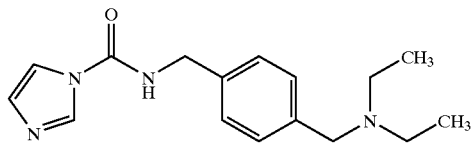

Prepared from N-[4-aminomethyl)benzyl]-N,N-diethylamine and N,N'-carbonyldiimidazole by a similar method to Preparation 19. The target compound was obtained as a white solid.

¹H-NMR (400 MHz, CDCl₃) δ: 8.15 (1H, s), 7.35–7.05 (6H, m), 4.60 (2H, s), 3.50 (2H, s), 2.50 (4H, q), 1.05 (6H, t).

LRMS: m/z [MH⁺] 287.

Preparation 61

N-[2-(3,4-Dihydro-2(1H)-isoquinolinyl)ethyl]-1H-imidazole-1-carboxamide

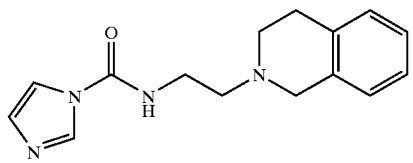

Prepared from 2-3,4-dihydro-2(1H)-isoquinolinyl) ethylamine and N,N'-carbonyldiimidazole by a similar method to Preparation 19. The target compound was obtained as a white solid.

$^1$H-NMR (400 MHz, CDCl$_3$) δ: 8.05 (1H, s), 7.25 (1H, s), 7.15–6.95 (5H, m), 6.65 (1H, br s), 3.70 (2H, s), 3.60 (2H, m), 2.90 (2H, m), 2.75 (4H, m).

Preparation 62

Ethyl 6-[(2,2-diphenylethyl)amino]-9-(tetrahydro-2H-pyran-2-yl)-9H-purine-2-carboxylate

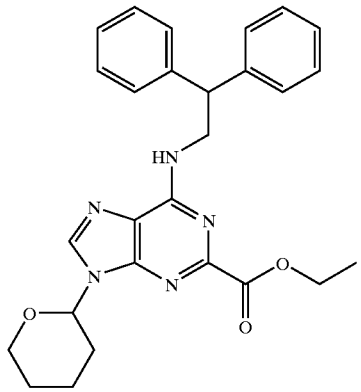

To a suspension of palladium (II) acetate (1.50 g, 0.00668 moles) in absolute ethanol (1000 ml) was added 1,1'-bis(diphenylphosphino)ferrocene (7.00 g, 0.0126 moles) and the resultant suspension was stirred under an atmosphere of nitrogen for 18 hours to give the catalyst mixture. To a mixture of 2-chloro-N-(2,2-diphenylethyl)-9-tetrahydro-2H-pyran-2-yl)-9H-purin-6-amine (WO/0023457) (Preparation 2) (700 g, 1.61 moles) and absolute ethanol (4500 ml) in an autoclave was added anhydrous sodium carbonate (94 g, 0.887 moles) and the catalyst mixture prepared above. The autoclave was flushed twice with carbon monoxide gas, then pressurised to 200 kPa using carbon monoxide gas. The mixture was then heated at 103–107° C. with stirring for 10 hours, and the autoclave was then vented, flushed with carbon monoxide, and then re-pressurised to 200 kPa with carbon monoxide. Heating at 103–107° C. with stirring was continued for a further 14 hours. The mixture was cooled to 60° C. and then filtered through a bed of warm Celite (trade mark). The resultant filtrate was allowed to cool to ambient temperature whereupon crystallisation occurred and, after stirring at this temperature for 7 hours, the resultant suspension was filtered. The filter cake was washed with cold absolute ethanol (500 ml) and the solid was dried in vacuo for 24 hours at 55° C. to give the title compound as a cream coloured solid (575 g), m.p. 138–140° C.

LRMS (positive atmospheric pressure chemical ionisation): m/z [MH$^+$]: 472.

$^1$H-NMR (300 MHz, CDCl$_3$) δ: 8.05 (1H, s), 7.45–7.15 (10H, m), 5.95–5.80 (2H, m), 4.60–4.30 (5H, m), 4.15 (1H, br d), 3.80 (1H, br t), 2.20–1.60 (6H, m), 1.50 (3H, t).

Preparation 63
Ethyl 6-[(2,2-diphenylethyl)amino]-9H-pyran-2-yl)-9H-purine-2-carboxylate

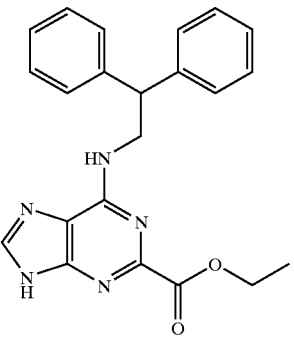

To a suspension of ethyl 6-[(2,2-diphenylethyl)amino]-9-tetrahydro-2H-pyran-2-yl)-9H-purine-2carboxylate (Preparation 62) (250 g, 0.530 moles) in absolute ethanol (1250 ml) under an atmosphere of nitrogen was added trifluoroacetic acid (73.5 g, 0.645 moles) and the resultant mixture was heated at 50° C. for 20 hours. The mixture was cooled and the solid was collected by filtration. The filter cake was washed with absolute ethanol (350 ml) and was then dried In vacuo at 50° C. to give the title compound (206.5 g) as a cream coloured fine powder, m.p.>200° C.

LRMS (positive atmospheric pressure chemical ionisation): m/z [MH$^+$] 388.

$^1$H-NMR (300 MHz, d$_6$-DMSO) δ: 8.36 (1H, br s), 8.00 (1H, br t), 7.48–7.12 7 (10H, m), 4.80–4.00 (5H, br m), 1.48–1.22 (3H, br m).

Preparation 64
Ethyl 9-{(2R,3R,4R,5R)-3,4-bis(acetyloxy)-5-[(acetyloxy)methyl]tetrahydro-2-furanyl}-6-[(2,2-diphenylethyl)amino]-9H-purine-9H-purine-2-carboxylate

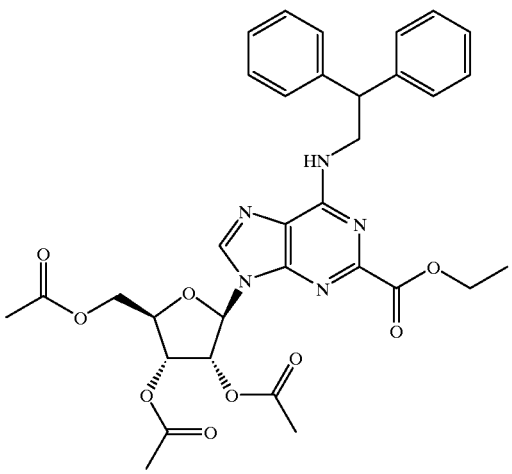

To a suspension of ethyl 6-[(2,2-diphenylethyl)amino]-9H-purine-2-carboxylate (Preparation 63) (40.0 g, 0.103 moles) in anhydrous 1,2-dimethoxyethane (240 ml) under an atmosphere of nitrogen was added 4-methylmorpholine (11.5 g, 12.5 ml, 0.114 moles) and the resultant mixture was heated to 45° C. with stirring. To this mixture was then added trimethylsilyl trifluoromethanesulphonate (27.5 g, 22.4 ml, 0.124 moles) over a period of 10 minutes. The resultant orange solution was then heated to 55° C., and a solution of 1,2,3,5-tetra-O-acetyl-β-D-ribofuranose (36.1 g, 0.113 moles) in 1,2-dimethoxyethane (100 ml plus 20 ml to rinse through) was added over a period of 10 minutes. The reaction was then stirred at 57–60° C. for 2 hours after which time the mixture was cooled to ambient temperature. The reaction mixture was then cautiously added to a mixture of saturated aqueous sodium bicarbonate solution (400 ml) and ethyl acetate (400 ml) with vigorous stirring. The layers were separated and the aqueous phase was extracted with ethyl acetate (400 ml). The combined organic phases were dried over anhydrous magnesium sulphate and were then concentrated in vacuo to give the crude product as an orange foam (74.9 g) that could be used as such for the next step. This crude product can be purified using flash chromatography on silica gel eluting with a gradient system of 10% v/v diethyl ether in dichloromethane changing to 25% v/v diethyl ether in dichloromethane to give the title compound as a colourless foam.

LRMS (positive atmospheric pressure chemical ionisation): m/z [MH$^+$] 646.

$^1$H-NMR (300 MHz, CDCl$_3$) δ: 7.98 (1H, br s), 7.40–7.17 (10H, m), 6.27 (1H, d), 6.00–5.78 (3H, m), 4.60–4.30 (8H, m), 2.16 (3H, s), 2.08 (6H, s), 1.45 (3H, t).

Preparation 65
Ethyl 9-[(2R,3R,4S,5R)-3,4-dihydroxy-5-(hydroxymethyl) tetrahydro-2-furanyl]-6-[(2,2-diphenylethyl)amino]-9H-purine-2-carboxylate

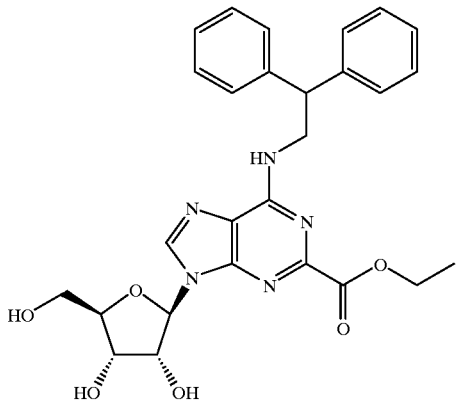

To a solution of crude ethyl 9-{(2R,3R,4R,5R)-3,4-bis (acetyloxy)-5-[(acetyloxy)methyl]tetrahydro-2-furanyl}-6-[(2,2-diphenylethyl)amino]-9H-purine-2-carboxylate (Preparation 64) (74.9 g, assumed 0.103 moles) in warm absolute ethanol (330 ml) was added sodium ethoxide (1.2 g, 0.018 moles) in portions over 23 hours. The resultant mixture was stirred for a further 3 hours and then glacial acetic acid (1.5 ml) was added. The mixture was concentrated in vacuo to give the crude product as a light brown foam (63.7 g) that was used as such for the next step. The crude product can be purified by flash chromatography on silica gel eluting with a gradient system of 5% v/v isopropanol in dichloromethane changing to 7.5% v/v isopropanol in dichloromethane changing to 10% v/v isopropanol in dichloromethane followed by crystallisation from tertiary-butyl methyl ether to give the title compound as colourless crystals, m.p. 118–120° C.

LRMS (positive atmospheric pressure chemical ionisation): m/z [MH$^+$] 520.

$^1$H-NMR (300 MHz, d$_6$-DMSO) δ: 8.61 (0.25H, br s), 8.47 (0.75H, br s), 8.17 (1H, br t), 7.45–7.10 (10H, m), 5.92 (1H, br d), 5.41 (1H, br d), 5.10 (1H, br d), 5.00 (1H, t), 4.80–4.45 (3H, m), 4.44–4.10 (2H, m), 4.09–4.03 (2H, m), 4.00–3.90 (1H, m), 3.78–3.61 (1H, m), 3.60–3.50 (1H, m), 1.48–1.11 (3H, m).

Preparation 66
Ethyl 9-[(3aR,4R,6R,6aR)-6-(hydroxymethyl)-2,2-dimethyltetrahydrofuro[3,4-d][1,3]dioxol-4-yl]-6-[(2,2-diphenylethyl)amino]-9H-purine-2-carboxylate

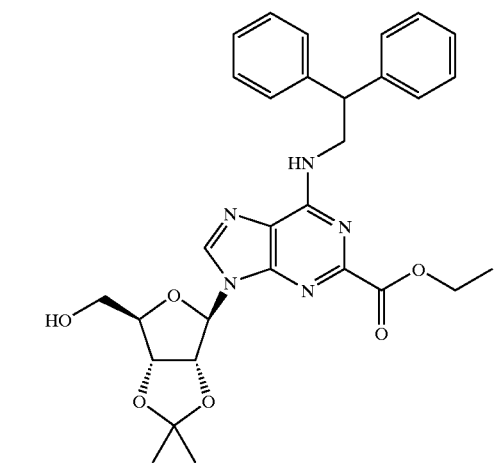

To a solution of crude ethyl 9-[(2R,3R,4S,5R)-3,4-dihydroxy-5-hydroxymethyl)tetrahydro-2-furanyl]-6-[(2,2-diphenylethyl)amino]-9H-purine2-carboxylate (Preparation 65) (62.7 g, assumed 0.103 moles) in dry acetone (314 ml) under an atmosphere of nitrogen was added concentrated sulphuric acid (5.3 ml, 0.103 moles) and the resultant mixture was stirred at ambient temperature for 2.5 hours. 2,2-Dimethoxypropane (21.5 g, 25.4 ml, 0.207 moles) was then added and stirring was continued for a further 2.5 hours. The reaction mixture was then added to saturated aqueous sodium bicarbonate solution (300 ml) and the resultant mixture was stirred at ambient temperature for 0.2 hours. The mixture was concentrated in vacuo and the aqueous residue was extracted with ethyl acetate (400 ml then 200 ml). The organic phases were combined and washed with saturated brine (300 ml), dried over anhydrous magnesium sulphate and concentrated in vacuo to give a yellow foam (58.2 g). A solution of this material in tertiary-butyl methyl ether (250 ml) was stirred at ambient temperature, under an atmosphere of nitrogen, to give a suspension that was then cooled in ice for 1 hour and the solid was then collected by filtration. The filter cake was washed with cold tertiary-butyl methyl ether (50 ml) and the product was dried in vacuo to give the title compound as a colourless solid (12.7 g). The mother liquors were purified by flash chromatography on silica gel (400 g) eluting with 75% v/v ethyl acetate in heptane to give slightly impure product (32.9 g) as a foam that was crystallised from tertiary-butyl methyl ether (150 ml) to give more title compound (8.3 g). The mother liquors were again concentrated In vacuo to give a foam (23.2 g) that was purified by flash chromatography eluting using a gradient system of 50% v/v ethyl acetate in toluene changing to 90% v/v ethyl acetate in toluene to give 2 fractions (9.7 g and 11.8 g) that were separately crystallised from tertiary-butyl methyl ether (100 ml and 120 ml respectively) to give more title compound (6.6 g and 8.8 g respectively). The total yield of the title compound was therefore 36.4 g, and it was isolated as a colourless crystalline solid, m.p. 126–128° C.

LRMS (positive atmospheric pressure chemical ionisation): m/z [MH$^+$] 560.

¹H-NMR (300 MHz, d₆-DMSO) δ: 8.60 (0.25H, br s), 8.45 (0.75H, s), 8.19 (1H, br t), 7.42–7.11 (10H, m), 6.19 (1H, br s), 5.40–5.25 (1H, m), 5.12–4.90 (2H, m), 4.78–4.82 (1H, m), 4.80–4.45 (1H, br s), 4.44–4.02 (4H, m), 3.65–3.50 (2H, m), 1.57 (3H, s), 1.50–1.10 (6H, m).

Preparation 67

(3aS,4S,6R,6aR)-6-[6-[(2,2-Diphenylethyl)amino]-2-(ethoxycarbonyl)-9H-purin-9-yl]-2,2-dimethyltetrahydrofuro[3,4-d][1,3]dioxole-4-carboxylic acid

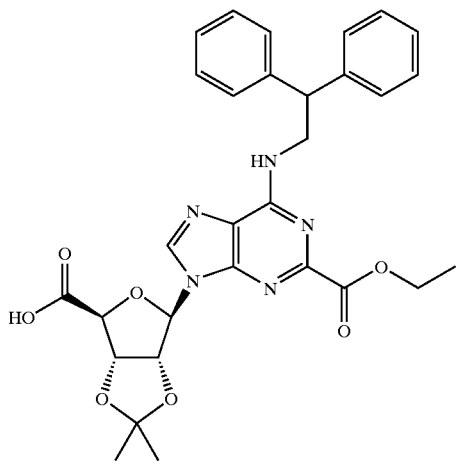

To a solution of ethyl 9-[(3aR,4R,6R,6aR)-6-hydroxymethyl)-2,2-dimethyltetrahydrofuro[3,4-d][1,3]dioxol-4-yl]-6-[(2,2-diphenylethyl)amino]-9H-purine-2-carboxylate (Preparation 66) (15.4 g, 0.0276 moles) in acetonitrile under an atmosphere of nitrogen was added 2,2,6,6-tetramethylpiperidinyl-1-oxy, free radical (0.30 g, 0.0019 moles) and aqueous sodium dihydrogen phosphate (120 ml of a 0.67M solution). The resultant mixture was heated to 45° C. with stirring. A solution of sodium chlorite (6.5 g, 0.072 moles) in water (75 ml) and a solution of sodium hypochlorite (0.32 ml of commercial solution with 12% w/v available chlorine, 0.000551 moles) in water (38 ml) were added separately and simultaneously to the stirred mixture over a period of 1 hour. The resultant mixture was then stirred at 45–50° C. for 10 hours, and for 18 hours at ambient temperature. The reaction mixture was then added to a solution of sodium sulphite (18 g, 0.143 moles) in water (300 ml) with stirring. After stirring for 5 minutes, the pH was adjusted to 3.7 by the addition of 2M aqueous hydrochloric acid and the mixture was extracted with ethyl acetate (200 ml then 100 ml). The organic phases were combined, dried over anhydrous magnesium sulphate and were then concentrated in vacuo to give the title compound (15.1 g) as a colourless foam that was used as such for the next step. If necessary, this crude product can be purified by standard means, for example by flash chromatography on silica gel.

LRMS (positive atmospheric pressure chemical ionisation): m/z [MH⁺] 574.

¹H-NMR (300 MHz, d₆-DMSO) δ: 12.80 (1H, br s), 8.52 (0.25H, br s), 8.38 (0.75H, s), 8.13 (1H, br t), 7.45–7.12 (10H, m), 6.40 (1H, s), 5.81 (1H, d), 5.48 (1H, d), 4.80–4.00 (6H, m), 1.52 (3H, s), 1.45–1.13 (6H, m).

Preparation 68

(3aS,4S,6R,6aR)-6-[6-[(2,2-Diphenylethyl)amino]-2-(ethoxycarbonyl)-9H-purin-9-yl]-2,2-dimethyltetrahydrofuro[3,4-d][1,3]dioxole-4-carboxylic acid

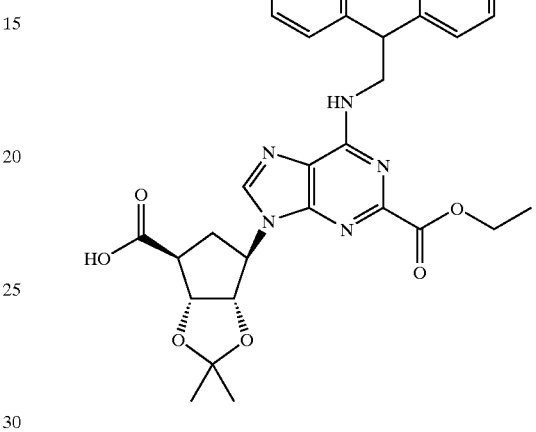

To a solution of 9-[(3aR,4R,6R,6aR)-6-hydroxymethyl)-2,2-dimethyltetrahydrofuro[3,4-d][1,3]dioxol-4-yl]-6-[(2,2-diphenylethyl)amino]-9H-purine-2-carboxylate (Preparation 66) (5.0 g, 0.0089 moles) in dichloromethane (75 ml) was added 2,2,6,6-tetramethylpiperidinyl-1-oxy, free radical (0.020 g, 0.000128 moles), tetrabutylammonium bromide (0.22 g, 0.000682 moles) and saturated aqueous sodium bicarbonate solution (25 ml). To this rapidly stirred mixture was then added an aqueous solution of sodium hypochlorite (33 ml of a 0.531M solution, 0.0175 moles) over a period of 15 minutes at ambient temperature and stirring was continued for an additional 1.5 hours. To the resultant mixture was added an aqueous solution of sodium sulphite (50 ml of 10% w/v solution) and stirring was continued for 10 minutes. The slightly cloudy organic phase was then separated, and was then concentrated to dryness in vacuo to give a yellow foam This material was partitioned between ethyl acetate (50 ml) and aqueous hydrochloric acid (25 ml of a 2M solution). The organic phase was then washed with water, and was then concentrated in vacuo. The residue was redissolved in ethyl acetate (50 ml) and was concentrated again in vacuo to give the title compound (5.23 g) as a pale yellow foam that was used as such for the next step. If necessary, this crude product can be purified by standard means, for example by flash chromatography on silica gel.

LRMS (positive atmospheric pressure chemical ionisation): m/z [MH⁺] 574.

¹H-NMR (300 MHz, d₆-DMSO) δ: 12.80 (1H, br s), 8.52 (0.25H, br s), 8.38 (0.75H, s), 8.13 (1H, br t), 7.45–7.12 (10H, m), 6.40 (1H, s), 5.81 (1H, d), 5.48 (1H, d), 4.80–4.00 (6H, m), 1.52 (3H, s), 1.45–1.13 (6H, m).

Preparation 69

Ethyl 9-{(3aR,4R,6S,6aS)-6-[(ethylamino)carbonyl]-2,2-dimethyltetrahydrofuro[3,4-d][1,3]dioxol-4-yl}-6-[(2,2-diphenylethyl)amino]-9H-purine-2-carboxylate

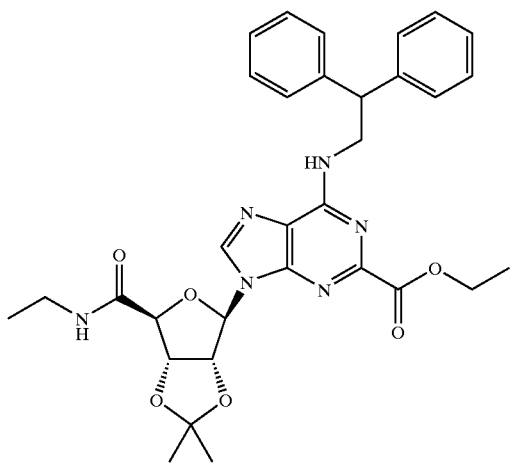

To a solution of (3aS,4S,6R,6aR)-6-[6-[(2,2-diphenylethyl)amino]-2-ethoxycarbonyl)-9H-purin-9-yl]-2,2-dimethyltetrahydrofuro[3,4-d][1,3]dioxole-4-carboxylic acid (Preparations 67 and 68) (20.0 g, 0.0349 moles) in anhydrous tetrahydrofuran (100 ml) under an atmosphere of nitrogen was added 1,1'-carbonyldiimidazole (6.80 g, 0.0418 moles) and the resultant mixture was stirred at ambient temperature for 1.5 hours. To this solution was then added a solution of ethylamine in tetrahydrofuran (24.4 ml of a 2M solution, 0.0488 moles) with cooling at 15° C., and the resultant mixture was then stirred at ambient temperature for 2 hours. To the mixture was added more of a solution of ethylamine in tetrahydrofuran (3.5 ml of a 2M solution, 0.0007 moles) and stirring was continued for an additional 2 hours after which time deionised water (10 ml) was added. The resultant mixture was concentrated in vacuo and the residue was then partitioned between ethyl acetate (200 ml) and aqueous citric acid (200 ml of a 0.5M solution). The layers were separated and the aqueous phase was extracted with ethyl acetate (50 ml). The organic phases were combined and were washed successively with deionised water (200 ml), saturated aqueous sodium bicarbonate solution (200 ml) and saturated brine (200 ml), and were subsequently dried over anhydrous magnesium sulphate and concentrated in vacuo to give the crude product as a cream coloured foam (20.22 g). The crude product was purified by flash chromatography on silica gel (700 g) eluting with a gradient system of 65% v/v ethyl acetate in heptane changing to 80% v/v ethyl acetate in heptane changing to ethyl acetate, to give the title compound (16.55 g) as a colourless foam LRMS (positive atmospheric pressure chemical ionisation): m/z [MH$^+$] 601.

$^1$H-NMR (300 MHz, d$_6$-DMSO) δ: 8.53 (0.25H, br s), 8.38 (0.75H, s), 8.15 (1H, br t), 7.42–7.12 (11H, m), 6.40 (1H, br s), 5.59 (1H, br d), 5.40 (1H, br d), 4.80–4.00 (6H, m), 2.83–2.60 (2H, m) 1.55 (3H, s), 1.45–1.25 (6H, m), 0.52 (3H, br t).

Preparation 70

9-{(3aR,4R,6S,6aS)-6-[(Ethylamino)carbonyl]-2,2-dimethyltetrahydrofuro[3,4-d][1,3]dioxol-4-yl}-6-[(2,2-diphenylethyl)amino]-9H-purine-2-carboxylic acid

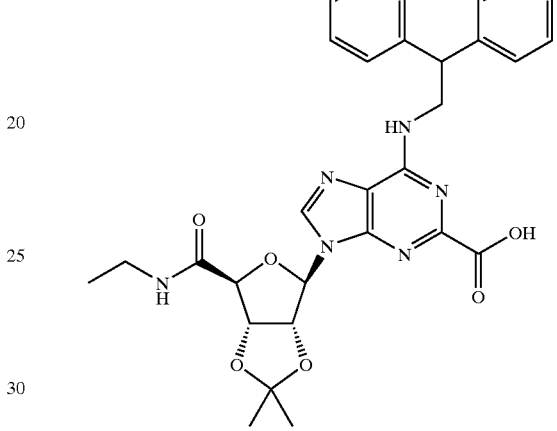

To a solution of ethyl 9-{(3aR,4R,6S,6aS)-6-[(ethylamino)carbonyl]-2,2-dimethyltetrahydrofuro[3,4-d][1,3]dioxol-4-yl}-6-[(2,2-diphenylethyl)amino]-9H-purine-2-carboxylate (Preparation 69) (16.47 g, 0.0274 moles) in methanol (164 ml) was added aqueous sodium hydroxide (30.2 ml of a 1M solution, 0.0302 moles) and the resultant mixture was stirred at ambient temperature under an atmosphere of nitrogen for 1.5 hours. The reaction mixture was then concentrated in vacuo and to the residue was added dichloromethane (160 ml) and deionised water (160 ml). The pH of this mixture was adjusted to pH 4 by the addition of aqueous 2M hydrochloric acid with stirring. The organic phase was separated and the aqueous layer was extracted with dichloromethane (75 ml). The organic phases were then combined, dried over anhydrous magnesium sulphate and concentrated in vacuo to give the title compound (15.5 g) as a cream coloured foam that was used as such for the next step. If necessary, this crude product can be purified by standard means, such as flash chromatography on silica gel.

LRMS (positive atmospheric pressure chemical ionisation): m/z [MH$^+$] 573.

$^1$H-NMR (300 MHz, d$_6$-DMSO) δ: 12.71 (1H, br s) 8.52 (0.25H, br s), 8.36 (0.75H, s), 8.08 (1H, br t), 7.50 (1H, br t), 7.40–7.12 (10H, m), 6.40 (1H, br s), 5.55 (1H, br d), 5.38 (1H, br d), 4.75–4.40 (2 5H, m), 4.25–4.03 (1.5H, m) 2.88–2.63 (2H, m) 1.55 (3H, s), 1.34 (3H, m), 0.52 (3H, br t).

Preparation 71
9-{(3aR,4R,6S,6aS)-6-[(Ethylamino)carbonyl]-2,2-dimethyltetrahydrofuro[3,4-d][1,3]dioxol-4-yl}-6-[(2,2-diphenylethyl)amino]-N-{2-[({[1-(2-pyridinyl)-4-piperidinyl]amino}carbonyl)amino]ethyl}-9H-purine-2-carboxamide

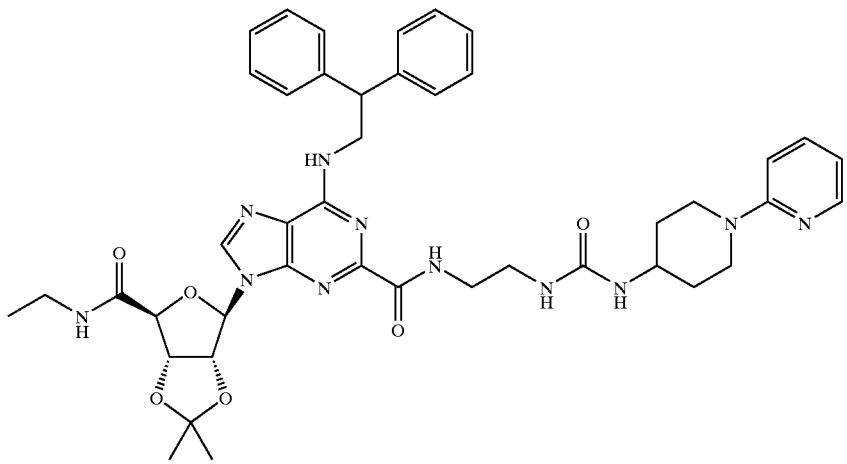

To a solution of 9-{(3aR,4R,6S,6aS)-6-[(ethylamino)carbonyl]-2,2-dimethyltetrahydrofuro[3,4-d][1,3]dioxol-4-yl}-6-[(2,2-diphenylethyl)amino]-9H-purine-2-carboxylic acid (Preparation 70) (14.98 g, 0.0262 moles) in dichloromethane (75 ml) under an atmosphere of nitrogen was added 1,1'-carbonyldiimidazole (4.7 g, 0.029 moles) and the resultant mixture was stirred at ambient temperature for 1.5 hours to give a solution of the derived acyl imidazolide. To a solution of N-(2-aminoethyl)-N'-[1-(2-pyridinyl)-4-piperidinyl]urea dihydrochloride (Preparation 73) (10.1 g, 0.0301 moles) in dichloromethane (75 ml) under an atmosphere of nitrogen was added triethylamine (5.6 g, 7.7 ml, 0.055 moles), and the resultant suspension was cooled to 15° C. To this suspension was then added the solution of the acyl imidazolide prepared above and the resultant mixture was stirred at ambient temperature for 2 hours after which time deionised water (5 ml) was added. The mixture was washed with aqueous citric acid (150 ml of a 0.5M solution) that had been saturated with sodium chloride. The layers were separated, and the aqueous phase was extracted with dichloromethane (75 ml). The organic phases were combined and were washed with saturated aqueous sodium bicarbonate solution. After separating the phases, the aqueous layer was extracted with dichloromethane (75 ml) and the organic phases were then combined, dried over anhydrous magnesium sulphate and then were concentrated in vacuo to give the title compound (21.28 g) as a light blue foam that was used as such for the next step. This crude product can be purified by standard means such as by flash chromatography on silica gel eluting with a system comprising 95:5:0.5, by volume, dichloromethane:methanol:concentrated aqueous ammonia to give the pure title compound.

LRMS (positive atmospheric pressure chemical ionisation): m/z [MH$^+$] 818.

$^1$H-NMR (300 MHz, d$_6$-DMSO) δ: 8.51 (1H, br s), 8.33 (1H, br s), 8.09 (1H, m), 8.01 (1H, br t), 7.58 (1H, br t), 7.48 (1H, t), 7.42–7.10 (10H, m), 6.78 (1H, d), 6.58 (1H, dd), 6.42 (1H, s), 6.01 (1H, br s), 5.95 (1H, br d), 5.60 (1H, br d), 5.39 (1H, br d), 4.72–4.55 (2.5H, m), 4.33–4.00 (3.5H, m), 3.75–3.55 (1H, m), 3.44–3.20 (4H, m (partly obscured by water peak)), 2.88 (2H, br t), 2.80–2.62 (2H, m), 1.87–1.70 (2H, m), 1.53 (3H, s), 1.37 (3H, s), 1.36–1.20 (2H, m), 0.47 (3H, t).

Preparation 72
tert-Butyl 2-[({[1-(2-pyridinyl)-4-piperidinyl]amino}carbonyl)amino]ethylcarbamate

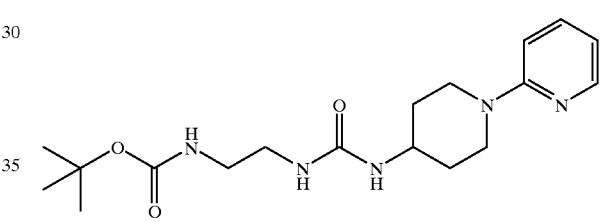

To an ice-cooled solution of 1-(2-pyridinyl)-4-piperidinylamine dihydrochloride (EP-A-0021973) (20.82 g, 0.0832 moles) and 1,1'-carbonyldiimidazole (14.85 g, 0.915 moles) in acetonitrile (140 ml) under an atmosphere of nitrogen was added N,N-di-iso-propylethylamine (22.0 g, 29.7 ml, 0.170 moles) over a period of 20 minutes. The resultant light brown solution was stirred at ambient temperature for 20 minutes and a solution of tert-butyl N-(2-aminoethyl)carbamate (14.0 g, 0.0874 moles) in acetonitrile (10 ml plus 5 ml rinse) was added over a period of 5 minutes The resultant mixture was then heated under reflux for 2.5 hours. After cooling to ambient temperature, the reaction mixture was concentrated in vacuo and the residue was dissolved in ethyl acetate (150 ml). This solution was washed successively with saturated aqueous sodium bicarbonate solution (70 ml) and deionised water (20 ml). The aqueous phases were extracted with ethyl acetate (2×100 ml) and the combined organic phases were washed with water. The organic phase was dried over anhydrous magnesium sulphate and the solution was concentrated to a volume of approximately 200 ml in vacuo. The resultant solution was then distilled at atmospheric pressure until the volume was approximately 75 ml. The solution was allowed to cool to ambient temperature during which time crystallisation occurred. The resultant thick slurry was diluted with ethyl acetate (60 ml) and was cooled in ice. The solid was collected by filtration and the filter cake was washed with cold ethyl acetate (2×30 ml). The resultant solid was dried in vacuo at 50° C. for 20 hours to give the crude product (24.0 g) that was recrystallised from ethyl acetate (270 ml) to give the title compound (20.7 g) as a colourless solid LRMS (positive atmospheric pressure chemical ionisation): m/z [MH$^+$] 364.

$^1$H-NMR (300 MHz, CDCl$_3$) δ: 8.20–8.10 (1H, m), 7.45 (1H, t), 6.65 (1H, d), 6.58 (1H, dd), 5.42 (1H, br t), 5.25 (1H, br s), 5.04 (1H, d), 4.15 (2H, d), 3.90–3.68 (1H, m), 3.47–3.10 (4H, m), 3.00 (2H, br t), 2.00 (2H, br d), 1.55–1.28 (11H, m).

Preparation 73
N-(2-Aminoethyl)-N'-[1-(2-pyridinyl)-4-piperidinyl]urea dihydrochloride

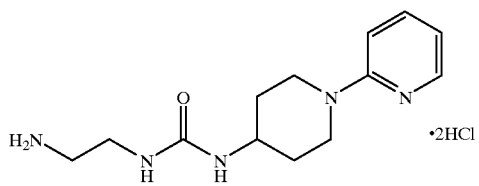

To a suspension of tert-butyl 2-[({[1-(2-pyridinyl)-4-piperidinyl]amino}carbonyl)amino]ethylcarbamate (Preparation 72) (20.6 g, 0.0567 moles) in ethyl acetate (115 ml) under an atmosphere of nitrogen was added a saturated solution of hydrogen chloride in ethyl acetate (115 ml) and the resulting thick slurry was stirred at ambient temperature for 2 hours. The solid was collected by filtration and the filter cake was washed with ethyl acetate (2×50 ml) after which it was dried in vacuo at 50° C. to give the title compound (21.0 g) as a hygroscopic colourless solid, m.p. 112–120° C.

LRMS (positive atmospheric pressure chemical ionisation): m/z [MH$^+$] 264.

$^1$H-NMR (300 MHz, D$_2$O) δ: 7.92 (1H, t), 7.78 (1H, d), 7.23 (1H, d), 6.86 (1H, t), 4.00 (2H, br d), 3.85–3.70 (1H, m), 3.47–3.24 (4H, m), 3.18–2.95 (2H, m), 2.10–1.92 (2H, m), 1.53 (2H, br q).

Preparation 74
N-(2-Aminoethyl)-N'-[1-(2-pyridinyl)-4-piperidinyl]urea

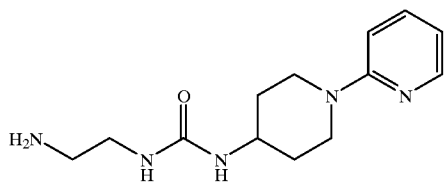

To a suspension of 1-(2-pyridinyl)-4-piperidinylamine dihydrochloride (EP-A-0021973) (1.0 g, 0.0040 moles) in ethyl acetate (10 ml) under an atmosphere of nitrogen was added 1,1'-carbonyldiimidazole (0.713 g, 0.0044 moles) and the resultant mixture was stirred at ambient temperature for 1 hour. After this time, triethylamine (0.40 g, 0.5 ml, 0.004 moles) was then added and stirring was continued for a further 2 hours after which time more N,N'-carbonyldiimidazole (0.145 g, 0.0009 moles) was added. The reaction mixture was stirred for a further 2 hours and it was then added to a solution of 1,2-diaminoethane (2.4 g, 2.7 ml, 0,04 moles) in ethyl acetate (3 ml) over 15 minutes together with the additional ethyl acetate (17 ml) used to rinse through the apparatus. The resultant mixture was stirred at ambient temperature for 18 hours and was washed with saturated aqueous sodium bicarbonate solution. The layers were then separated and the aqueous phase was extracted with ethyl acetate (2×20 ml). The organic layers were then combined, dried over anhydrous magnesium sulphate and were then concentrated in vacuo to give the crude product (0.83 g). Examination of this crude product by high performance liquid chromatography-mass spectroscopy and $^1$H NMR, by comparison with a genuine sample of the title compound (as the free base, prepared from N-(2-aminoethyl)-N'-[1-(2-pyridinyl)-4-piperidinyl]urea dihydrochloride (Preparation 73)), showed that the title compound was present as the major constituent together with minor impurities.

LRMS (positive atmospheric pressure chemical ionisation): m/z [MH$^+$] 264.

$^1$H-NMR (300 MHz, CDCl$_3$) δ: 8.15 (1H, d), 7.44 (1H, t), 6.64 (1H, d), 6.59 (1H, dd), 5.42–5.30 (2H, m), 4.15 (2H, br d), 3.90–3.70 (1H, m), 3.28–3.08 (2H, m), 2H, m), 2.79 (2H, t), 2.07–1.85 (2H, m), 1.52–1.28 (2H, m).

PHARMACOLOGICAL DATA

The compounds of Examples 1–35 were tested for biological activity by the method described on page 37, lines 5–17 and all were found to have an IC$_{50}$ of less than 100 nM.

What is claimed is:

1. A compound of the formula:

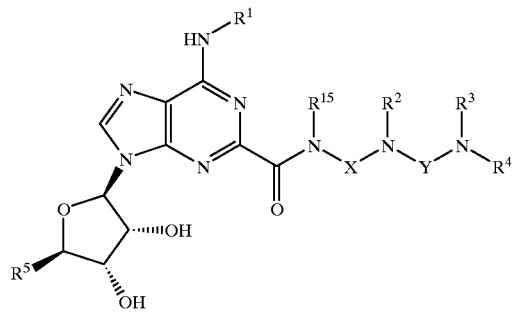

(I)

or a pharmaceutically acceptable salt or solvate thereof, wherein

R$^1$ is H, C$_1$–C$_6$ alkyl or fluorenyl, said C$_1$–C$_6$ alkyl being optionally substituted by 1 or 2 substituents each independently selected from phenyl and naphthyl, said phenyl and naphthyl being optionally substituted by C$_1$–C$_6$ alkyl, C$_1$–C$_6$ alkoxy, halo or cyano;

(A) R$^2$ is H or C$_1$–C$_6$ alkyl, R$^{15}$ is H or C$_1$–C$_6$ alkyl, and X is either (i) unbranched C$_2$–C$_3$ alkylene optionally substituted by C$_1$–C$_6$ alkyl or C$_3$–C$_8$ cycloalkyl, or (ii) a group of the formula:

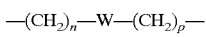

where W is C$_5$–C$_7$ cycloalkylene optionally substituted by C$_1$–C$_6$ alkyl, n is 0 or 1 and p is 0 or 1, or (B) R$^{15}$ is H— or C$_1$–C$_6$ alkyl, and R$^2$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by C$_1$–C$_6$ alkyl, or (C) R$^2$ is H or C$_1$–C$_6$ alkyl, and R$^{15}$ and X, taken together with the nitrogen atom to which they are attached, represent azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl;

either, $R^3$ and $R^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by $C_1$–$C_6$ alkyl or $C_3$–$C_8$ cycloalkyl and optionally substituted on a ring carbon atom not adjacent to a ring nitrogen atom by —$NR^6R^7$, or, $R^3$ is H, $C_1$–$C_6$ alkyl, $C_3$–$C_8$ cycloalkyl or benzyl and $R^4$ is (a) azetidin-3-yl, pyrrolidin-3-yl, piperidin-3-yl, piperidin-4-yl, homopiperidin-3-yl or homopiperidin-4-yl, each being optionally substituted by $C_1$–$C_6$ alkyl, $C_3$–$C_8$ cycloalkyl, phenyl, benzyl or het, or (b) —($C_2$–$C_6$ alkylene)-$R^8$, (c) —($C_1$–$C_6$ alkylene)-$R^{13}$, or (d) $C_1$–$C_6$ alkyl or $C_3$–$C_8$ cycloalkyl;

$R^5$ is $CH_2OH$ or $CONHR^{14}$;

$R^6$ and $R^7$ are either each independently H or $C_1$–$C_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$—($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) $NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, $C_2$–$C_5$ alkanoyl or —$SO_2NR^9R^9$;

$R^{13}$ is (a) phenyl, pyridin-2-yl, pyridin-3-yl or pyridin-4-yl, each being optionally substituted by $C_1$–$C_6$ alkyl, $C_1$–$C_6$ alkoxy, —($C_1$–$C_3$ alkylene)-($C_1$–$C_6$ alkoxy), halo, cyano, —($C_1$–$C_3$ alkylene)-CN, —$CO_2H$, —($C_1$–$C_3$ alkylene)-$CO_2H$, —$CO_2(C_1$–$C_6$ alkyl), —($C_1$–$C_3$ alkylene)-$CO_2(C_1$–$C_6$ alkyl), —($C_1$–$C_3$ alkylene)-$NR^{14}R^{14}$, —$CONR^{14}R^{14}$ or —($C_1$–$C_3$ alkylene)-$CONR^{14}R^{14}$, or (b) azetidin-2-yl, azetidin-3-yl, pyrrolidin-2-yl, pyrrolidin-3-yl, piperidin-2-yl, piperidin-3-yl, piperidin-4-yl, homopiperidin-2-yl, homopiperidin-3-yl or homopiperidin-4-yl, each being optionally substituted by $C_1$–$C_6$ alkyl, $C_3$–$C_8$ cycloalkyl, phenyl, benzyl or het;

$R^{14}$ is H or $C_1$–$C_6$ alkyl optionally substituted by cyclopropyl;

m is 0, 1 or 2;

Y is CO, CS, $SO_2$ or C=N(CN); and

"het", used in the definition of $R^4$ and $R^{13}$, is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo.

2. A compound as claimed in claim 1 wherein $R^1$ is $C_1$–$C_6$ alkyl optionally substituted by 1 or 2 phenyl substituents, said phenyl being optionally substituted by $C_1$–$C_6$ alkyl or halo.

3. A compound as claimed in claim 2 wherein $R^1$ is diphenylethyl, bis(3-methylphenyl)ethyl or bis(3-chlorophenyl)ethyl.

4. A compound as claimed in claim 3 wherein $R^1$ is 2,2-diphenylethyl, 2,2-bis(3-methylphenyl)ethyl or 2,2-bis(3-chlorophenyl)ethyl.

5. A compound as claimed in claim 4 wherein $R^1$ is 2,2-diphenylethyl.

6. A compound as claimed in claim 1 wherein $R^2$ is H.

7. A compound as claimed in claim 1 wherein $R^{15}$ is H.

8. A compound as claimed in claim 1 wherein X is 1,2-ethylene or 1,3-propylene.

9. A compound as claimed in claim 8 wherein X is 1,2-ethylene.

10. A compound as claimed in claim 1 wherein $R^2$ is H, $R^{15}$ is H and X is 1,2-ethylene, 1,3-propylene or a group of ther formula:

$$-(CH_2)_n-W-(CH_2)_p-$$

where W is $C_5$–$C_7$ cycloalkylene, n is 0 or 1 and p is 0 or 1.

11. A compound as claimed in claim 10 wherein $R^2$ is H, $R^{15}$ is H and X is 1,2-ethylene, 1,3-propylene or a group of the formula:

$$-(CH_2)_n-W-(CH_2)_p-$$

where W is $C_5$–$C_7$ cycloalkylene, n is 0 and p is 0.

12. A compound as claimed in claim 11 wherein $R^2$ is H, $R^{15}$ is H and X is 1,2-ethylene, 1,3-propylene or 1,4-cyclohexylene.

13. A compound as claimed in claim 12 wherein $R^2$ is H, $R^{15}$ is H and X is 1,2-ethylene.

14. A compound as claimed in claim 1 wherein $R^{15}$ is H and $R^2$ and X, taken together with the nitrogen atom to which they are attached, represent 3-pyrrolidinyl or 3- or 4-piperidinyl, each being optionally substituted by $C_1$–$C_6$ alkyl.

15. A compound as claimed in claim 14 wherein $R^{15}$ is H and $R^2$ and X, taken together with the nitrogen atom to which they are attached, represent 3-pyrrolidinyl or 4-piperidinyl.

16. A compound as claimed in claim 1 wherein $R^2$ is H and $R^{15}$ and X, taken together with the nitrogen atom to which they are attached, represent 3-pyrrolidinyl or 3- or 4-piperidinyl, each being optionally substituted by $C_1$–$C_6$ alkyl.

17. A compound as claimed in claim 16 wherein $R^2$ is H and $R^{15}$ and X, taken together with the nitrogen atom to which they are attached, represent 3-pyrrolidinyl or 4-piperidinyl.

18. A compound as claimed in claim 1 wherein $R^3$ is H.

19. A compound as claimed in claim 1 wherein $R^4$ is piperidin-3-yl or piperidin-4-yl, each optionally substituted by benzyl, pyridin-2-yl, pyridin-3-yl or pyridin-4-yl, said pyridin-2-yl, pyridin-3-yl and pyridin-4-yl each optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo.

20. A compound as claimed in claim 19 wherein $R^4$ is piperidin-3-yl or piperidin-4-yl, each substituted by benzyl, pyridin-2-yl, pyridin-3-yl or pyridin-4-yl.

21. A compound as claimed in claim 20 wherein $R^4$ is piperidin-4-yl substituted by pyridin-2-yl.

22. A compound as claimed in claim 21 wherein $R^4$ is 1-(pyridin-2-yl)piperidin-4-yl.

23. A compound as claimed in claim 1 wherein $R^4$ is —($C_2$–$C_6$ alkylene)-$R^8$.

24. A compound as claimed in claim 23 wherein $R^4$ is —$CH_2CH_2R^8$.

25. A compound as claimed in claim 1 wherein $R^4$ is —($C_1$–$C_6$ alkylene)-$R^{13}$.

26. A compound as claimed in claim 25 wherein $R^4$ is —$CH_2R^{13}$ or —$CH_2CH_2R^{13}$.

27. A compound as claimed in claim 1 wherein $R^4$ is $C_3$–$C_8$ cycloalkyl.

28. A compound as claimed in claim 27 wherein $R^4$ is cyclohexyl.

29. A compound as claimed in claim 1 wherein $R^5$ is —$CH_2OH$ or —$CONH(C_1$–$C_6$ alkyl).

30. A compound as claimed in claim 29 wherein $R^5$ is —$CONHCH_2CH_3$.

31. A compound as claimed in claim 23 wherein $R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl and said piperazin-1-yl and homopiperazin-1-yl being optionally substituted on the ring nitrogen atom not attached to the $C_2$–$C_6$ alkylene group by $C_1$–$C_6$ alkyl, or (ii) is $NR^{11}R^{12}$.

32. A compound as claimed in claim 31 wherein $R^8$ is piperidin-1-yl or tetrahydroisoquinolin-1-yl each optionally substituted on a ring carbon atom by $C_1$–$C_6$ alkyl.

33. A compound as claimed in claim 32 wherein $R^8$ is piperidin-1-yl, 4-isopropylpiperidin-1-yl or tetrahydroisoquinolin-1-yl.

34. A compound as claimed in claim 31 wherein $R^8$ is $NR^{11}R^{12}$ where $NR^{11}R^{12}$ is $N(C_1$–$C_6$ alkyl$)_2$, $N(C_1$–$C_6$ alkyl)($C_3$–$C_8$ cycloalkyl) or $N(C_1$–$C_6$ alkyl)(benzyl).

35. A compound as claimed in claim 34 wherein $NR^{11}R^{12}$ is N,N-diisopropylamino, N,N-di-n-butylamino, N-cyclopentyl-N-isopropylamino, N-cyclohexyl-N-isopropylamino or N-benzyl-N-isopropylamino.

36. A compound as claimed in claim 31 wherein $R^{11}$ is H or $C_1$–$C_6$ alkyl and $R^{12}$ is H, $C_1$–$C_6$ alkyl, $C_3$–$C_8$ cycloalkyl or benzyl.

37. A compound as claimed in claim 36 wherein $R^{11}$ is $C_1$–$C_6$ alkyl and $R^{12}$ is $C_1$–$C_6$ alkyl, $C_3$–$C_8$ cycloalkyl or benzyl.

38. A compound as claimed in claim 37 wherein $R^{11}$ is isopropyl or n-butyl and $R^{12}$ is isopropyl, n-butyl, cyclopentyl, cyclohexyl or benzyl.

39. A compound as claimed in claim 25 wherein $R^{13}$ is either phenyl optionally substituted by —($C_1$–$C_3$ alkylene)-$NR^{14}R^{14}$ or —$CO_2H$, or piperidin-2-yl, piperidin-3-yl or piperidin-4-yl each optionally substituted by benzyl.

40. A compound as claimed in claim 39 wherein $R^{13}$ is phenyl, 4-(N,N-diethylamino)methylphenyl, 4-carboxyphenyl or 1-benzylpiperidin-4-yl.

41. A compound as claimed in claim 1 wherein Y is CO.

42. A compound as claimed in claim 1 wherein:

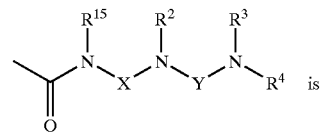
is

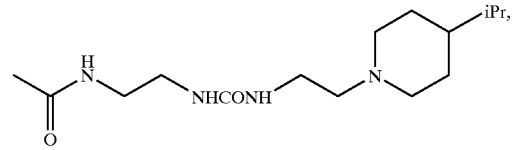

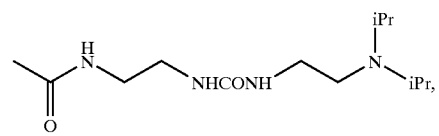

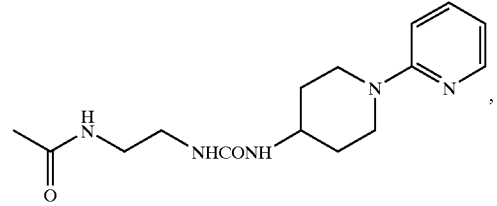

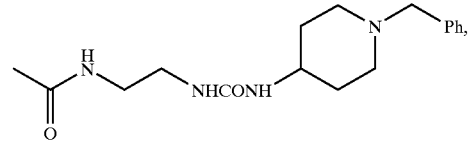

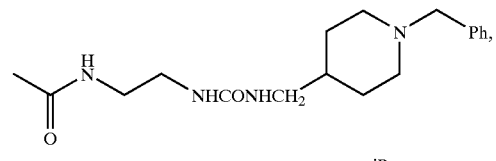

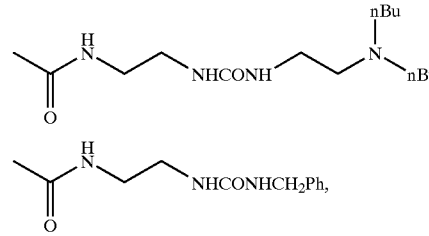

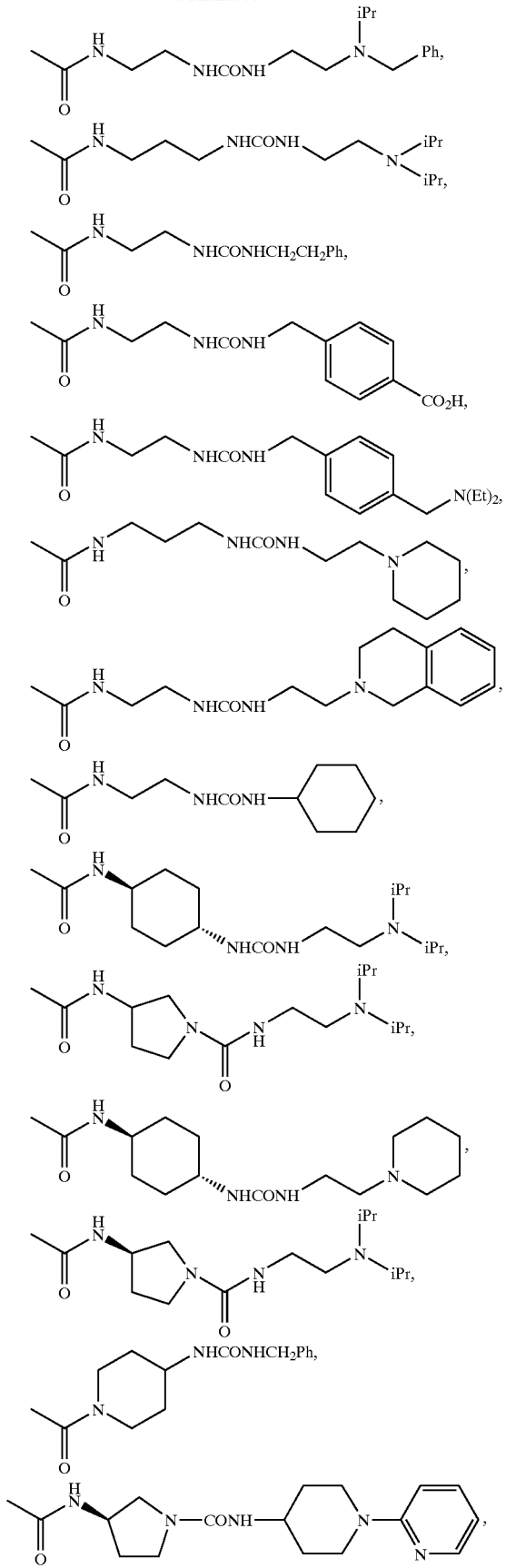

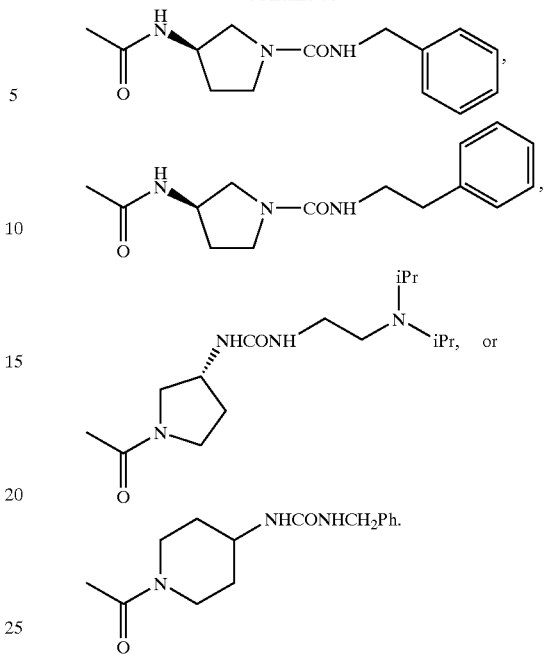

43. A compound as claimed in claim 1 which is 6-[(2,2-diphenylethyl)amino]-9-{(2R,3R,4S,5S)-5-[(ethylamino)carbonyl]-3,4-dihydroxytetrahydro-2-furanyl}-N-{2-[({[1-(2-pyridinyl)-4-piperidinyl]amino}carbonyl)amino]ethyl}-9H-purine-2-carboxamide or a pharmaceutically acceptable salt or solvate thereof.

44. A compound as claimed in claim 1 which is 4-[({[(2-{[(6-[(2,2-diphenylethyl)amino]-9-{(2R,3R,4S,5S)-5-[(ethylamino)carbonyl]-3,4-dihydroxytetrahydro-2-furanyl}-9H-purin-2-yl)carbonyl]amino}ethyl)amino]carbonyl}-amino)methyl]benzoic acid or a pharmaceutically acceptable salt or solvate thereof.

45. A pharmaceutical composition comprising a compound of the formula (I) or a pharmaceutically acceptable salt or solvate thereof, as claimed in claim 1, together with a pharmaceutically acceptable excipient, diluent or carrier.

46. A method of agonising the A2a receptor in a mammal-comprising administering to said mammal in need of such treatment an effective amount of a compound of claim 1 or a pharmaceutically acceptable salt thereof.

47. A method of treating a respiratory disease in a mammal, comprising administering to said mammal in need of such treatment an effective amount of a compound of claim 1 or a pharmaceutically acceptable salt thereof, where the disease is selected from the group consisting of adult respiratory distress syndrome (ARDS), bronchitis, chronic bronchitis, chronic obstructive pulmonary disease, cystic fibrosis, asthma, emphysema, bronchiectasis, chronic sinusitis and rhinitis.

48. A compound of the formula:

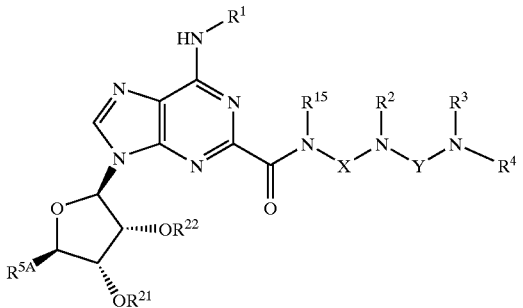

(XXI)

wherein R$^{21}$ and R$^{22}$ are either each a protecting group, or, taken together, are a protecting group, R$^{5A}$ is CH$_2$OH, CH$_2$OR$^{23}$ or CONR$^{14}$R$^{14}$, R$^{23}$ is a protecting group and R$^1$, R$^2$, R$^3$, R$^4$, R$^{14}$, R$^{15}$, X and Y are as defined in claim 1.

49. A compound of the formula:

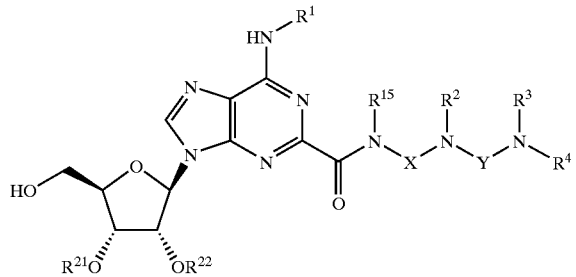

(XXXIX)

wherein R$^{21}$ and R$^{22}$ are either each a protecting group, or, taken together, are a protecting group, and R$^1$, R$^2$, R$^3$, R$^4$, R$^{15}$, X and Y are as defined in claim 1.

50. A compound of the formula:

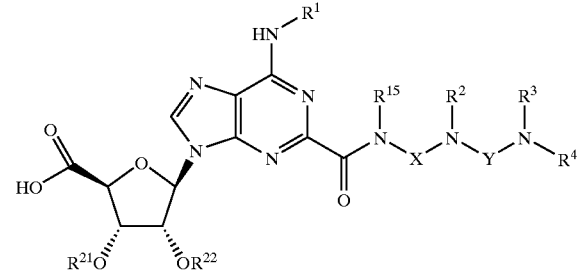

(XXXX)

wherein R$^{21}$ and R$^{22}$ are either each a protecting group, or, taken together, are a protecting group, and R$^1$, R$^2$, R$^3$, R$^4$, R$^{15}$, X and Y are as defined in claim 1.

51. Ethyl 6-[(2,2-diphenylethyl)amino]-9H-purine-2-carboxylate;
ethyl 9-{(2R,3R,4R,5R)-3,4-bis(acetyloxy)-5-[(acetyloxy)methyl]tetrahydro-2-furanyl}-6-[(2,2-diphenylethyl)amino]-9H-purine-2-carboxylate;
ethyl 9-[(2R,3R,4S,5R)-3,4-dihydroxy-5-(hydroxymethyl)tetrahydro-2-furanyl]-6-[(2,2-diphenylethyl)amino]-9H-purine-2-carboxylate;
ethyl 9-[(3aR,4R,6R,6aR)-6-(hydroxymethyl)-2,2-dimethyltetrahydrofuro[3,4-d][1,3]dioxol-4-yl]-6-[(2,2-diphenylethyl)amino]-9H-purine-2-carboxylate;
(3aS,4S,6R,6aR)-6-[6-[(2,2-diphenylethyl)amino]-2-(ethoxycarbonyl)-9H-purin-9-yl]-2,2-dimethyltetrahydrofuro[3,4-d][1,3]dioxole-4-carboxylic acid;
ethyl 9-{(3aR,4R,6S,6aS)-6-[(ethylamino)carbonyl]-2,2-dimethyltetrahydrofuro[3,4-d][1,3]dioxol-4-yl}-6-[(2,2-diphenylethyl)amino]-9H-purine-2-carboxylate;
9-{(3aR,4R,6S,6aS)-6-[(ethylamino)carbonyl]-2,2-dimethyltetrahydrofuro[3,4-d][1,3]dioxol-4-yl}-6-[(2,2-diphenylethyl)amino]-9H-purine-2-carboxylic acid;
9-{(3aR,4R,6S,6aS)-6-[(ethylamino)carbonyl]-2,2-dimethyltetrahydrofuro[3,4-d][1,3]dioxol-4-yl}-6-[(2,2-diphenylethyl)amino]-N-{2-[({[1-(2-pyridinyl)-4-piperidinyl]amino}carbonyl)amino]ethyl}-9H-purine-2-carboxamide;
tert-butyl 2-[({[1-(2-pyridinyl)-4-piperidinyl]amino}carbonyl)amino]ethylcarbamate;
N-(2-aminoethyl)-N'-[1-(2-pyridinyl)-4-piperidinyl]urea dihydrochloride; or
N-(2-aminoethyl)-N'-[1-(2-pyridinyl)-4-piperidinyl]urea.

52. A compound of the formula:

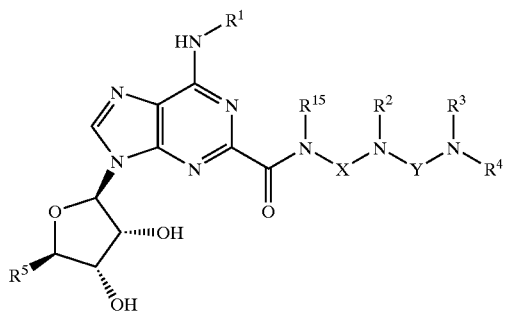

(I)

or a pharmaceutically acceptable salt or solvate thereof, wherein

R$^1$ is H, C$_1$–C$_6$ alkyl or fluorenyl, said C$_1$–C$_6$ alkyl being optionally substituted by 1 or 2 substituents each independently selected from phenyl and naphthyl, said phenyl and naphthyl being optionally substituted by C$_1$–C$_6$ alkyl, C$_1$–C$_6$ alkoxy, halo or cyano;

R$^2$ is H or C$_1$–C$_6$ alkyl;

either, R$^3$ and R$^4$, taken together with the nitrogen atom to which they are attached, represent azetidinyl, pyrrolidinyl, piperidinyl, piperazinyl, homopiperidinyl or homopiperazinyl, each being optionally substituted on a ring nitrogen or carbon atom by C$_1$–C$_6$ alkyl or C$_3$–C$_8$ cycloalkyl and optionally substituted on a ring carbon atom not adjacent to a ring nitrogen atom by —NR$^6$R$^7$, or, R$^3$ is H, C$_1$–C$_6$ alkyl, C$_3$–C$_8$ cycloalkyl or benzyl and R$^4$ is (a) azetidin-3-yl, pyrrolidin-3-yl, piperidin-3-yl, piperidin-4-yl, homopiperidin-3-yl or homopiperidin-4-yl, each being optionally substituted by C$_1$–C$_6$ alkyl, C$_3$–C$_8$ cycloalkyl, phenyl, benzyl or het, or (b) —(C$_2$–C$_6$ alkylene)-R$^8$, or (c) —(C$_1$–C$_6$ alkylene)-R$^{13}$;

R$^5$ is CH$_2$OH or CONHR$^{14}$;

R$^6$ and R$^7$ are either each independently H or C$_1$–C$_6$ alkyl or, taken together with the nitrogen atom to which they are attached, represent azetidinyl, pyrrolidinyl or piperidinyl, said azetidinyl, pyrrolidinyl and piperidinyl being optionally substituted by $C_1$–$C_6$ alkyl;

$R^8$ is (i) azetidin-1-yl, pyrrolidin-1-yl, piperidin-1-yl, morpholin-4-yl, piperazin-1-yl, homopiperidin-1-yl, homopiperazin-1-yl or tetrahydroisoquinolin-1-yl, each being optionally substituted on a ring carbon atom by $C_1$–$C_6$ alkyl, $C_3$–$C_8$ cycloalkyl, phenyl, $C_1$–$C_6$ alkoxy-($C_1$–$C_6$)-alkyl, $R^9R^9N$—($C_1$–$C_6$)-alkyl, fluoro-($C_1$–$C_6$)-alkyl, —$CONR^9R^9$, —$COOR^9$ or $C_2$–$C_5$ alkanoyl, and optionally substituted on a ring carbon atom not adjacent to a ring nitrogen atom by fluoro-($C_1$–$C_6$)-alkoxy, halo, —$OR^9$, cyano, —$S(O)_mR^{10}$, —$NR^9R^9$, —$SO_2NR^9R^9$, —$NR^9COR^{10}$ or —$NR^9SO_2R^{10}$, and said piperazin-1-yl and homopiperazin-1-yl being optionally substituted on the ring nitrogen atom not attached to the $C_2$–$C_6$ alkylene group by $C_1$–$C_6$ alkyl, phenyl, $C_1$–$C_6$ alkoxy-($C_2$–$C_6$)-alkyl, $R^9R^9N$-($C_2$–$C_6$)-alkyl, fluoro-($C_1$–$C_6$)-alkyl, $C_2$–$C_5$ alkanoyl, —$COOR^{10}$, $C_3$–$C_8$ cycloalkyl, —$SO_2R^{10}$, —$SO_2NR^9R^9$ or —$CONR^9R^9$, or (ii) $NR^{11}R^{12}$;

$R^9$ is H, $C_1$–$C_6$ alkyl, $C_3$–$C_8$ cycloalkyl or phenyl;

$R^{10}$ is $C_1$–$C_6$ alkyl, $C_3$–$C_8$ cycloalkyl or phenyl;

$R^{11}$ is H, $C_1$–$C_6$ alkyl, $C_3$–$C_8$ cycloalkyl or benzyl;

$R^{12}$ is H, $C_1$–$C_6$ alkyl, $C_3$–$C_8$ cycloalkyl, phenyl, benzyl, fluoro-($C_1$–$C_6$)-alkyl, —$CONR^9R^9$, —$COOR^{10}$, $C_2$–$C_5$ alkanoyl or —$SO_2NR^9R^9$;

$R^{13}$ is phenyl, pyridin-2-yl, pyridin-3-yl or pyridin-4-yl, each being optionally substituted by $C_1$–$C_6$ alkyl, $C_1$–$C_6$ alkoxy, halo or cyano;

$R^{14}$ is H or $C_1$–$C_6$ alkyl optionally substituted by cyclopropyl;

$R^{15}$ is H or $C_1$–$C_6$ alkyl;

m is 0, 1 or 2;

X is unbranched $C_2$–$C_3$ alkylene optionally substituted by $C_1$–$C_6$ alkyl or $C_3$–$C_8$ cycloalkyl;

Y is CO, CS, $SO_2$ or $C=N(CN)$; and

"het", used in the definition of $R^4$, is a C-linked, 4- to 6-membered ring, heterocycle having either from 1 to 4 ring nitrogen heteroatoms or 1 or 2 nitrogen ring heteroatoms and 1 oxygen or 1 sulphur ring heteroatom, optionally substituted by $C_1$–$C_6$ alkyl, $C_3$–$C_8$ cycloalkyl, $C_1$–$C_6$ alkoxy, $C_3$–$C_8$ cycloalkoxy, hydroxy, oxo or halo.

53. A method of any one of claims 46 and 47 wherein said mammal is a human.

* * * * *